US006365392B1

(12) United States Patent
Tripp et al.

(10) Patent No.: US 6,365,392 B1
(45) Date of Patent: *Apr. 2, 2002

(54) FILARIID NEMATODE CYSTEINE PROTEASE NUCLEIC ACID MOLECULES AND USES THEREOF

(75) Inventors: Cynthia Ann Tripp; Nancy Wisnewski, both of Ft. Collins; Robert B. Grieve, Fort Collins; Glenn R. Frank, Wellington, all of CO (US)

(73) Assignees: Heska Corporation; Colorado State University Research Foundation

( * ) Notice: Subject to any disclaimer, the term of this patent is extended or adjusted under 35 U.S.C. 154(b) by 0 days.

This patent is subject to a terminal disclaimer.

(21) Appl. No.: 09/005,298

(22) Filed: Jan. 9, 1998

Related U.S. Application Data

(62) Division of application No. 08/768,619, filed on Dec. 18, 1996, which is a continuation-in-part of application No. PCT/US96/09848, filed on Jun. 7, 1996, which is a continuation-in-part of application No. 08/486,036, filed on Jun. 7, 1995, now Pat. No. 5,795,768, which is a continuation-in-part of application No. 08/153,554, filed on Nov. 16, 1993, now abandoned, which is a continuation of application No. 07/792,209, filed on Nov. 12, 1991, now abandoned, application No. 09/005,298, which is a continuation-in-part of application No. 08/482,282, filed on Jun. 7, 1995, now Pat. No. 5,792,624, which is a continuation-in-part of application No. 08/153,554, which is a continuation of application No. 07/792,209, said application No. 08/482,282, is a continuation-in-part of application No. 08/101,283, filed on Aug. 3, 1993, now abandoned, which is a continuation of application No. 07/654,226, filed on Feb. 12, 1991, now abandoned, said application No. 08/486,036, is a continuation-in-part of application No. 08/101,283, which is a continuation of application No. 07/654,226.

(51) Int. Cl.$^7$ ............ C12N 7/01; C12N 15/11; C12N 15/52; C12N 15/63; C12N 5/10

(52) U.S. Cl. ............ 435/235.1; 435/320.1; 435/325; 435/243; 435/183; 536/23.1; 536/23.2; 536/24.3; 514/44; 424/265.1; 424/94.1

(58) Field of Search ............ 435/69.1, 69.7, 435/183, 235.1, 240.2, 342, 252.3, 320.1, 325; 536/23.1, 23.2, 23.4, 23.5, 23.7, 24.3; 514/44; 935/1, 14; 424/265.1, 94.1

(56) References Cited

U.S. PATENT DOCUMENTS

| 4,842,999 A | 6/1989 | Fuller et al. ............ 435/7 |
| 5,691,186 A | * 11/1997 | Tripp et al. |

FOREIGN PATENT DOCUMENTS

| EP | 0 434 909 A2 | 7/1991 |
| EP | 0 524 834 A2 | 1/1993 |
| WO | WO 87/06467 | 11/1987 |
| WO | WO 94/06280 | 3/1994 |
| WO | WO 94/09142 | 4/1994 |

OTHER PUBLICATIONS

Dinman et al. Exp. Parasitol. Aug. 1990 vol. 71 (2), 176–88.*
Basch in Vaccines and World Health Science, Policy & Practice 1994, p. 245, Oxford Univ. Press, Inc., New York.*
Zeng et al. Mol. Cell. Biol. 1990 vol. 6(10), 2765–2773.*
Sakanari et al. Proc. Natl. Acad. Sci. 1989 vol. 86, p. 4863–4867.*
Arlot–Bonnemains et al., 1996, *Biochem.*, 319:975–82.
Abraham et al., 1990, *Exp. Parasitol.*, 70:314–322.
Abraham et al., 1987, *J. Parasitol.*, 73(2):377–383.
Aimri et al., 1988, *Mol. Biochem. Parasitol.*, 28:113–120.
Boulay et al., 1995, *Comp. Biochem. Physiol.*, 111B(3):353–359.
Boulay et al., 1996, *J. Comp. Physiol B*, 166:310–318.
Chung et al., 1995, *J. Parasitol.*, p. 137–142.
Cox et al., 1990, *Mol. Biochem. Parasitol.*, 41:25–34.
Dalton et al., 1989, *Mol. Biochem. Parasitol.*, 35:161–166.
Dresden et al., 1985, *Exp. Parasitol.*, 59:257–263.
Gamble et al., 1989, *Mol. Biochem. Parasitol.*, 33:49–58.
Grieve et al., 1983, *Epidem. Rev.*, 5:220–246.
Ham et al., 1994, *Trans. Royal Soc. Trop. Med. Hyg.*, 88:132–135.
Heussler et al., 1994, *Mol. Biochem. Parasitol.*, 64:11–23.
Heussler et al., 1994, *Trop. Med. Parasitol.*, 45(Supp. II):179.
Hong et al., 1993, *Exp. Parasitol.*, 76:127–133.
Hotez et al., 1985, *J. Biol. Chem.*, 260:7343–7348.
Lackey et al., 1989, *Exp. Parasitol.*, 68:176–185.
Lustigman et al., 1992, *J. Biol. Chem.*, 267(24):17339–17346.
Lustigman, 1993, *Parasitol. Today*, 9(8):294–297.
Lustigman et al., 1996, *J. of Biological Chem.*, 271(47):30181–30189.
Maizels et al., 1989, *TIBTECH*, 7(11):316–321.
Maki et al., 1986, *J. Helminthol.*, 60:31–37.
McKerrow et al., 1985, *J. Biol. Chem.*, 231:47–51.
McKerrow et al., 1982, *Exp. Parasitol.*, 53:249–254.
Petralanda et al., 1986, *Mol. Biochem. Parasitol.*, 19:51–59.
Pratt et al., 1992, *Mol. Biochem. Parasitol.*, 51:209–218.

(List continued on next page.)

Primary Examiner—Michael Pak
(74) Attorney, Agent, or Firm—Heska Corporation

(57) ABSTRACT

The present invention provides for filariid nematode cysteine protease proteins; to filariid nematode cysteine protease nucleic acid molecules, in particular, *Dirofilaria immitis* L3 larval cysteine protease nucleic acid molecules and *Onchocerca volvulus* L3 larval cysteine protease nucleic acid molecules; to antibodies raised against such proteins, and to compounds that inhibit filariid nematode cysteine protease activity. The present invention also includes methods to obtain such proteins, nucleic acid molecules, antibodies and/or inhibitors. The present invention also includes therapeutic compositions comprising such proteins, nucleic acid molecules, antibodies and/or inhibitors, and the use of such compositions to protect an animal from disease caused by parasitic helminths.

15 Claims, No Drawings

OTHER PUBLICATIONS

Richer et al., 1993, *Exp. Parasitol.*, 76:1–11.
Richer et al., 1992, *Exp. Parasitol.*, 75:213–222.
Robertson et al., 1989, *Exp. Parasitol.*, 69:167–173.
Rogers, 1982, *J. Parasitol.*, 12:495–502.
Swamy et al., 1983, *Mol. Biochem. Parasitol.*, 9:1–14.
Tomashiro et al., 1987, *J. Parasitol.*, 73:149–154.
Wijffels, 1994, *Biochem. J.*, 299:781–790 (Abstract).
Yamakami, 1995, *Eur. J. Biochem.*, 233:490–497.
Molecular SIGMA Biology catalog, A New Dimension, 1989, Oligonucleotide Products, p. 54.
Feng et al., 1985, *J. Mol. Evol.*, 21:112–125.
Johnson et al., 1993, *J. Mol. Biol.*, 233:716–738.
Meinkoth et al., 1984, *Analytical Biochemistry*, 138:267–284.
Selzer et al., 1997, Genbank Accession No. AF031819, Direct Genbank submission.

* cited by examiner

FILARIID NEMATODE CYSTEINE PROTEASE NUCLEIC ACID MOLECULES AND USES THEREOF

CROSS REFERENCE TO RELATED APPLICATIONS

This application is a divisional of co-pending U.S. application Ser. No. 08/768,619, filed Dec. 18, 1996, entitled "Novel Filariid Nematode Cysteine Protease Proteins, Nucleic Acid Molecules, and Uses Thereof" which is a continuation-in-part of pending PCT application PCT/US96/09848 which designates the United States, filed Jun. 7, 1996, which is a continuation-in-part of pending U.S. patent application Ser. No. 08/486,036, filed on Jun. 7, 1995, now U.S. Pat. No. 5,795,768, issued Aug. 18, 1998, entitled "FILARIID NEMATODE CYSTEINE PROTEASE PROTEINS, NUCLEIC ACID MOLECULES AND USES THEREOF," which is a continuation-in-part of U.S. patent application Ser. No. 08/153,554, filed Nov. 16, 1993, now abandoned, entitled "PROTEASE VACCINE AGAINST HEARTWORM", which is a continuation of U.S. patent application Ser. No. 07/792,209, filed Nov. 12, 1999, now abandoned. The present application is also a continuation-in-part of U.S. patent application Ser. No. 08/482,282, filed Jun. 7, 1995, now U.S. Pat. No. 5,792,624, entitled "DIROFILARIA AND ONCHOCERCA LARVAL L3 CYSTEINE PROTEASE PROTEINS AND USES THEREOF," which is a continuation-in-part of U.S. patent application Ser. No. 08/153,554, filed Nov. 16, 1993, now abandoned, which is a continuation of U.S. patent application Ser. No. 07/792,209, filed Nov. 12, 1991, now abandoned. U.S. patent application Ser. No. 08/482,282 is also a continuation-in-part of U.S. patent application Ser. No. 08/101,283, filed Aug. 3, 1993, now abandoned, which is a continuation of U.S. patent application Ser. No. 07/654,226, filed Feb. 12, 1991, now abandoned. U.S. patent application Ser. No. 08/486,036 is also a continuation-in-part of U.S. patent application Ser. No. 08/101,283, filed Aug. 3, 1993, now abandoned entitled "REAGENTS AND METHODS FOR IDENTIFICATION OF VACCINES", which is a continuation of U.S. patent application Ser. No. 07/654,226, filed Feb. 12, 1999, now abandoned. Each of the above applications is incorporated by reference herein in its entirety.

FIELD OF THE INVENTION

The present invention relates to novel filariid nematode protease genes, proteins encoded by such genes, antibodies raised against such proteins, and protease inhibitors produced using such proteins. Particular proteases of the present invention include cysteine proteases. The present invention also includes therapeutic compositions comprising such nucleic acid molecules, proteins, antibodies and inhibitors, as well as their use to protect animals from disease caused by helminth parasites, such as by tissue-migrating helminths, including Dirofilaria and Onchocerca.

BACKGROUND OF THE INVENTION

Parasite infections in animals, including humans, are typically treated by chemical drugs, because there are essentially no efficacious vaccines available. One disadvantage with chemical drugs is that they must be administered often. For example, dogs susceptible to heartworm are typically treated monthly to maintain protective drug levels. Repeated administration of drugs to treat parasite infections, however, often leads to the development of resistant strains that no longer respond to treatment. Furthermore, many of the chemical drugs are harmful to the animals being treated, and as larger doses become required due to the build up of resistance, the side effects become even greater.

It is particularly difficult to develop vaccines against parasite infections both because of the complexity of the parasite's life cycle and because, while administration of parasites or parasite antigens can lead to the production of a significant antibody response, the immune response is typically not sufficient to protect the animal against infection.

As for most parasites, the life cycle of Dirofilaria immitis, the helminth that causes heartworm, includes a variety of life forms, each of which presents different targets, and challenges, for immunization. Adult forms of the parasite are quite large and preferentially inhabit the heart and pulmonary arteries of an animal. Sexually mature adults, after mating, produce microfilariae which traverse capillary beds and circulate in the vascular system. The microfilariae are ingested by female mosquitos during blood feeding on an infected dog, subsequent development of the microfilariae into two larval stages (L1 and L2) occurs in the mosquito. The microfilariae go through and finally become mature third stage larvae (L3) which can then be transmitted back to a dog through the bite of the mosquito. It is this L3 stage, therefore, that accounts for the initial infection. As early as three days after infection, the L3 molt to the fourth larval (L4) stage, and subsequently to the fifth stage, or immature adults. The immature adults migrate to the heart and pulmonary arteries, where they mature and reproduce, thus producing the microfilariae in the blood. "Occult" infection with heartworm in dogs is defined as an infection in which no microfilariae can be detected, but the existence of adult heartworms can be determined through thoracic examination.

Both the molting process and tissue migration are likely to involve the action of one or more enzymes, including proteases. Although protease activity has been identified in a number of parasites (including in larval excretory-secretory products) as well as in mammals, there has been no identification of a cysteine protease gene in any filariid nematode.

Cysteine protease genes have been isolated from several mammalian sources and from the nematodes *Haemonchus contortus* (e.g., Pratt et al., 1992, *Mol. Biochem. Parasitol.* 51, 209–218) and *Caenorhabditis elegans* (Ray et al., 1992, *Mol. Biochem. Parasitol.* 51, 239–250). In addition, consensus sequences, particularly around the active sites, have also been identified for serine and cysteine proteases; see, for example, Sakanari et al., 1989, *Proc. Natl. Acad. Sci. USA* 86, 4863–4867. The determination of these sequences, however, does not necessarily predict that the cloning of novel cysteine protease genes will be straight-forward, particularly since the sequences shared by different cysteine proteases are such that probes and primers based on the consensus sequences are highly degenerative.

Heartworm not only is a major problem in dogs, which typically are unable to develop immunity after infection (i.e., dogs can become reinfected even after being cured by chemotherapy), but is also becoming increasingly widespread in other companion animals, such as cats and ferrets. Heartworm infections have also been reported in humans. Other parasite infections are also widespread, and all require better treatment, including preventative vaccine programs and/or targeted drug therapies.

SUMMARY OF THE INVENTION

One embodiment of the present invention relates to an isolated filariid nematode larval nucleic acid molecule that hybridizes, under stringent hybridization conditions, with a *Dirofilaria immitis* L3 larval cysteine protease gene and/or an *Onchocerca volvulus* L3 larval cysteine protease gene. A preferred nucleic acid molecule of the present invention includes at least a portion of SEQ ID NO:1, SEQ ID NO:3, SEQ ID NO:5, SEQ ID NO:7, SEQ ID NO:14, SEQ ID NO:16, SEQ ID NO:26, SEQ ID NO:27, SEQ ID NO:28, SEQ ID NO:29, SEQ ID NO:30, SEQ ID NO:31, SEQ ID NO:32, SEQ ID NO:34, SEQ ID NO:35, SEQ ID NO:36, SEQ ID NO:37, SEQ ID NO:39, or an allelic variant of one or more of those nucleic acid sequences. The present invention also includes recombinant molecules and recombinant cells that include filariid nematode cysteine protease nucleic acid molecules of the present invention. Also included are methods to produce such nucleic acid molecules, recombinant molecules and recombinant cells of the present invention.

Another embodiment of the present invention is an isolated protein that includes a filariid nematode larval cysteine protease protein or a mimetope of such a protein. A filariid nematode cysteine protease protein of the present invention preferably has cysteine protease activity and/or comprises a protein that, when administered to an animal, is capable of eliciting an immune response against a natural helminth cysteine protease protein. The present invention also includes inhibitors of cysteine protease activity as well as antibodies that recognize (i.e., selectively bind to) a filariid nematode cysteine protease protein and/or mimetope thereof of the present invention. Also included are methods to produce such proteins, inhibitors and antibodies of the present invention.

Yet another embodiment of the present invention is a therapeutic composition capable of protecting an animal from disease caused by a parasitic helminth. Such a therapeutic composition comprises at least one of the following protective compounds: an isolated parasitic filariid nematode larval nucleic acid molecule that hybridizes under stringent hybridization conditions with a *Dirofilaria immitis* L3 larval cysteine protease gene and/or an *Onchocerca volvulus* L3 larval cysteine protease gene; an isolated filariid nematode larval cysteine protease protein or a mimetope thereof; an isolated antibody that selectively binds to a filariid nematode L3 larval cysteine protease protein; and an inhibitor of cysteine protease activity identified by its ability to inhibit filariid nematode L3 larval cysteine protease activity. Also included is a method to protect an animal from disease caused by a parasitic helminth that includes administering to the animal a therapeutic composition of the present invention. A preferred therapeutic composition of the present invention is a composition capable of protecting an animal from heartworm.

The present invention also includes a-method to identify a compound capable of inhibiting cysteine protease activity of a parasitic helminth. Such a method includes (a) contacting an isolated filariid nematode larval cysteine protease protein with a putative inhibitory compound under conditions in which, in the absence of the compound, the protein has cysteine protease activity; and (b) determining if the putative inhibitory compound inhibits the activity. Also included is a test kit to identify a compound capable of inhibiting cysteine protease activity that includes an isolated filariid nematode larval cysteine protease protein having cysteine protease activity and a means for determining the extent of inhibition of cysteine protease activity in the presence of a putative inhibitory compound.

DETAILED DESCRIPTION OF THE INVENTION

The present invention provides for filariid nematode L3 larval cysteine protease proteins and nucleic acid molecules, as well as, antibodies directed against filariid nematode L3 larval cysteine protease proteins. Also included in the present invention is the use of these proteins, nucleic acid molecules and antibodies as therapeutic compositions to treat parasitic helminth diseases as well as in other applications, such as those disclosed below.

One embodiment of the present invention is an isolated filariid nematode L3 larval cysteine protease protein. A cysteine protease is referred to herein as "CP." A CP that can be found in third stage larvae (L3) is referred to herein as L3 larval CP. That such a protease is referred to as an L3 larval protease does not preclude that protease from also being present in other life stages of a helminth. Indeed, *D. immitis* L3 CP is also found in fourth stage larvae (L4), suggesting that L3 CP's of the present invention, in general, can also be found in L4. Furthermore, the inventors discovered that immune dog serum prepared as disclosed in PCT Patent Publication No. WO 92/13560, published Aug. 20, 1992, selectively binds to larval CP's of the present invention, a finding that enabled isolation of the first filariid nematode CP nucleic acid molecule.

According to the present invention, an isolated, or biologically pure, protein, is a protein that has been removed from its natural milieu. As such, "isolated" and "biologically pure" do not necessarily reflect the extent to which the protein has been purified. An isolated CP protein of the present invention can be obtained from its natural source, can be produced using recombinant DNA technology or can be produced by chemical synthesis. As used herein, an isolated CP protein of the present invention can be a full-length protein or any homologue of such a protein. Examples of CP homologues include CP proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homologue includes at least one epitope capable of eliciting an immune response against a CP protein of the present invention. That is, when the homologue is administered to an animal as an immunogen, using techniques known to those skilled in the art, the animal will produce a humoral and/or cellular immune response against at least one epitope of a CP protein of the present invention. The ability of a protein to effect an immune response, can be measured using techniques known to those skilled in the art.

Homologues of CP proteins of the present invention can be the result of natural allelic variation or natural mutation. CP protein homologues of the present invention can also be produced using techniques known in the art including, but not limited to, direct modifications to the protein or modifications to the gene encoding the protein using, for example, classic or recombinant DNA techniques to effect random or targeted mutagenesis. Isolated proteins of the present invention, including homologues, can be identified in a straight-forward manner by the proteins' ability to elicit an immune response against filariid nematode CP proteins.

CP proteins of the present invention, including homologues of the full-length protein, have the further characteristic of being encoded by nucleic acid molecules that hybridize under stringent hybridization conditions to at least one of the following genes: (a a gene encoding a *Dirofilaria immitis* L3 cysteine protease protein (i.e., a *D. immitis* CP gene); and (b) a gene encoding an *Onchocerca volvulus* L3 cysteine protease protein (i.e., an *O. volvulus* CP gene). It is to be noted that the term "a" or "an" entity refers to one or more of that entity; for example, a gene refers to one or more genes or at least one gene. As such, the terms "a" (or "an"), "one or more" and "at least one" can be used interchangeably herein. It is also to be noted that the terms "comprising", "including", and "having" can be used interchangeably.

As used herein, stringent hybridization conditions refer to standard hybridization conditions under which nucleic acid molecules, including oligonucleotides, are used to identify molecules having similar nucleic acid sequences. Such standard conditions are disclosed, for example, in Sambrook et al., 1989, *Molecular Cloning: A Laboratory Manual*, Cold Spring Harbor Labs Press. Examples of such conditions are provided in the Examples section of the present application. Stringent hybridization conditions typically permit isolation of nucleic acid molecules having at least about 70% nucleic acid sequence identity with the nucleic acid molecule being used as a probe in the hybridization reaction. Formulae to calculate the appropriate hybridization and wash conditions to achieve hybridization permitting 30% or less mis-match between two nucleic acid molecules are disclosed, for example, in Meinkoth et al, 1984, *Anal. Biochem* 138, 267–284; Meinkoth et al, ibid, is incorporated by reference herein in its entirety.

As used herein, a *D. immitis* CP gene includes all nucleic acid sequences related to a natural *D. immitis* CP gene such as regulatory regions that control production of the *D. immitis* CP protein encoded by that gene (such as, but not limited to, transcription, translation or post-translation control regions) as well as the coding region itself. In one embodiment, a *D. immitis* CP gene includes the nucleic acid sequence SEQ ID NO:1 and/or SEQ ID NO:26. Nucleic acid sequence SEQ ID NO:1 represents the deduced sequence of a cDNA (complementary DNA) nucleic acid molecule denoted herein as $nDiCP_{1298}$, the production of which is disclosed in the Examples. The complement of SEQ ID NO:1 (represented herein by SEQ ID NO:26) refers to the nucleic acid sequence of the strand complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is complementary to (i.e., can form a double helix with) the strand for which the sequence is cited. It should be noted-that since nucleic acid sequencing technology is not entirely error-free, SEQ ID NO:1 (as well as other nucleic acid and protein sequences presented herein), at best, represents an apparent nucleic acid sequence of the nucleic acid molecule encoding a *D. immitis* CP protein of the present invention. In another embodiment, a *D. immitis* CP gene includes the nucleic acid sequence SEQ ID NO:32 and/or SEQ ID NO:35. Nucleic acid SEQ ID NO:32 represents the deduced nucleic acid sequence of the coding strand of $nDiCP_{1304}$, and SEQ ID NO:35 is the sequence of the complementary strand of $nDiCP_{1304}$.

In another embodiment, a *D. immitis* CP gene can be an allelic variant that includes a similar but not identical sequence to SEQ ID NO:1 and/or SEQ ID NO:26. An allelic variant of a *D. immitis* CP gene including SEQ ID NO:1 and/or SEQ ID NO:26 is a gene that occurs at essentially the same locus (or loci) in the genome as the gene including SEQ ID NO:1 and/or SEQ ID NO:26, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given parasitic helminth since the genome is diploid and/or among a group of two or more filariid nematodes. In another embodiment, a *D. immitis* CP gene can be an allelic variant that includes a similar but not identical sequence to SEQ ID NO:32 and/or SEQ ID NO:35.

Similarly, an *O. volvulus* CP gene includes all nucleic acid sequences related to a natural *O. volvulus* CP gene such as regulatory regions that control production of the *O. volvulus* CP protein encoded by that gene as well as the coding region itself. In one embodiment, an *O. volvulus* CP gene includes the nucleic acid sequence SEQ ID NO:5, SEQ ID NO:14, SEQ ID NO:28 and/or SEQ ID NO:30. Nucleic acid sequence SEQ ID NO:5 represents the deduced sequence of a cDNA (complementary DNA) nucleic acid molecule denoted herein as $nOvCP_{291}$, the production of which is disclosed in the Examples. The complement of SEQ ID NO:5 is referred to herein as SEQ ID NO:28. Nucleic acid sequence SEQ ID NO:14 represents the deduced sequence of a PCR nucleic acid molecule denoted herein as $nOvCP_{1306}$, the production of which is disclosed in the Examples. The complement of SEQ ID NO:14 is referred to herein as SEQ ID NO:30. In another embodiment, an *O. volvulus* CP gene can be an allelic variant that includes a similar but not identical sequence to SEQ ID NO:5, SEQ ID NO:14, SEQ ID NO:28 and/or SEQ ID NO:30.

The minimal size of a CP protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich.

As such, the minimal size of a nucleic acid molecule used to encode a CP protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a CP protein homologue of the present invention is from about 4 to about 6 amino acids in length, with preferred sizes depending on whether a full-length, fusion, multivalent, or functional portions of such proteins are desired.

Protein homologues of the present invention preferably are capable of eliciting an immune response against a filariid nematode CP protein; of selectively binding to immune serum using techniques as disclosed in PCT Patent Publication No. WO 92/13560 (ibid.); and/or of having cysteine protease activity. The minimum size of a protein capable of eliciting an immune response is a minimum size sufficient to form an epitope, a size that typically is at least from about 5 to about 9 amino acids. As is appreciated by those skilled in the art, an epitope can include amino acids that naturally are contiguous to each other as well as amino acids that, due to the tertiary structure of the natural protein, are in sufficiently close proximity to form an epitope. Methods to measure an immune response or cysteine protease activity are known to those of skill in the art.

Any filariid nematode CP protein is a suitable CP protein of the present invention. Suitable filariid nematodes from which to isolate CP proteins (including isolation of the natural protein or production of the protein by recombinant or synthetic techniques) include, but are not limited to, filariid nematodes of the genera Dirofilaria, Onchocerca, Acanthocheilonema, Brugia, Dipetalonema, Loa, Parafilaria, Setaria, Stephanofilaria and Wuchereria. Preferred filariid nematodes include nematodes of the genera Dirofilaria and Onchocerca, with *D. immitis*, the parasite that causes heartworm, and *O. volvulus*, the parasite that causes onchocerciasis, being more preferred.

A preferred filariid nematode CP protein of the present invention is a compound that when administered to an animal in an effective manner, is capable of protecting that animal from disease caused by a parasitic helminth. As such, the parasitic helminth is essentially incapable of causing disease in an animal that is immunized with a filariid nematode CP protein of the present invention. In accordance with the present invention, the ability of a CP protein of the present invention to protect an animal from disease by a parasitic helminth refers to the ability of that protein to treat, ameliorate and/or prevent disease, including infection leading to disease, caused by the parasitic helminth, preferably by eliciting an immune response against the parasitic helminth. Such an immune response can include humoral and/or cellular immune responses.

Suitable parasites to target include any parasite that is susceptible to inhibition of cysteine protease activity. In one embodiment, such a parasite is essentially incapable of causing disease in an animal administered a CP protein of the present invention. As such, a parasite to target includes any parasite that produces a protein having one or more epitopes that can be targeted by a humoral and/or cellular immune response against a CP protein of the present invention and/or that can be targeted by a compound that otherwise inhibits CP activity, thereby resulting in the reduced ability of the parasite to cause disease in an animal. Suitable and preferred parasites to target include those parasitic helminths disclosed above as being useful in the production of filariid nematode proteins of the present invention. Additional suitable and preferred parasitic helminths to target are listed elsewhere herein.

It is to be appreciated that the present invention also includes mimetopes of CP proteins of the present invention that can be used in accordance with methods as disclosed for CP proteins of the present invention. As used herein, a mimetope of a CP protein of the present invention refers to any compound that is able to mimic the activity of such a CP protein, often because the mimetope has a structure that mimics the CP protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of the present invention is a fusion protein that includes a filariid nematode CP protein-containing domain attached to a fusion segment. Inclusion of a fusion segment as part of a CP protein of the present invention can enhance the protein's stability during production, storage and/or use. Depending on the segment's characteristics, a fusion segment can also act as an immunopotentiator to enhance the immune response mounted by an animal immunized with a filariid nematode CP protein containing such a fusion segment. Furthermore, a fusion segment can function as a tool to simplify purification of a filariid nematode CP protein, such as to enable purification of the resultant fusion protein using affinity chromatography. A suitable fusion segment can be a domain of any size that has the desired function (e.g., imparts increased stability, imparts increased immunogenicity to a protein, and/or simplifies purification of a protein). It is within the scope of the present invention to use one or more fusion segments. Fusion segments can be joined to amino and/or carboxyl termini of the CP-containing domain of the protein. Linkages between fusion segments and CP-containing domains of fusion proteins can be susceptible to cleavage in order to enable straight-forward recovery of the CP-containing domains of such proteins. Fusion proteins are preferably produced by culturing a recombinant cell transformed with a fusion nucleic acid molecule that encodes a protein including the fusion segment attached to either the carboxyl and/or amino terminal end of a CP-containing domain.

Preferred fusion segments for use in the present invention include a glutathione binding domain, such as *Schistosoma japonicum* glutathione-S-transferase (GST) or a portion thereof capable of binding to glutathione; a metal binding domain, such as a poly-histidine segment capable of binding to a divalent metal ion; an immunoglobulin binding domain, such as Protein A, Protein G, T cell, B cell, Fc receptor or complement protein antibody-binding domains; a sugar binding domain such as a maltose binding domain from a maltose binding protein; and/or a "tag" domain (e.g., at least a portion of β-galactosidase, a strep tag peptide, other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide. An example of a particularly preferred fusion protein of the present invention is PHIS-PDiCP$_{314}$ and PHIS-POvCP$_{40}$ production of which is disclosed herein.

Another embodiment of the present invention is a filariid nematode CP protein that also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one infectious agent.

Examples of multivalent protective compounds include, but are not limited to, a CP protein of the present invention attached to one or more compounds protective against one or more other infectious agents, particularly an agent that infects humans, cats, dogs, cattle and/or horses, such as, but not limited to: viruses (e.g., caliciviruses, distemper viruses, hepatitis viruses, herpesviruses, immunodeficiency viruses, infectious peritonitis viruses, leukemia viruses, panleukopenia viruses, parvoviruses, rabies viruses, other cancer-causing or cancer-related viruses); bacteria (e.g., Leptospira, Rochalimaea); fungi and fungal-related microorganisms (e.g., Candida, Cryptococcus, Histoplasma); and other parasites (e.g., Babesia, Cryptosporidium, Eimeria, Encephalitozoon, Hepatozoon, Isospora, Microsporidia, Neospora, Nosema, Plasmodium, Pneumocystis, Toxoplasma, as well as helminth parasites, such as those disclosed herein). In one embodiment, a *D. immitis* CP protein of the present invention is attached to one or more additional compounds protective against heartworm. In another embodiment, an *O. volvulus* CP protein of the present invention is attached to one or more additional compounds protective against onchocerciasis.

A preferred filariid nematode CP protein of the present invention is a protein encoded by a nucleic acid molecule that hybridizes under stringent hybridization conditions with nucleic acid molecule $nDiCP_{1298}$, nucleic acid molecule $nDiCP_{1304}$, nucleic acid molecule $nOvCP_{291}$, and/or $nOvCP_{1306}$. Such a CP protein is encoded by a nucleic acid molecule that hybridizes under stringent hybridization conditions with a nucleic acid molecule having a sequence complementary to nucleic acid sequence SEQ ID No:1, SEQ ID NO:3, SEQ ID NO:5, SEQ ID NO:7, SEQ ID NO:14, SEQ ID NO:16, SEQ ID NO:32, SEQ ID NO:34, and SEQ ID NO:37; i.e., nucleic acid sequences SEQ ID NO:26, SEQ ID NO:27, SEQ ID NO:28, SEQ ID NO:29, SEQ ID NO:30, SEQ ID NO:31, SEQ ID NO:35, SEQ ID NO:36, SEQ ID NO:39, and/or other sequences disclosed herein.

The nucleic acid molecule $nDiCP_{1298}$ contains an open reading frame which is represented herein by SEQ ID NO:1. The open reading frame in $nDiCP_{1298}$ (SEQ ID NO:1) extends from the first nucleotide up to the stop codon beginning at about nucleotide 1195 and encodes a protein of about 398 amino acids, denoted herein as $PDiCP_{398}$, the deduced amino acid sequence of which is represented herein as SEQ ID NO:2. The sequence represented by SEQ ID NO:1suggests that an initiating methionine (ATG) may be located at about nucleotides 97 through 99. Assuming that this ATG represents the initiation (start) codon and that nucleotides 1195 through about nucleotide 1197 of SEQ ID NO:1 represent the termination (stop) codon, then SEQ ID NO:1encodes a full-length *D. immitis* CP protein having an amino acid sequence of about 366 amino acids, denoted herein as $PDiCP_{366}$. That open reading frame is denoted herein as nucleic acid molecule $nDiCP_{1098}$ which spans from about nucleotide 97 through about nucleotide 1194 of SEQ ID NO:1.

Comparison of amino acid sequence SEQ ID NO:2 with amino acid sequences reported in GenBank indicates that the significant homology started at about amino acid 85 of SEQ ID NO:2, corresponding to an ATG codon in SEQ ID NO:1 spanning from about nucleotide 253 through about nucleotide 255. While not being bound by theory, this comparison suggests that the mature *D. immitis* cysteine protease is a protein of about 314 amino acids, denoted herein as $PDiCP_{314}$, which has the deduced amino acid sequence represented herein as SEQ ID NO:4. $PDiCP_{314}$ is encoded by a nucleic acid molecule of about 942 nucleotides, denoted herein as $nDiCP_{942}$, the nucleic acid sequence of which is represented herein as SEQ ID NO:3, which corresponds to a region spanning from about nucleotide 253 through about nucleotide 1194 of SEQ ID NO:1. Based on SEQ ID NO:4, $PDiCP_{314}$ has a calculated molecular weight of about 36.2 kD and an estimated pI of 9.36.

Additional sequence analyses of *D. immitis* L3 cysteine protease nucleic acid molecule $nDiCP_{1298}$ indicated that the nucleic acid molecule apparently included an extra six nucleotides—this nucleic acid molecule is hence referred to as $nDiCP_{1304}$. The nucleic acid sequence of nucleic acid molecule $nDiCP_{1304}$ is represented herein by SEQ ID NO:32 (the coding strand) and SEQ ID NO:35 (the complementary strand). SEQ ID NO:32 contains an apparent partial coding region, truncated at the 5' end.

Translation of SEQ ID NO:32 suggests that nucleic acid molecule $nDiCP_{1304}$ encodes about 400 amino acids of a *D. immitis* cysteine protease protein, which is referred to herein as $PDiCP_{400}$, assuming a first in-frame codon spanning from about nucleotide 1 through about nucleotide 3 and a stop codon spanning from about nucleotide 1201 through about nucleotide 1203 of SEQ ID NO:32. The deduced amino acid sequence of $PDiCP_{400}$ is represented as SEQ ID NO:33. Comparison of amino acid sequence SEQ ID NO:33 with amino acid sequences reported in GenBank indicates that SEQ ID NO:33 (in its entirety)is most closely homologous, at about 38 percent identity, to Bos taurus cathepsin L.

The nucleic acid molecule $nOvCP_{291}$ contains an open reading frame which is represented herein by SEQ ID NO:5. The open reading frame in $nOvCP_{291}$ (SEQ ID NO:5) extends from about the second nucleotide up to the stop codon beginning at about nucleotide 218 and encodes a protein of about 72 amino acids, denoted herein as $POvCP_{72}$, the deduced amino acid sequence of which is represented herein as SEQ ID NO:6. The coding region of $POvCP_{72}$ is encoded by the nucleic acid molecule $nOvCP_{216}$ which is represented herein as SEQ ID NO:7.

A composite nucleic acid sequence including an *O. volvulus* cysteine protease apparent full-length coding region, referred to herein as $nOvCP_{1306}$, was deduced using the nucleic acid sequence of $novCP_{291}$ and $nOvCP_{1272}$, and is denoted herein as SEQ ID NO:14 (the coding strand) and SEQ ID NO:30 (the complementary strand).

Translation of SEQ ID NO:14 suggests that nucleic acid molecule $nOvCP_{1306}$ encodes about 401 amino acids of a *O. volvulus* cysteine protease protein, which is referred to herein as $POvCP_{401}$, assuming an open reading frame spanning from about nucleotide 20 through about nucleotide 1222 of SEQ ID NO:14 with a first ATG codon spanning from about nucleotide 20 through about nucleotide 22 of SEQ ID NO:14 and a termination (stop) codon spanning from about nucleotide 1223 through about nucleotide 1225 of SEQ ID NO:14. The deduced amino acid sequence of $POvCP_{401}$ is represented herein as SEQ ID NO:17. Comparison of amino acid sequence SEQ ID NO:17 with amino acid sequences reported in GenBank indicates that SEQ ID NO:17 is about 44% identical over a region of about 330 amino acids to the amino acid sequence of the rabbit cathepsin K precursor. It is also to be noted that the amino acid sequence of *O. volvulus* cysteine protease protein $POvCP_{401}$ is about 49% identical to the coding region of *D. immitis* cysteine protease protein $PDiCP_{398}$.

Preferred filariid nematode CP proteins of the present invention also include: proteins comprising amino acid sequences that are at least about 40%, preferably at least about 60%, more preferably at least about 75% and even more preferably at least about 90% identical to amino acid sequence SEQ ID NO:4; proteins comprising amino acid sequences that are at least about 40%, preferably at least about 60%, more preferably at least about 75% and even more preferably at least about 90% identical to amino acid sequence SEQ ID NO:33; proteins comprising an amino acid sequences that are at least about 70%, more preferably at least about 75%, even more preferably at least about 80% and even more preferably at least about 90% identical to amino acid sequence SEQ ID NO:6; and proteins comprising an amino acid sequences that are at least about 45%, more preferably at least about 65%, even more preferably at least about 75% and even more preferably at least about 90% identical to amino acid sequence SEQ ID NO:17. More preferred filariid nematode CP proteins of the present invention include: proteins encoded by at least a portion of SEQ ID NO:1 and, as such, have amino acid sequences that include at least a portion of SEQ ID NO:2; proteins encoded by at least a portion of SEQ ID NO:32 and, as such, have amino acid sequences that include at least a portion of SEQ ID NO:33; proteins encoded by at least a portion of SEQ ID NO:5 and, as such, have amino acid sequences that include at least a portion of SEQ ID NO:6; and proteins encoded by at least a portion of SEQ ID NO:14 and, as such, have amino acid sequences that include at least a portion of SEQ ID NO:15.

Particularly preferred filariid nematode CP proteins of he present invention are proteins that include SEQ ID NO:2, SEQ ID NO:4, SEQ ID NO:6, SEQ ID NO:15, SEQ ID NO:17, SEQ ID NO:33, and/or SEQ ID NO:38 (including, but not limited to the encoded proteins, full-length proteins, processed proteins, fusion proteins and multivalent proteins) as well as proteins that are truncated homologues of proteins that include SEQ ID NO:2, SEQ ID NO:4, SEQ ID NO:6, SEQ ID NO:15, SEQ ID NO:17, SEQ ID NO:33, and/or SEQ ID NO:38. Even more preferred proteins include $PDiCP_{398}$, $PDiCP_{366}$, $PDiCP_{314}$, $PDiCP_{400}$, $PDiCP_{386}$, $PDCP_{382}$, $PDiCP_{215}$, $PDiCP_{236}$, $PPLA2-PDiCP_{241}$, $PHIS-PDiCP_{314}$, $PDiCP_{356}$, $PHIS-PDiCP_{945}$, $POvCP_{72}$, $POvCP_{401}$ and $PHIS-POvCP_{1203}$. Examples of methods to produce such proteins are disclosed herein, including in the Examples section.

Another embodiment of the present invention is an isolated filariid nematode nucleic acid molecule that hybridizes under stringent hybridization conditions with a gene selected from the group consisting of a D. immitis L3 larval cysteine protease gene and an O. volvulus L3 larval cysteine protease gene. The identifying characteristics of such genes are heretofore described. A nucleic acid molecule of the present invention can include an isolated natural filariid nematode CP gene or a homologue thereof, the latter of which is described in more detail below. A nucleic acid molecule of the present invention can include one or more regulatory regions, full-length or partial coding regions, or combinations thereof. The minimal size of a nucleic acid molecule of the present invention is the minimal size that can form a stable hybrid with one of the aforementioned genes under stringent hybridization conditions. Suitable and preferred filariid nematodes are disclosed above.

In accordance with the present invention, an isolated nucleic acid molecule is a nucleic acid molecule that is not in its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated filariid nematode CP nucleic acid molecule of the present invention can be obtained from its natural source either as an entire (i.e., complete) gene or a portion thereof capable of forming a stable hybrid with that gene. An isolated filariid nematode CP nucleic acid molecule can also be produced using recombinant DNA technology (e.g., polymerase chain reaction (PCR) amplification, cloning) or chemical synthesis. Isolated filariid nematode CP nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a filariid nematode CP protein of the present invention or to form stable hybrids under stringent conditions with natural gene isolates.

A filariid nematode CP nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., ability to elicit an immune response against at least one epitope of a filariid nematode CP protein) and/or by hybridization with a D. immitis CP gone and/or with an O. volvulus CP gene.

An isolated nucleic acid molecule of the present invention can include a nucleic acid sequence that encodes at least one filariid nematode CP protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a filariid nematode CP protein. As heretofore disclosed, filariid nematode CP proteins of the present invention include, but are not limited to, proteins having full-length filariid nematode CP coding regions, proteins having partial filariid nematode CP coding regions, fusion proteins, multivalent protective proteins and combinations thereof.

A preferred nucleic acid molecule of the present invention, when administered to an animal, is capable of protecting that animal from disease caused by a parasitic helminth. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein, the nucleic acid molecule being delivered to the animal by direct injection (i.e, as a naked nucleic acid) or in a vehicle such as a recombinant virus vaccine or a recombinant cell vaccine.

One embodiment of the present invention is a filariid nematode CP nucleic acid molecule that hybridizes under stringent hybridization conditions with the nucleic acid molecule $nDiCP_{1298}$, the nucleic acid molecule $nDiCP_{1304}$, the nucleic acid molecule $nOvCP_{291}$, and/or with the nucleic acid molecule $nOvCP_{1306}$. The deduced nucleic acid sequence of $nDiCP_{1298}$ is represented herein as SEQ ID NO:1, the deduced nucleic acid sequence of $nDiCP_{1304}$ is represented herein as SEQ ID NO:32, the deduced nucleic acid sequence of nOvCP$_{291}$ is represented herein as SEQ ID NO:5, and the deduced nucleic acid sequence of nOvCP$_{1306}$ is represented herein as SEQ ID NO:14. An open reading frame contained in nDiCP$_{1298}$ is similar to that of known cysteine proteases and is referred to herein as nDiCP$_{942}$, the nucleic acid sequence of which is represented by SEQ ID NO:3. The open reading frame contained in nDiCP$_{1304}$, referred to herein as nDiCP$_{1200}$, is represented by SEQ ID NO:34. The open reading frame contained in nOvCP$_{291}$, referred to herein as nOvCP$_{216}$, is represented by SEQ ID NO:7. The open reading frame contained in nOvCP$_{1306}$, referred to herein as nOvCP$_{1203}$, is represented by SEQ ID NO:16.

A preferred nucleic acid molecule of the present invention includes at least a portion of nucleic acid sequence SEQ ID NO:1, SEQ ID NO:5, SEQ ID NO:14, SEQ ID NO:26, SEQ ID NO:28, SEQ ID NO:30, SEQ ID NO:32 and/or SEQ ID NO:35 that is capable of hybridizing to a *D. immitis* CP gene and/or to a *O. volvulus* CP gene of the present invention. More preferred is a nucleic acid molecule that includes nucleic acid sequence SEQ ID NO:1, SEQ ID NO:3, SEQ ID NO:5, SEQ ID NO:7, SEQ ID NO:14, SEQ ID NO:16, SEQ ID NO:26, SEQ ID NO:27, SEQ ID NO:28, SEQ ID NO:29, SEQ ID NO:30, SEQ ID NO:31, SEQ ID NO:32, SEQ ID NO:34, SEQ ID NO:35, SEQ ID NO:36, SEQ ID NO:37, SEQ ID NO:39 or allelic variants thereof. Such a nucleic acid molecule can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound. Particularly preferred nucleic acid molecules include nDiCP$_{1298}$, nDiCP$_{1194}$, nDiCP$_{1098}$, nDiCP$_{942}$, nDiCP$_{945}$, nDiCP$_{850}$, nDiCP$_{450}$, nDiCP$_{1071}$, nDiCP$_{1304}$, nDiCP$_{1158}$, nDiCP$_{1145}$, nDiCP$_{1200}$, nDiCP$_{645}$, nDiCP$_{1206}$ nOvCP$_{291}$, nOvCP$_{216}$, nOvCP$_{1306}$, nOvCP$_{1272}$ or nOvCP$_{1203}$.

The present invention also includes nucleic acid molecules encoding a protein having at least a portion of SEQ ID NO:2, nucleic acid molecules encoding a protein having at least a portion of SEQ ID NO:4, nucleic acid molecules encoding a protein having at least a portion of SEQ ID NO:6, nucleic acid molecules encoding a protein having at least a portion of SEQ ID NO:15, nucleic acid molecules encoding a protein having at least a portion of SEQ ID NO:22, nucleic acid molecules encoding a protein having at least a portion of SEQ ID NO:25, nucleic acid molecules encoding a protein having at least a portion of SEQ ID NO:17, nucleic acid molecules encoding a protein having at least a portion of SEQ ID NO:33, and nucleic acid molecules encoding a protein having at least a portion of SEQ ID NO:38, including nucleic acid molecules that have been modified to accommodate codon usage properties of the cells in which such nucleic acid molecules are to be expressed.

Knowing the nucleic acid sequences of certain filariid nematode CP nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain CP nucleic acid molecules for other filariid nematodes, particularly since, as described in detail in the Examples section, knowledge of *D. immitis* CP nucleic acid molecules of the present invention enabled the isolation of *O. volvulus* CP nucleic acid molecules of the present invention. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify nucleic acid molecule include parasitic helminth L3 larval libraries as well as genomic DNA libraries. Similarly, preferred DNA sources to screen or from which to amplify nucleic acid molecules include parasitic helminth L3 larval DNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising filariid nematode CP genes or other filariid nematode CP nucleic acid molecules. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit CP protein production or activity. Such therapeutic applications include the use of such oligonucleotides in, for example, antisense-, triplex formation-, ribozyme- and/or RNA drug-based technologies. The present invention, therefore, includes such oligonucleotides and methods to protect animals from disease caused by parasitic helminths by use of one or more of such technologies. Appropriate oligonucleotide-containing therapeutic compositions can be administered to an animal, using techniques known to those skilled in the art, either prior to or after infection by a parasitic helminth such as *D. immitis* or *O. volvulus* in order to protect the animal from disease.

The present invention also includes a recombinant vector, which includes at least one filariid nematode CP nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule (s) are derived. The vector can be either RNA or DNA, either prokaryotic or eukaryotic, and typically is a virus or a plasmid. Recombinant vectors can be used in the cloning, sequencing, and/or otherwise manipulating of filariid nematode CP nucleic acid molecules of the present invention. One type of recombinant vector, referred to herein as a recombinant molecule and described in more detail below, can be used in the expression of nucleic acid molecules of the present invention. Preferred recombinant vectors are capable of replicating in the transformed cell.

Suitable and preferred nucleic acid molecules to include in recombinant vectors of the present invention are as disclosed herein for suitable and preferred filariid nematode CP nucleic acid molecules per se. Particularly preferred nucleic acid molecules to include in recombinant vectors, and particularly in recombinant molecules, of the present invention include $nDiCP_{1298}$, $nDiCP_{1194}$, $nDiCP_{1098}$, $nDiCP_{942}$, $nDiCP_{945}$, $nDiCP_{850}$, $nDiCP_{450}$, $nDiCP_{1071}$, $nDiCP_{1304}$, $nDiCP_{1158}$, $nDiCP_{1145}$, $nDiCP_{1200}$, $nDiCP_{645}$, $nDiCP_{1206}$, $nOvCP_{291}$, $nOvCP_{216}$, $nOvCP_{1306}$, $nOvCP_{1272}$ and $nOvCP_{1203}$.

Isolated filariid nematode CP proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell that is capable of expressing the protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable and preferred nucleic acid molecules with which to transform a cell are as disclosed herein for suitable and preferred filariid nematode CP nucleic acid molecules per se. Particularly preferred nucleic acid molecules to include in recombinant cells of the present invention include $nDiCP_{1298}$, $nDiCP_{1194}$, $nDiCP_{1098}$, $nDiCP_{942}$, $nDiCP_{945}$, $nDiCP_{850}$, $nDiCP_{4501}$, $nDiCP_{1071}$, $nDiCP_{1304}$, $nDiCP_{1158}$, $nDiCP_{1145}$, $nDiCP_{1200}$, $nDiCP_{645}$, $nDiCP_{1206}$, $nOvCP_{291}$, $nOvCP_{216}$, $nOvCP_{1306}$, $nOvCP_{1272}$ and $nOvCP_{1203}$.

Suitable host cells to transform include any cell that can be transformed with a nucleic acid molecule of the present invention. Host cells can be either untransformed cells or cells that are already transformed with at least one nucleic acid molecule. Host cells of the present invention either can be endogenously (i.e., naturally) capable of producing filariid nematode CP proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), insect, other animal and plant cells. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi*; *Salmonella typhimurium*, including attenuated strains such as UK-1$_x$3987 and SR-11$_x$4072; *Spodoptera frugiperda*; Trichoplusia ni; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, helminth or other parasite, insect and mammalian cells and more preferably in the cell types heretofore disclosed.

Recombinant molecules of the present invention may also (a) contain secretory signals (i.e., signal segment nucleic acid sequences) to enable an expressed filariid nematode CP protein of the present invention to be secreted from the cell that produces the protein and/or (b) contain fusion sequences which lead to the expression of nucleic acid molecules of the present invention as fusion proteins. Examples of suitable signal segments and fusion segments encoded by fusion segment nucleic acids are disclosed herein. Eukaryotic recombinant molecules may include intervening and/or untranslated sequences surrounding and/or within the nucleic acid sequences of nucleic acid molecules of the present invention.

Suitable signal segments include natural signal segments or any heterologous signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments.

Nucleic acid molecules of the present invention can be operatively linked to expression vectors containing regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other parasite, insect and mammalian cells, such as, but not limited to, tac, lac, trp, trc, oxy-pro, omp/lpp, rrnB, bacteriophage lambda (such as lambda $P_L$ and lambda $P_R$ and fusions that include such promoters), bacteriophage T7, T71ac, bacteriophage T3, bacteriophage SP6, bacteriophage SPO1, metallothionein, alpha-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, poxvirus, adenovirus, cytomegalovirus (such as intermediate early promoters, simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a filariid nematode nucleic acid molecule, such as a *D. immitis* or *O. volvulus* molecule prior to isolation.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. Particularly preferred recombinant molecules include, pβgal-nDiCP$_{1298}$, pHis-nDiCP$_{945}$, pVL1393-nDiCP$_{945}$, pVL1392-nDiCP$_{1206}$, pVL1393/PLA2-nDiCP$_{645}$, nPLA2-nDiCP$_{726}$, vBV-nDiCP$_{9451}$, vBV-nDiCP$_{1206}$, vBV-nDiCP$_{645}$, pkB3poly-nDiCP$_{1071}$, Rcn-nDiCP$_{1071}$, p11-nDiCP$_{1071}$/pSyn-nDiPLA2$_{453}$, Rcn-nDiCP$_{1071}$-nDiPLA2$_{453}$, pCMV-nDiCP$_{1071}$, pBSC-nDiCP$_{356}$, and pHis-nOvCP$_{1203}$. Details regarding the production of *D. immitis* and *O. volvulus* CP nucleic acid molecule-containing recombinant molecules are disclosed herein.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein. Particularly preferred recombinant cells include *E. coli*:pHis-nDiCP$_{945}$, *S. frugiperda*:pVL1393-nDiCP$_{945}$, *S. frugiperda*:pVL1392-nDiCP$_{1206}$, *S. frugiperda*:pVL1393/PLA2-nDiCP$_{645}$, BSC1:pKB3poly-nDiCP$_{1071}$, BHK:pCMV-nDiCP$_{1071}$ BSC1:p11-nDiCP$_{1071}$/pSyn-nDiPLA2$_{453}$ and *E. Coli*:pHis-nOvCP$_{1203}$. Details regarding the production of these recombinant cells are disclosed herein.

Recombinant cells of the present invention can also be co-transformed with one or more recombinant molecules including filariid nematode CP nucleic acid molecules encoding one or more proteins of the present invention and one or more other proteins useful in the production of multivalent vaccines which can include one or more protective compounds.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

In accordance with the present invention, recombinant cells of the present invention can be used to produce one or more proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a filariid nematode CP protein of the present invention. Such a medium is typically an aqueous medium comprising assimilable carbon, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein" refers simply to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and should be capable of stimulating the production of antibodies in a treated animal.

The present invention also includes isolated antibodies capable of selectively binding to a filariid nematode CP protein of the present invention or to a mimetope thereof. Such antibodies are also referred to herein as anti-filariid nematode CP antibodies. Particularly preferred antibodies of this embodiment include anti-*D. immitis* CP antibodies and anti-*O. volvulus* CP antibodies.

Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees.

As used herein, the term "selectively binds to" refers to the ability of antibodies of the present invention to preferentially bind to specified proteins and mimetopes thereof of the present invention. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, for example, Sambrook et al., ibid. An anti-filariid nematode CP antibody preferably binds to a filariid nematode CP protein in such a way as to reduce the activity of that protein.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Antibodies of the present invention also include chimeric antibodies that can bind to more than one epitope. Preferred antibodies are raised in response to proteins, or mimetopes thereof, that are encoded, at least in part, by a nucleic acid molecule of the present invention.

A preferred method to produce antibodies of the present invention includes (a) administering to an animal an effective amount of a protein or mimetope thereof of the present invention to produce the antibodies and (b) recovering the antibodies. In another method, antibodies of the present invention are produced recombinantly using techniques as heretofore disclosed to produce filariid nematode CP proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from parasitic helminths susceptible to treatment by such antibodies, (b) as reagents in assays to detect infection by such filariid nematodes and/or (c) as tools to screen expression libraries and/or to recover desired proteins of the present invention from a mixture of proteins and other contaminants. Furthermore, antibodies of the present invention can be used to target cytotoxic agents to parasitic helminths of the present invention in order to directly kill such helminths. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from disease caused by a parasitic helminth. Therapeutic compositions of the present invention include at least one of the following protective compounds: (a) an isolated filariid nematode L3 larval cysteine protease protein or a mimetope thereof; (b) an isolated filariid nematode nucleic acid molecule that hybridizes under stringent hybridization conditions with a *D. immitis* L3 larval cysteine protease gene and/or an *O. volvulus* L3 larval cysteine protease gene; (c) an isolated antibody that selectively binds to a filariid nematode L3 larval cysteine protease rrotein; (d) an inhibitor of cysteine protease activity identified by its ability to inhibit filariid nematode L3 larval cysteine protease activity; and (e) a mixture (i.e., combination) of at least two of the compounds. As used herein, a protective compound refers to a compound that, when administered to an animal in an effective manner, is able to treat, ameliorate, and/or prevent disease caused by a parasitic helminth of the present invention. Suitable helminths to target include a parasite comprises a tissue-migrating helminth. Preferred helminths to target include, for example, nematodes, cestodes and trematodes. More preferred helminths to target include, for example, filariid, ascarid, strongyle and trichostrongyle nematodes. Even more preferred helminths to target include, for example, nematodes of the genera Acanthocheilonema, Aelurostrongylus, Ancylostoma, Angiostrongylus, Ascaris, Brugia, Bunostomum, Dictyocaulus, Dioctophyme, Dipetalonema, Dirofilaria, Dracunculus, Filaroides, Lagochilascaris, Loa, Mansonella, Muellerius, Necator, Onchocerca, Parafilaria, Parascaris, Protostrongylus, Setaria, Stephanofilaria, Strongyloides, Strongylus, Thelazia, Toxascaris, Toxocara, Trichinella, Uncinaria and Wuchereria. Other particularly preferred parasitic helminths include nematodes of the genera Capillaria, Chabertia, Cooperia, Enterobius, Haemonchus, Nematodirus, Oesophagostomum, ostertagia, Trichostrongylus and Trichuris. Particularly preferred nematodes include Dirofilaria, Onchocerca, Acanthocheilonema, Brugia, Dipetalonema, Loa, Parafilaria, Setaria, Stephanofilaria and Wuchereria filariid nematodes, with Dirofilaria and Onchocerca being more preferred. Examples of proteins, nucleic acid molecules and antibodies of the present invention are disclosed herein.

The present invention also includes a therapeutic composition comprising at least one filariid nematode CP-based compound of the present invention in combination with at least one additional compound protective against one or more infectious agents. Examples of such compounds and infectious agents are disclosed herein.

Therapeutic compositions of the present invention can be administered to any animal susceptible to such therapy, preferably to mammals, and more preferably to dogs, cats, humans, ferrets, horses, cattle, sheep and other pets, economic food animals and/or zoo animals. Preferred animals to protect against heartworm include dogs, cats, humans and ferrets, with dogs and cats being particularly preferred. Preferred animals to protect against onchocerciasis include humans, cattle and horses, with humans being particularly preferred.

In one embodiment, a therapeutic composition of the present invention can be administered to the vector in which the parasitic helminth develops, such as to a mosquito in order to prevent the spread of heartworm or to a black fly in order to prevent the spread of onchocerciasis. Such administration could be orally or by developing transgenic vectors capable of producing at least one therapeutic composition of the present invention. In another embodiment, a vector, such as a mosquito or a black fly, can ingest therapeutic compositions present in the blood of a host that has been administered a therapeutic composition of the present invention.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the therapeutic composition can also include an immunopotentiator, such as an adjuvant or a carrier. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax™ adjuvant (Vaxcel™, Inc. Norcross, Ga.) Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a composition of the present invention into an animal. As used herein, a controlled re ease formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioredible).

A preferred controlled release formulation of the present invention is capable of releasing a composition of the present invention into the blood of the treated animal at a constant rate sufficient to attain therapeutic dose levels of the composition to protect an animal from disease caused by parasitic helminths. The therapeutic composition is preferably released over a period of time ranging from about 1 to about 12 months. A controlled release formulation of the present invention is capable of effecting a treatment for preferably at least about 1 month, more preferably at least about 3 months and even more preferably for at least about 6 months, even more preferably for at least about 9 months, and even more preferably for at least about 12 months.

In order to protect an animal from disease caused by a parasitic helminth of the present invention, a therapeutic composition of the present invention is administered to the animal in an effective manner such that the composition is capable of protecting that animal from a disease caused by a parasitic helminth. For example, an isolated protein or mimetope thereof, when administered to an animal in an effective manner, is able to elicit (i.e., stimulate) an immune response, preferably including both a humoral and cellular response, that is sufficient to protect the animal from the disease. Similarly, an antibody of the present invention, when administered to an animal in an effective manner, is administered in an amount so as to be present in the animal at a titer that is sufficient to protect the animal from the disease, at least temporarily. Oligonucleotide nucleic acid molecules of the present invention can also be administered in an effective manner, thereby reducing expression of filariid nematode CP proteins in order to interfere with development of parasitic helminths targeted in accordance with the present invention.

Therapeutic compositions of the present invention can be administered to animals prior to infection in order to prevent infection and/or can be administered to animals after infection in order to treat disease caused by the parasitic helminth. For example, proteins, mimetopes thereof, and antibodies thereof can be used as immunotherapeutic agents.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster vaccinations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme or RNA drug) in the animal to be protected from disease. Nucleic acid molecules can be delivered to an animal in a variety of methods including, but not limited to, (a) administering a naked (i.e., not packaged in a viral coat or cellular membrane) nucleic acid vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A naked nucleic acid vaccine of the present invention includes a nucleic acid molecule of the present invention and preferably includes a recombinant molecule of the present invention that preferably is replication, or otherwise amplification, competent. Such a vaccine can comprise any nucleic acid molecule or recombinant molecule of the present invention. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid vaccines of the present invention can be administered in a variety of ways, with intramuscular, subcutaneous, intradermal, transdermal, intranasal and oral routes of administration being preferred. A preferred single dose of a naked nucleic acid vaccine ranges from about 1 nanogram (ng) to about 100 μg, depending on the route of administration and/or method of delivery, as can be determined by those skilled in the art. Suitable delivery methods include, for example, by injection, as drops, aerosolized and/or topically. Suitable excipients include, for example, physiologically acceptable aqueous solutions (e.g., phosphate buffered saline as well as others disclosed above), liposomes (including neutral or cationic liposomes), and other lipid minembrane-based vehicles (e.g., micelles or cellular membranes).

A recombinant virus vaccine of the present invention includes a recombinant molecule of the present invention that is packaged in a viral coat and that can be expressed in an animal after administration. Preferably, the recombinant molecule is packaging-deficient. A number of recombinant viruses can be used, including, but not limited to, those based on alphaviruses, poxviruses, adenoviruses, herpesviruses, and retroviruses. Preferred recombinant virus vaccines are those based on alphaviruses (such as Sindbis virus), species-specific herpesviruses and species-specific poxviruses. Methods to produce and use recombinant virus vaccines are disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from disease caused by a parasitic helminths as disclosed herein. For example, a recombinant virus vaccine comprising a *D. immitis* CP nucleic acid molecule of the present invention is administered according to a protocol that results in the animal producing a sufficient immune response to protect itself from heartworm. A preferred single dose of a recombinant virus vaccine of the present invention is from about $1\times10^4$ to about $1\times10^7$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include *Salmonella, E. coli, Listeria, Mycobacterium, S. frugiperda*, BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells or cell lysates.

The efficacy of a therapeutic composition of the present invention to protect an animal from disease caused by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth to determine whether the treated animal is resistant to disease. Such techniques are known to those skilled in the art.

One preferred embodiment of the present invention is the use of filariid nematode CP proteins, nucleic acid molecules and antibodies of the present invention, and particularly *D. immitis* CP proteins, nucleic acid molecules and antibodies of the present invention, to protect an animal from heartworm. Preferred therapeutic compositions are those that are able to inhibit at least one step in the portion of the parasite's development cycle that includes L3 larvae, third molt, L4 larvae, fourth molt and immature adult prior to entering the circulatory system. In dogs, this portion of the development cycle is about 70 days. Particularly preferred therapeutic compositions include *D. immitis*-based therapeutic compositions of the present invention. Such compositions are administered to animals in a manner effective to protect the animals from heartworm. Additional protection may be obtained by administering additional protective compounds, including other *D. immitis* proteins, nucleic acid molecules and antibodies.

Another preferred embodiment of the present invention is the use of filariid nematode CP proteins, nucleic acid molecules and antibodies of the present invention, and particularly *O. volvulus* CP proteins, nucleic acid molecules and antibodies of the present invention, to protect a human from onchocerciasis. Preferred therapeutic compositions are those that are able to inhibit at least one step in the portion of the parasite's development cycle that includes L3 larvae, third molt, L4 larvae, fourth molt and immature adult prior to entering the subcutaneous tissues. In humans infected with *O. volvulus*, this portion of the development cycle is about 150 days. Particularly preferred therapeutic compositions include *O. volvulus*-based therapeutic compositions of the present invention. Such compositions are administered to humans in a manner effective to protect the treated humans from onchocerciasis. Additional protection may be obtained by administering additional protective compounds, including other Onchocerca, preferably *O. volvulus*, proteins, nucleic acid molecules and antibodies.

An inhibitor of cysteine protease activity can be identified using parasitic helminth, and preferably *D. immitis* and/or *O. volvulus* CP proteins of the present invention. One embodiment of the present invention is a method to identify a compound capable of inhibiting cysteine protease activity of a parasitic helminth. Such a method includes the steps of (a) contacting (e.g., combining, mixing) an isolated filariid nematode CP protein with a putative inhibitory compound under conditions in which, in the absence of the compound, the protein has cysteine protease activity, and (b) determining if the putative inhibitory compound inhibits the cysteine protease activity. Putative inhibitory compounds to screen include organic molecules, antibodies (including mimetopes thereof) and substrate analogs. Methods to determine cysteine protease activity are known to those skilled in the art.

It is also within the scope of the present invention to use isolated proteins, mimetopes, nucleic acid molecules and antibodies of the present invention as diagnostic reagents to detect infection by parasitic helminths. Such diagnostic reagents can be supplemented with additional compounds that can detect other phases of the parasite's life cycle.

The following examples are provided for the purposes of illustration and are not intended to limit the scope of the present invention.

EXAMPLES

Example 1

This Example describes the cloning and sequencing of a filariid nematode cysteine protease nucleic acid molecule of the present invention.

A *D. immitis* cysteine protease nucleic acid molecule of about 1298 nucleotides, denoted $nDiCP_{1298}$, was identified by its ability to encode a protein that selectively bound to at least one component of immune serum collected from a dog immunized with chemically abbreviated *D. immitis* larval infections in the following manner. A *D. immitis* cDNA expression library was constructed in Uni-ZAP™ XR vector (available from Stratagene Cloning Systems, La Jolla, Calif.), using Stratagene's ZAP-cDNA Synthesis Kit protocol and third stage larval mRNAs. Using the protocol described in the Stratagene picoBlue immunoscreening kit, the L3 larval cDNA expression library was screened with immune dog sera. The production and use of immune dog serum to identify heartworm vaccine candidates is disclosed in PCT Publication No. WO 92/13560, published Aug. 20, 1992.

Immunoscreening of duplicate plaque lifts of the cDNA library with the same immune dog serum identified the nucleic acid molecule $nDiCP_{1298}$. The plaque-purified clone including $nDiCP_{1298}$ was converted into a double-stranded plasmid using ExAssist™ helper phage and SOLR™ *E. coli* according to the in vivo excision protocol described in the Stratagene ZAP-cDNA Synthesis Kit. Double-stranded plasmid DNA was prepared using an alkaline lysis protocol, such as that described in Sambrook et al., ibid. The double-stranded plasmid containing the fragment is denoted herein as recombinant molecule pβgal-$nDiCP_{1298}$. The plasmid DNA was digested with EcoRI and XhoI restriction endonucleases. The digestion released two *D. immitis* DNA fragments of about 450 and about 848 nucleotides from the $nDiCP_{1298}$ nucleic acid molecule. As described in more detail below, nucleic acid molecule $nDiCP_{1298}$ has been shown to encode a cysteine protease protein. Pursuant to 37 CFR § 1.802 (a–c), SOLR™ *E. coli* comprising recombinant molecule pβgal-$nDiCP_{1298}$, designated herein as *E. coli*:pβgal-$nDiCP_{1298}$, was deposited with the American Type Culture Collection (ATCC, 12301 Parklawn Drive, Rockville, Md., 20852) under the Budapest Treaty as ATCC Accession No. ATCC 98471 on Jun. 18, 1997. Pursuant to 37 CFR § 1.806, the deposit is made for a term of at least thirty (30) years and at least five (5) years after the most recent request for the furnishing of a sample of the deposit was received by the depository. Pursuant to 37 CFR § 1808 (a) (2), all restrictions imposed by the depositor on the availability to the public will be irrevocably removed upon the granting of the patent.

Nucleic acid molecule $nDiCP_{1298}$ was sequenced using the Sanger dideoxy chain termination method, as described in Sambrook et al., ibid. An about 1298 nucleotide consensus sequence of the entire $nDiCP,_{1298}$ nucleic acid molecule was determined and is denoted herein as SEQ ID No:1. The nucleic acid sequence SEQ ID NO:1includes an open reading frame spanning from about nucleotide 1 through about nucleotide 1194, with a first ATG codon spanning from about nucleotide 97 through about nucleotide 99 and a termination (stop) codon spanning from about nucleotide 1195 through about 1197. A putative polyadenylation signal (5' AATAAA 3') is located from about nucleotide 1265 through about nucleotide 1270. The amino terminus of the nucleic acid sequence represented by SEQ ID NO:1 encodes a hydrophobic region as determined using a standard hydrophilicity plot.

The open reading frame extending from the first nucleotide of $nDiCP_{1298}$ up to the stop codon is a nucleic acid molecule of about 1194 nucleotides, denoted herein as $nDiCP_{1194}$, which encodes a protein of about 398 amino acids, denoted herein as $PDiCP_{398}$ the deduced amino acid sequence of which is represented herein as SEQ ID NO:2. Assuming that the ATG located from about nucleotide 97 through about nucleotide 99 represents the initiation (start) codon, SEQ ID NO:1 encodes a protein having an amino acid sequence of about 366 amino acids, denoted herein as $PDiCP_{366}$. That open reading frame is denoted herein as nucleic acid molecule $nDiCP_{1098}$ and spans from about nucleotide 97 through about nucleotide 1194 of SEQ ID NO:1. Assuming that the ATG located from about nucleotide 127 through about nucleotide 129 represents the initiation codon, SEQ ID NO:1 encodes a protein having an amino acid sequence of about 356 amino acids, denoted herein as $PDiCP_{356}$. That open reading frame is denoted herein as nucleic acid molecule $nDiCP_{1068}$ and spans from about nucleotide 127 through about nucleotide 1194 of SEQ ID NO:1. Assuming that the ATG located from about nucleotide 253 through about nucleotide 255 represents the initiation codon, SEQ ID NO:1 encodes a protein having an amino acid sequence of about 314 amino acids, denoted herein as $PDicP_{314}$. That open reading frame is denoted herein as nucleic acid molecule $nDiCP_{942}$ and spans from about nucleotide 253 through about nucleotide 1194 of SEQ ID NO:1.

The very highly conserved catalytic residues of members of the papain family of cysteine peptidases are a cysteine at amino acid position 25 (C25) and a histidine residue at position 159 (H159) of the mature, processed peptide. Other amino acid residues important for catalysis include a glutamine at position 19 (Q19) and asparagine at position 175 (N175). The numbering of these amino acids correspond to the amino acid position of the mature papain sequence (Genbank Acc. No. M15203).

Based on a homology alignment of the PDICP$_{356}$ deduced amino acid sequence with known papain amino acid sequences, the predicted mature protein resulting from the processing of the PDiCP$_{356}$ sequence, referred to as PDiCP$_{213}$ (SEQ ID NO:22), would begin with the leucine at residue 144 of PDiCP$_{356}$. PDiCP$_{213}$ also contains the papain family conserved residues believed to be involved in catalysis, namely, a cysteine at residue 25 (C25), a histidine at residue 160 which corresponds to the H159 of papain, a glutamine at position 19 (Q19) and an asparagine at residue 181 which corresponds to the N175 of papain. In addition, many members of the papain C1 family contain a proline residue at position 2 of the mature, processed enzyme. The PDiCP$_{213}$ amino acid sequence has a proline at position 2 of the predicted mature enzyme.

To confirm the *D. immitis* origin of the isolated L3 cysteine protease cDNA nucleic acid molecules, a Southern blot containing about 10 micrograms of EcoRI restricted *D. immitis* genomic DNA and Aedes aegypti genomic DNA was hybridized under stringent conditions with pβgal-nDiCP$_{1298}$ DNA radiolabeled by random priming with the Megaprime DNA Labeling System (available from Amersham Life Science, Arlington Heights, Ill.). The probe detected two bands of about 2500 and 700 nucleotides only in the *D. immitis* genomic DNA.

A homology search of the non-redundant protein sequence database was performed through the National Center for Biotechnology Information using the BLAST network. This database includes+SwissProt+PIR+SPUpdate+GenPept+GPUpdate. SEQ ID NO:2 was found to have significant homology to certain cysteine proteases starting at about amino acid 85 of SEQ ID NO:2, corresponding to an ATG codon in SEQ ID NO:1 spanning from about nucleotide 253 through about nucleotide 255. While not being bound by theory, this comparison suggests that the mature *D. immitis* cysteine protease is a protein of about 314 amino acids, denoted herein as PDiCP$_{3141}$ which has the deduced amino acid sequence represented herein as SEQ ID NO:4. PDiCP$_{314}$ is encoded by a nucleic acid molecule of about 942 nucleotides, denoted herein as nDiCP$_{942}$, the nucleic acid sequence of which is represented herein as SEQ ID NO:3, which corresponds to a region spanning from about nucleotide 253 through about nucleotide 1194 of SEQ ID NO:1. Based on SEQ ID NO:4, PDiCP$_{314}$ has a calculated molecular weight of about 36.2 kD and an estimated pI of about 9.36.

SEQ ID NO:4 was found to be about 37% identical to Norway lobster cathepsin L (Genbank Acc. No. S47433); about 30% identical to Dictyostelium discoideum cysteine proteinase 2 (Acc. No. X03344); about 39% identical to Sarcophaga peregrina pro-cathepsin (Acc. No. LD16533); about 36% identical to Fasciola hepatica cathepsin L-like proteinases (Acc. No. S43991); about 35% identical to Fasciola hepatica cathepsin (Acc. No. L33772); about 36% identical to *Schistosoma mansoni* cathepsin L (Acc. No. S44151): about 36% identical to Fasciola hepatica cathepsin L-like protease (Acc. No. Z22765); about 30% identical to *Trichomonas vaginalis* putative cysteine proteinase (Acc. No. X77221); about 35% identical to *Entamoeba histolytica* cysteine proteinase (Acc. No. A23705); and about 28% identical to *Trichomonas vaginalis* cysteine proteinase (Acc. No. S41427).

The corresponding region of SEQ ID NO:4 is also about 23% identical to the deduced amino acid sequence of the *D. immitis* amplified genomic PCR fragment nDiCP$_{143}$ disclosed in PCT Patent Publication No. WO 95/32988, published Dec. 7, 1995, which is incorporated by reference herein in its entirety.

The nucleic acid sequence represented by SEQ ID NO:1 was found to be about 48.4% identical to C. papaya mRNA for chymopapain (Genbank Acc. No. X97789); about 44.7% identical to Fasciola hepatica cathepsin L-like proteinase (Genbank Acc. No. L33771); and about 42.2% identical to *Schistosoma mansoni* mRNA for cathepsin L (Genbank Acc. No. Z32529).

Example 2

This example discloses the production of a recombinant cell of the present invention.

Recombinant molecule pHis-nDiCP$_{945}$ containing *D. immitis* L3 cysteine protease nucleic acid molecule nDiCP$_{945}$ operatively linked to trc transcription control sequences and to a fusion sequence encoding a polyhistidine segment comprising 6 histidines, was produced in the following manner. An about 945 nucleotide DNA fragment containing nucleotides spanning from about nucleotide 253 through about nucleotide 1197 of SEQ ID NO:1, called nDiCP$_{945}$, was polymerase chain reaction (PCR) amplified from recombinant molecule pβgal-nDiCP$_{1298}$, described in Example 1, using the following primers: primers CP sen 5' AACGGTGAGGATCCAGCGAT-GAAAAAATTAGAAAC 3' (SEQ ID NO:8) (BamHI site in bold) and CP ant 5' ATTAAAAGATCTTTATATGGG-GAATGAAGCCATCG 3' (SEQ ID NO:9) (BglHI site in bold). The PCR product was digested with BamHI and BglII restriction endonucleases, gel purified and subcloned into expression vector pTrcHisB (available from InVitrogen, San Diego, Calif.) that had been digested with BamHI. The resulting recombinant molecule pHis-nDiCP$_{945}$ was transformed into *E. coli* to form recombinant cell *E. coli*:pHis-nDiCP$_{945}$.

Example 3

This Example describes the production in bacteria of a filariid nematode cysteine protease protein of the present invention. This Example also discloses an antibody preparation produced in response to the parasitic helminth protein.

Recombinant cell *E. coli*:pHis-nDiCP$_{945}$, produced as described in Example 2, was cultured in shake flasks containing an enriched bacterial growth medium containing 0.1 mg/ml ampicillin and 0.1% glucose at about 32° C. When the cells reached an OD$_{600}$ of about 0.4, expression of *D. immitis* nDiCP$_{945}$ was induced by addition of about 0.5 mM isopropyl-β-D-thiogalactoside (IPTG), and the cells cultured for about 3 hours at about 32° C. Protein production was monitored by SDS PAGE of recombinant cell lysates, followed by Coomassie blue staining, using standard techniques. Recombinant cell *E. coli*:pHis-nDiCP$_{945}$ produced a fusion protein, denoted herein as PHIS-PDiCP$_{314}$, that migrated with an apparent molecular weight of about 37 kD.

Immunoblot analysis of recombinant cell *E. coli*:pHis-nDiCP$_{945}$ lysates indicated that the about 37 kD protein was able to bind to a T7 tag monoclonal antibody (available from Novagen, Inc., Madison, Wis.) directed against the fusion portion of the recombinant PHIS-PDiCP$_{314}$ fusion protein.

The PHIS-PDiCP$_{314}$ histidine fusion peptide was separated from *E. coli* proteins by nickel chelation chromatography and an imidazole gradient. Immunoblot analysis of the total *E. coli*:pHis-nDiCP$_{945}$ lysate, column eluate and column void volume using the T7 tag monoclonal antibody indicated that the PHIS-PDiCP$_{314}$ 37 kD protein bound to the nickel column and was eluted using an imidazole gradient.

A rabbit was immunized twice with PHIS-PDiCP$_{314}$ that had been purified by chelation chromatography. Antisera collected from this rabbit was denoted anti-PHIS-PDiCP$_{314}$ antisera. Immunoblot analysis of E. coli:pHis-nDiCP$_{945}$ lysates indicated that the anti-PHIS-PDiCP$_{314}$ antisera selectively bound to the PHIS-PDiCP$_{314}$ 37 kD protein produced by the recombinant cell.

Example 4

This Example describes the production of a D. immitis L3 cysteine protease protein of the present invention in a eukaryotic cell.

Recombinant molecule pVL1393-nCP$_{945}$, containing a D. immitis L3 cysteine protease nucleic acid molecule operatively linked to baculovirus polyhedron transcription control sequences was produced in the following manner. An about 945 nucleotide DNA fragment containing nucleotides spanning from about nucleotide 253 through about nucleotide 1197 of SEQ ID NO:1, called nDiCP$_{945}$, was PCR amplified from recombinant molecule pβgal-nDiCP$_{1298}$, described in Example 1, using the following primers: a sense primer BvCP sen (5' CGCGGATCCTATAAATATGAAAAAATTA-GAAACC 3' (SEQ ID NO:10) and an antisense primer BvCP ant 5' CGCGGATCCTTATATGGGGAATGAAGC 3' (SEQ ID NO:11), which have BamHI sites (in bold) incorporated into the primers. The N-terminal primer was designed from the nucleic acid sequence of nDiCP$_{1298}$ with modifications to enhance expression in the baculovirus system.

The PCR product was digested with BamHI restriction endonuclease, gel purified and subcloned into baculovirus shuttle plasmid pVL1393 (available from Invitrogen Inc., San Diego, Calif.) that had been cleaved with BamHI. The resulting recombinant molecule, denoted herein as pVL1393-nDiCP$_{945}$ was co-transfected into S. frugiperda Sf9 cells (donated by the Colorado Bioprocessing Center, Fort Collins, Colo.) with linear wild type baculovirus DNA (AcMNPV) and insectin cationic liposomes (available from Invitrogen) to form: S. frugiperda:pVL1393-nDiCP$_{945}$. The proper orientation of the pVL1393-nDiCP$_{945}$ insert was verified by restriction enzyme mapping.

The resulting recombinant virus, denoted vBV-nDiCP$_{945}$, was cultivated for increased production of recombinant virus and expression of PDiCP$_{314}$ was verified by immunoblot blot analysis. Immunoblot analysis using rabbit anti-PHIS-PDiCP$_{314}$ antisera (described in Example 3) demonstrated that insect cells infected with recombinant baculovirus vBV-nDiCP$_{945}$ expressed a protein detected in the culture lysates. This protein encoded by nDiCP$_{945}$, namely PDiCP$_{314}$, migrated with an apparent molecular weight of about 35 kD. Sf9 cells infected with wild type baculovirus did not express this 35 kD protein.

Example 5

This Example demonstrates the use of a D. immitis L3 cysteine protease nucleic acid molecule of the present invention to obtain a nucleic acid molecule of another filariid nematode.

A. nOvCP$_{291}$

O. volvulus L3 cysteine protease nucleic acid molecule nOvCP$_{291}$ was obtained in the following manner. D. immitis L3 cysteine protease nucleic acid molecule nDiCP$_{12981}$, produced as described in Example 1, was cleaved with EcoRI and XhoI to produce two fragments of about 850 bp and 450 bp that were gel purified and mixed hexamer labeled with Amersham's Megaprime DNA Labeling System (available from Amersham Corp., Arlington Heights, Ill.). These labeled fragments (i.e., nDiCP$_{850}$ and nDiCP$_{450}$) were used to screen an O. volvulus L3 cDNA library for plaques having nucleic acid molecules that could form stable hybrids with the D. immitis nucleic acid molecules under stringent hybridization conditions. Approximately 70,000 plaques from an O. volvulus L3 cDNA library were screened with the mixed hexamer labeled D. immitis heterologous probe using standard hybridization techniques as described by Sambrook et al., ibid. Numerous positive signals were identified from this primary hybridization screen. These regions were plugged, and the phage pools were screened further by plaque hybridization screening using the same mixed hexamer labeled D. immitis nDiCP$_{1298}$ fragment probe. One L3 cDNA clone was plaque purified, excised, and subcloned into pBluescript (available from Stratagene.). Plasmid DNA was analyzed by EcoRI restriction digestion and found to contain an insert of about 290 nucleotides.

The insert of the plasmid was sequenced as described in Example 1 and determined to have about a 291-nucleotide nucleic acid sequence, represented herein as SEQ ID NO:5. A nucleic acid molecule consisting of SEQ ID NO:5 is referred to herein as nOvCP$_{291}$. Translation of SEQ ID NO:5 indicated that nOvCP$_{291}$ includes an open reading frame spanning from about nucleotide 2 through about nucleotide 217 with a stop codon nucleotides spanning from about nucleotide 218 through about nucleotide 220, followed by a 3' untranslated region spanning from about nucleotide 221 through about nucleotide 291. The open reading frame encodes a protein of about 72 amino acids, referred to herein as POvCP$_{72}$, the amino acid sequence of which is represented herein as SEQ ID NO:6. Nucleic acid molecule nOvCP$_{216}$ consists of the coding region of POvCP$_{72}$, the nucleic acid sequence of which is represented herein as SEQ ID NO:7.

Comparison of the O. volvulus POvCP$_{72}$ amino acid sequence with the corresponding amino acid sequence of D. immitis PDiCP$_{398}$ indicate that the two sequences share about 67% identity. About 77% identity was found between the amino acid sequence encoded by approximately 284 nucleotides of the coding region plus the proposed 3' untranslated region of the O. volvulus nOvCP$_{291}$ and the amino acid sequence of the 3' end of D. immitis nDiCP$_{1298}$. Comparison of the amino acid sequence of the coding region of O. volvulus nOvCP$_{216}$ and the corresponding region of D. immitis nDiCP$_{1298}$ indicate that the two regions share about 80% identity.

About 65% identity was found between about 66 amino acids of O. volvulus POvCP$_{72}$ and the amino acid sequence of the 3' end of cathepsin L-like proteinase from liver fluke, Fasciola hepatica. About 65% identity was found between about 62 amino acids of O. volvulus POvCP$_{72}$ and the amino acid sequence of the 3' end of cathepsin L proteinase from parasitic trematode, Schistosoma mansoni. About 63% identity was found between approximately 65 amino acids of O. volvulus POvCP$_{72}$ and the amino acid sequence of the 3' end of chick cathepsin L (EC 3.4.22.15).

B. nOvCP$_{1306}$

An O. volvulus cysteine protease nucleic acid molecule, referred to herein as nOvCP$_{1306}$, was produced by PCR amplification using the following method. Antisense primer ovcpa-1, having nucleic acid sequence 5° CAT GTT CCC CTT ATT TC 3' (represented herein as SEQ ID NO:12) was used in combination with the sense vector primer T3X, having nucleic acid sequence 5° CAT GTT CCC CTT ATT TC 3' (represented herein as SEQ ID NO:13), to PCR amplify, using standard techniques, a DNA fragment from an O. volvulus L3 cDNA library (Lambda Uni-ZAP XR, reference number SAW94WL-OvL3) constructed by S. Williams and W. Lu (Smith College, Northampton, Mass.). A resulting PCR product of about 1272 bp, referred to herein as $nOvCP_{1272}$, was gel purified and cloned into the pCRII Vector® System (obtained from Invitrogen), and subjected to standard DNA sequencing techniques.

A composite nucleic acid sequence including an *O. volvulus* cysteine protease apparent full-length coding region, referred to herein as $nOvCP_{1306}$, was deduced using the nucleic acid sequence of $nOvCP_{291}$ and $nOvCP_{1272}$, and is denoted herein as SEQ ID NO:14. The nucleic acid sequence SEQ ID NO:14 includes an open reading frame spanning from about nucleotide 20 through about nucleotide 1222, with a first ATG codon spanning from about nucleotide 20 through about nucleotide 22 and a termination (stop) codon spanning from about nucleotide 1223 through about nucleotide 1225. SEQ ID NO:14 also encodes a putative hydrophobic signal peptide of about 23 amino acids, the coding sequence spanning from about nucleotide 20 through about nucleotide 88.

Translation of SEQ ID NO:14 indicates that SEQ ID NO:14 encodes a protein of about 407 amino acids, denoted herein as $POvCP_{407}$, having the deduced amino acid sequence represented herein as SEQ ID NO:15.

The open reading frame extending from nucleotide 20 of $nOvCP_{1306}$ up to the stop codon is a nucleic acid molecule of about 1203 nucleotides, denoted herein as $nOvCP_{1203}$ and represented by SEQ ID NO:16, which encodes a protein of about 401 amino acids, denoted herein as $POvCP_{401}$, having the deduced amino acid sequence represented herein as SEQ ID NO:17. Based on SEQ ID NO:17, $POvCP_{401}$ has a calculated molecular weight of about 45.8 kD and an estimated pI of about 9.4.

Comparison of the *O. volvulus* $POvCP_{401}$ amino acid sequence with the corresponding amino acid sequence of *D. immitis* $PDiCP_{398}$ indicates that the two sequences share about 49% identity. Comparison of the *O. volvulus* $nOvCP_{1306}$ nucleic acid sequence with the corresponding nucleic acid sequence of *D. immitis* $nDiCP_{1298}$ indicates that the two sequences share about 71% identity. Analysis of the amino acid sequence of $POvCP_{401}$ indicated significant conservation of residues involved in proteolytic processing of the pre-protein to form a processed pro-protein.

A BLAST homology search indicated that about 330 amino acids of $POvCP_{401}$ was most similar in amino acid sequence to the amino acid sequence of a rabbit cathepsin K precursor (OC-2 protein, Genbank Acc. No. P43236), there being about 44% identity between the two regions.

A BLAST homology search indicated that about 1005 nucleotides of the *O. volvulus* $nOvCP_{1306}$ nucleic acid sequence was most similar in nucleic acid sequence to the nucleic acid sequence of a *Spirometra mansonoides* cysteine protease (Genbank Acc. No. U51913), there being about 51% identity between the two regions.

Taken together, these examples clearly indicate that knowledge of the nucleic acid sequence of *D. immitis* and *O. volvulus* cysteine protease nucleic acid molecules of the present invention enables the identification and isolation of additional filariid nematode nucleic acid molecules of the present invention.

Example 7

This Example describes the production of a eukaryotic recombinant cell and use of that cell to produce a eukaryotic version of a *D. immitis* L3 cysteine protease protein of the present invention.

Recombinant molecule $pKB3poly-nDiCP_{1071}$, containing a *D. immitis* L3 cysteine protease nucleic acid molecule spanning nucleotides from about 127 through about 1197 of SEQ ID NO:1 operatively linked to the vaccinia virus p11 late promoter transcription control sequences was produced in the following manner. The pKB3poly poxvirus shuttle vector was created by modifying a region of plasmid pKB3 ($P_{11}$-type) (pKB3 ($P_{11}$-type) plasmid (described in U.S. Pat. No. 5,348,741, by Esposito et al., issued Sep. 20, 1994) such that the initiation codon linked to the p11 promoter was mutated and additional unique polylinker restriction sites were added. The resulting poxvirus vector, referred to as pKB3poly, requires the insert DNA to provide the ATG initiation codon when inserted downstream of the p11 promoter. The pKB3poly vector is designed such that foreign DNA cloned into the polylinker region of pKB3poly vector will recombine into the thymidine kinase (TK) gene of wildtype poxvirus.

In order to subclone a *D. immitis* L3 cysteine protease nucleic acid molecule into the pKB3poly expression vector, an about 1071 nucleotide *D. immitis* L3 cysteine protease nucleic acid molecule-containing fragment spanning from about nucleotide 127 through about nucleotide 1197 of SEQ ID NO:1, called $nDiCP_{1071}$, was PCR amplified from recombinant molecule $p\beta gal-nDiCP_{1298}$, described in Example 1, using the following primers: a sense primer EukCP sen 5' CGGGGTACCAGGAAATATGAC-GAGACTTAC 3' (SEQ ID NO:18) and an antisense primer EukCP ant 5° CGGGGTACCTTATATGGGGAATGAAGC 3' (SEQ ID NO:19), which have Asp718I sites (in bold) incorporated into the primers.

The PCR product was digested with Asp718I restriction endonuclease, gel purified and subcloned into the pKB3poly shuttle vector which had been digested with Asp718I restriction endonuclease, treated with calf intestinal phosphatase and gel purified to produce recombinant molecule $pKB3poly-nDiCP_{1071}$. The proper orientation of the insert was verified by restriction digest mapping.

In order to produce a recombinant raccoon poxvirus capable of directing the production of $PDiCP_{356}$, BS-C-1 African green monkey kidney cells (obtained from American Type Culture Collection (ATCC), Rockville, Md.) were infected with wild type raccoon poxvirus RCN CDC/V71-I-85A) (obtained from Dr. Joseph Esposito; Espositc et al, 1985, *Virology* 143,230–251) and then transfected with the $pKB3poly-nDiCP_{1071}$ vector DNA by calcium phosphate precipitation to form recombinant cell $BSC1:pKB3poly-nDiCP_{1071}$. The resulting recombinant virus, denoted $Rcn-nDiCP_{1071}$, was plaque purified twice in RAT-2 rat embryo, thymidine kinase mutant cells (available from ATCC) in the presence of bromodeoxyuridine (BUDR) to select for TK⁻ recombinants. The TK⁻ recombinant virus was plaque purified once and then cultivated in BS-C-1 cells without BUDR. Expression of the *D. immitis* L3 cysteine protease recombinant protein was monitored by SDS PAGE of infected BS-C-1 cell lysates, followed by immunoblot analysis with the rabbit anti-PHIS-$PDiCP_{314}$ antisera (described in Example 3). Recombinant cell $BSC1:pKB3poly-nDiCP_{1071}$ produced a eukaryotic version of $PDiCP_{356}$, that migrated with an apparent molecular weight of about 42 kD and that was selectively bound by rabbit anti-PHIS-$PDiCP_{314}$ antisera.

Example 8

This Example describes the production of a eukaryotic recombinant cell and use of that cell to produce a multivalent virus vaccine capable of expressing both *D. immitis* L3 cysteine protease and *D. immitis* PLA2 proteins (*D. immitis*

PLA2 nucleic acid molecules and proteins are described in PCT International Publication No. WO 94/15593, published Jul. 21, 1994).

Recombinant molecule p11-nDiCP$_{1071}$/pSyn-nDiPLA2$_{453}$, containing two *D. immitis* nucleic acid molecules operatively linked to separate promoters was produced in the following manner. p11/pSyn pox virus shuttle vector was created by modifying a region of plasmid pKB3poly shuttle plasmid (described in Example 7) in the following manner. A double stranded linker molecule was synthesized to contain the poxvirus promoter pSyn (see, for example, Davison et al, 1990, *Nuc. Acids Res.* 18, 4285–4286) as follows. Two complimentary oligonucleotides, EJH016 and EJH017 were synthesized and have the following nucleotide sequence: EJH016 5' GATC-CAATTGGATCAGCTTTTTTTTTTTTTTTTTTGG CATATAAATAAG 3' (SEQ ID NO:20) with the BamHI cohesive end indicated in bold; and EJH017 5' GTACCT-TATTATATGCC AAAAA AAAAAGcTGATCCAATTG 3' (SEQ ID NO: 21) with the Asp718I cohesive end indicated in bold. The two oligonucleotides were annealed to create a 45 nucleotide double stranded region with a 4-nucleotide single stranded BamHI cohesive terminus on one end and a 4-nucleotide single stranded Asp718I cohesive terminus on the other end to facilitate directional cloning of this fragment into the unique BamHI and Asp718I sites of pKB3poly shuttle plasmid. The resulting poxvirus vector, referred to as p11/pSyn, requires the insert DNA to provide the-ATG initiation codon when inserted downstream of the psyn or the $P_{11}$ promoter. The p11/pSyn vector is designed such that foreign DNA cloned into the polylinker region of p11/pSyn vector will recombine into the TK gene of wildtype poxvirus.

A recombinant molecule containing (a) a *D. immitis* PLA2 nucleic acid molecule containing the PLA2 open reading frame (described in WO 94/15593, ibid.), operatively linked to pSyn transcription control sequences and (b) a *D. immitis* L3 cysteine protease nucleic acid molecule spanning nucleotides from about 127 through about 1197 of SEQ ID NO:1 operatively linked to the vaccinia virus $P_{11}$ late promoter transcription control sequences was produced in the following manner.

In order to subclone a PLA2 nucleic acid molecule into p11/pSyn expression vector, a nucleic acid molecule containing the PLA2 open reading frame was cleaved from *D. immitis* PLA-2-nucleic acid molecule-containing vector p76-52.H3 (produced as described in Example 15 of WO 94/15593, ibid.) using BamHI restriction endonuclease. The about 453 nucleotide insert DNA (referred to as Rcn-nDiPLA2$_{453}$) was treated with Klenow enzyme to create blunt ends resulting in the production of nucleic acid molecule nRcnDiPLA2$_{453}$, gel purified and subcloned into the p11/pSyn shuttle vector, which had been restricted with Asp718I and EcoRI restriction endonuclease, treated with Klenow enzyme to create blunt ends, treated with calf intestinal phosphatase and gel purified, to produce recombinant molecule p11/pSyn-nDiPLA2$_{453}$. The proper orientation of the Rcn-nDiPLA2$_{453}$ insert was verified by restriction digest mapping.

In order to subclone a *D. immitis* L3 cysteine protease nucleic acid molecule into p11/pSyn-nDiPLA2$_{453}$ expression vector, a L3 cysteine protease nucleic acid molecule-containing fragment was cleaved from *D. immitis* pKB3poly-nDiCP$_{1071}$ DNA (produced as in Example 7), by Asp718I restriction endonuclease. The about 1071 nucleotide insert DNA (referred to as Rcn-nDiCP$_{1071}$,) was treated with Klenow enzyme to create blunt ends resulting in the production of nucleic acid molecule nRcnDiCP$_{1071}$, gel purified and subcloned into the p11/pSyn-nDiPLA2$_{453}$ shuttle vector, which had been digested with SmaI restriction endonuclease, treated with calf intestinal phosphatase and gel purified, to produce recombinant molecule p11-nDiCP$_{1071}$/pSyn-nDiPLA2$_{453}$. The proper orientation of the Rcn-nDiCP$_{1071}$ insert was verified by restriction digest mapping.

In order to produce a recombinant raccoon poxvirus capable of directing the production of PDiCP$_{356}$ and PDiPLA2$_{150}$, BS-C-1 African green monkey kidney cells (obtained from ATCC, Rockville, Md.) were infected with wild type raccoon poxvirus RCN CDC/V71-I-85A and then transfected with the p11-nDiCP$_{1071}$/pSyn-nDiPLA2$_{453}$ vector DNA to form recombinant cell BSC1:p11-nDiCP$_{1071}$/pSyn-nDiPLA2$_{453}$. The resulting recombinant virus, denoted Rcn-nDiCP$_{1071}$-nDiPLA2$_{4531}$ was cultivated in RAT-2 rat embryo, thymidine kinase mutant cells as described in Example 7. Expression of the cysteine protease and the PLA2 recombinant proteins was monitored by SDS PAGE of infected BS-C-1 cell lysates, followed by immunoblot analysis with the rabbit anti-PHIS-PDiCP$_{314}$ antisera and rabbit anti-PHIS-PDiPLA2 antisera (produced as described in Example 14 of WO 94/15593, ibid.).

Example 9

This Example describes the production of a *D. immitis* L3 cysteine protease protein using a eukaryotic cell transformed with a *D. immitis* L3 cysteine protease nucleic acid molecule of the present invention.

Recombinant molecule pCMV-nDiCP$_{1071}$, containing a *D. immitis* L3 cysteine protease nucleic acid molecule spanning nucleotides from about 127 through about 1197 of SEQ ID NO:1operatively linked to the cytomegalovirus (CMV) promoter transcription control was produced in the following manner. The pCMV expression vector was produced as follows. Vector pRc/RSV (available from InVitrogen) was cleaved by restriction enzyme PvuII, and the 2963-base pair PvuII fragment gel purified. That fragment was self-ligated to form vector pRc/RSV(Pvu), which contains a Rous Sarcoma Virus (RSV) long terminal repeat, a multiple cloning site, a bovine growth hormone polyadenylation sequence, a bacterial origin of replication and an ampicillin resistance gene.

Expression vector PVXRC was produced by introducing a HindIII fragment containing the cytomegalovirus (CMV) intermediate early promoter and first intron (i.e., Intron A) into pRc/RSV(Pvu) that had been cleaved by HindIII. Expression vector pCMV was produced by introducing a HindIII/SspI fragment containing the CMV intermediate early promoter and first intron (i.e., Intron A) into pRc/RSV (Pvu) that had been cleaved by HindIII and NruI.

In order to subclone a *D. immitis* L3 cysteine protease nucleic acid molecule into the pCMV expression vector, *D. immitis* L3 cysteine protease nucleic acid molecule-containing fragments were PCR amplified as described in Example 7. The about 1071 PCR product (referred to as nDiCP$_{1071}$) was digested with Asp718I restriction endonuclease, gel purified and subcloned into the pCMV expression vector which had been restricted with Asp718I restriction endonuclease, treated with calf intestinal phosphatase and gel purified to produce recombinant molecule pCMV-nDiCP$_{1071}$. The proper orientation of the insert was verified by restriction mapping.

To produce the recombinant cell line BHK:pCMV-nDiCP$_{1071}$, pCMV-nDiCP$_{1071}$ was transfected into Baby Hamster Kidney Cells (BHK) (obtained from ATCC, Rockville, Md.) was performed by standard procedures. Briefly, six-well polystyrene tissue culture plates were seeded with about $3\times10^5$ cells/well in 2 mls of MEM NEAA Earle's salts (available from Irvine Scientific, Santa Ana Calif. with 100 mM L-glutamine, 5% FBS (complete growth media). Cells were grown to 80% confluence (about 48 hr). The recombinant molecules to be transfected were purified using Qiagen tips (available from Qiagen Inc., Chatsworth, Calif.) per manufacturer's instructions. Using polystyrene plates, about 2 $\mu$g of each recombinant molecule was mixed with about 100 $\mu$l OptiMEM (available from Gibco BRL). About 15 $\mu$l Lipofectamine (available from Gibco BRL) was mixed with about 100 $\mu$l OptiMEM. The Lipofectamine mixture was then added to the recombinant molecule mixture and incubated at room temperature for about 30 min. After incubation, about 800 $\mu$l OptiMEM was added and the entire mixture overlaid onto the BHK cells that had been rinsed with OptiMEM. Cells were incubated at 37° C., 5% $CO_2$, 90% relative humidity. The transfection mixture was then removed and replaced with about 2 mls complete growth media.

Transfected cells were incubated at 37° C., 5% $CO_2$, 90% relative humidity for about 24 hr and harvested. The media was removed, the cells washed twice with about 2 mls PBS and scraped off the plate in about 1.5 ml PBS. The cells were pelleted by centrifugation, the PBS removed and the cells frozen.

Expression of the *D. immitis* L3 cysteine protease recombinant protein was monitored by SDS PAGE of infected BHK cell lysates, followed by immunoblot analysis with the rabbit anti-PHIS-PDiC$P_{314}$ antisera. Recombinant cell BHK:pCMV-nDiC$P_{1071}$ produced a eukaryotic version of PDiC$P_{356}$, that migrated with an apparent molecular weight of about 42 kD, that was bound selectively by rabbit anti-PHIS-PDiC$P_{314}$ antisera.

Example 10

This Example describes the expression of *D. immitis* L3 cysteine protease native protein in different developmental stages of the *D. immitis* life cycle.

Total protein was prepared from 0 hour third stage larvae (0-hr L3), 48 hour third stage larvae (48-hr L3), 6 day fourth stage larvae (6-day L4), and adult male or adult female worms. Immunoblot analysis of these antigen preparations with rabbit anti-PHIS-PDiC$P_{314}$ antiserum (produced as described in Example 3) indicated that the *D. immitis* native cysteine protease protein migrated at about 22 kD and was detected only in the 48-hr L3 and 6-day L4 larval preparations. This 22 kD size of the *D. immitis* native protein is consistent with the predicted size of a mature protein resulting from processing of the amino acid sequence represented by PDiC$P_{356}$. Cleavage of an amino terminal propeptide sequence to form an active enzyme is characteristic of peptidases of the papain family. The deduced amino acid sequences represented by nDiC$P_{1071}$ (described in Example 7) contains conserved amino acid residues present in the propeptide sequences, namely the ERFNN motif including glutamine (E) at position 64, arginine (R) at position 68, phenylalanine (F) at position 72, asparagine (N) at position 75 and asparagine (N) at position 83.

Example 11

This example discloses the production of a recombinant cell of the present invention.

Recombinant molecule pHis-nOvC$P_{1203}$ was produced in the following manner. An about 1203 nucleotide DNA fragment containing nucleotides spanning from about nucleotide 89 through about nucleotide 1222 of SEQ ID NO:14, called nOvC$P_{1203}$, was polymerase chain reaction (PCR) amplified from nOvC$P_{1306}$, described in Example 5, using the following primers: primers EXPCP5' 5' ACTGGATCCGCAAGTGCAACAGCTACGAGAAG 3' (SEQ ID NO:23) (BamHI site in bold) and EXPCP3' 5' TAAGGTACCTTATATGGGTATTGAAGCCAACGTTGCGATGTGGCACATGTTCCCCTTATT TCG 3' (SEQ ID NO:24) (KpnI site in bold). The PCR product was digested with BamHI restriction endonuclease, gel purified and subcloned into expression vector lambda$P_R$/$T^2$ori/S10HIS-RSET-A9 (produced as described in Example 7 of PCT Publication No. WO 95/24198, published Sep. 14, 1995) that had been digested with BamHI and KpnI. The resulting recombinant molecule pHis-nOvC$P_{1203}$ was transformed into *E. coli* to form recombinant cell *E. coli*:pHis-nOvC$P_{1203}$.

Example 12

This Example describes the production in bacteria of an *O. volvulus* L3 cysteine protease protein of the present invention.

Recombinant cell *E. coli*:pHis-nOvC$P_{1203}$ was produced as described in Example 11, was cultured in shake flasks containing an enriched bacterial growth medium containing 0.1 mg/ml ampicillin and 0.1% glucose at about 32° C. When the cells reached an $OD_{600}$ of about 0.4, expression of *O. volvulus* nOvC$P_{1203}$ was induced by addition of about 0.5 mM isopropyl-β-D-thiogalactoside (IPTG), and the cells cultured for about 3 hours at about 32° C.

Immunoblot analysis of recombinant cell *E. coli*:pHis-nOvC$P_{1203}$ lysates indicated that an about 47 kD protein was able to bind to a T7 tag monoclonal antibody (available from Novagen, Inc., Madison, Wis.) directed against the fusion portion of the recombinant pHIS-POvC$P_{401}$ fusion protein.

Example 13

This Example describes additional nucleic acid and deduced amino acid sequences of a filariid nematode cysteine protease nucleic acid molecule of the present invention, the isolation of which was described in Example 1. It should be noted that nucleic acid sequencing technology is not entirely error-free, and as such variations between sequences may be due to a number of factors, including, but not limited to, sequencing errors. Thus, the nucleic acid sequences presented herein, represent apparent nucleic acid sequences of nucleic acid molecules encoding a *D. immitis* CP protein of the present invention.

*D. immitis* L3 cysteine protease nucleic acid molecule nDiC$P_{1298}$, isolated as described in Example 1, was submitted to additional DNA sequence analysis which indicated that the nucleic acid molecule apparently included an extra six nucleotides—this nucleic acid molecule is hence referred to as nDiC$P_{1304}$. Nucleic acid molecule nDiC$P_{1304}$ was sequenced using the Sanger dideoxy chain termination method, using the PRISM™ Ready Dye Terminator Cycle Sequencing Kit with AmpliTaq® DNA Polymerase, FS (available from the Perkin-Elmer Corporation, Norwalk, Conn. PCR extensions were done in the GeneAmp™ PCR System 9600 (available from Perkin-Elmer). Excess dye terminators were removed from extension products using the Centriflex™ Gel Filtration Cartridge (available from Advanced Genetics Technologies Corporation, Gaithersburg, Md.) following their standard protocol. Samples were resuspended according to ABI protocols and were run on a Perkin-Elmer ABI PRISM™ 377 Automated DNA Sequencer. DNA sequence analyses, including the compilation of sequences and the determination of open reading frames, were performed using either the DNAsis™ program (available from Hitachi Software, San Bruno, Calif.) or the MacVector™ program (available from the Eastman Kodak Company, New Haven, Conn.). An about 1304 nucleotide consensus sequence of the entire nDiCP$_{1304}$ nucleic acid molecule was determined and is denoted herein as SEQ ID NO:32 (the coding strand) and SEQ ID NO:35 (the complementary strand). The nucleic acid sequence SEQ ID NO:32 includes an open reading frame spanning from about nucleotide 1 through about nucleotide 1200. While not being bound by theory, the nDiCP$_{1304}$ nucleic acid sequence contains an apparently partial coding region, truncated at the 5' end. The first in-frame codon spans nucleotides from about 1 through about 3 and the stop codon spans nucleotides from about 1198 through about 1200 of SEQ ID NO:32. A putative polyadenylation signal (5' AATAAA 3') is located from about nucleotide 1271 through about nucleotide 1276 of SEQ ID NO:32.

Translation of SEQ ID NO:32 yields a protein of about 400 amino acids, denoted PDiCP$_{400}$, the deduced amino acid sequence of which is represented herein as SEQ ID NO:33. The nucleic acid molecule comprising the coding region encoding PDiCP$_{400}$ is referred to herein as nDiCP$_{1200}$, the nucleic acid sequence of which is denoted herein as SEQ ID NO:34 (the coding strand) and SEQ ID NO:36 (the complementary strand). Analysis of SEQ ID NO:33 suggests the presence of a partial N-terminal signal peptide encoded by a stretch of amino acids spanning from about amino acid 1 through about amino acid 14, or from about amino acid 1 through about amino acid 18. Secreted proteins with these putative signal peptides removed are denoted herein as PDiCP$_{386}$ and PDiCP$_{382}$, respectively. PDiCP$_{386}$ and PDiCP$_{382}$ are encoded by nucleic acid molecules of about 1158 and about 1146 nucleotides, respectively, denoted herein as nDiCP$_{1158}$ and nDiCP$_{1146}$, respectively.

The very highly conserved catalytic residues of members of the papain family of cysteine peptidases are a cysteine at amino acid position 25 (C25) and a histidine residue at position 159 (H159) of the mature, processed peptide. Other amino acid residues important for catalysis include a glutamine at position 19 (Q19) and asparagine at position 175 (N175). The numbering of these amino acids correspond to the amino acid position of the mature Carica papaya papain sequence (Genbank Acc. No. M15203).

Based on a homology alignment of the PDiCP$_{400}$ deduced amino acid sequence with known papain amino acid sequences, the predicted mature protein resulting from the processing of the PDiCP$_{400}$ CP protein, referred to as PDiCP$_{215}$ and denoted herein as SEQ ID NO:38, would begin with the leucine at about residue 186 of PDiCP$_{400}$. This predicted processing point is analogous to the predicted processing point for the PDiCP$_{356}$ CP protein, at about leucine 144 of SEQ ID NO:25, as described in Example 1. PDiCP$_{215}$ is encoded by a nucleic acid molecule of about 645 nucleotides denoted herein as nDiCP$_{645}$, the nucleic acid sequence of which is represented by SEQ ID NO:37 (the coding strand) and SEQ ID NO:39 (the complementary strand). PDiCP$_{215}$ contains the papain family conserved residues believed to be involved in catalysis, namely, a cysteine at residue 25 (C25), a histidine at residue 162 which corresponds to the H159 of papain, a glutamine at position 19 (Q19) and an asparagine at residue 183 which corresponds to the N175 of papain. In addition, many members of the papain Cl family contain a proline residue at position 2 of the mature, processed enzyme. The PDiCP$_{215}$ amino acid sequence SEQ ID NO:38 has a proline at position 2 of the predicted mature enzyme.

Homology searches of the non-redundant protein sequence database were performed through the National Center for Biotechnology Information using the BLAST network. The protein sequence database includes+ SwissProt+PIR+SPUpdate+GenPept+GPUpdate. Using BLAST, amino acid sequences SEQ ID NO:33 and SEQ ID NO:28 were found to have significant homology to certain cysteine proteases. SEQ ID NO:33 and SEQ ID NO:38 were aligned to the homologous sequences using the Maximum Matching program contained in the DNAsis™ software package, with the default settings. SEQ ID NO:33 (in its entirety) was found to be most closely homologous, at about 38 percent identity, to Bos taurus cathepsin L (Genbank Accession No. X91755), and SEQ ID NO:38 was found to be most closely homologous, at about 50 percent identity, to Gallus gallus cathepsin L (PIR Accession No. 86218).

Example 14

This Example describes the production of additional D. immitis L3 cysteine protease proteins of the present invention in eukaryotic cells.

A. Recombinant molecule pVL1392-nDiCP$_{1206}$, containing a D. immitis L3 cysteine protease nucleic acid molecule operatively linked to baculovirus polyhedron transcription control sequences was produced in the following manner. An about 1206 nucleotide DNA fragment containing nucleotides spanning from about nucleotide 1 through about nucleotide 1203 of SEQ ID NO:32 (plus an added ATG initiation codon), called nDiCP$_{1206}$ (SEQ ID NO:43), was PCR amplified from recombinant molecule pβgal-nDiCP$_{1298}$, described in Example 1, using the following primers: a sense primer, MM01 5' CGCAGATCTA TGCT-TCGATT CATTGC 3' (SEQ ID NO:40) and an antisense primer MM02 5' CGCAGATCTT TATATGGGGA ATGAAGC 3' (SEQ ID NO:41), which have BglII restriction sites (in bold) incorporated into the primers. The N-terminal primer was designed from the nucleic acid sequence of nDiCP$_{1304}$ with modifications to enhance expression in the baculovirus system.

The PCR product was digested with BglII restriction endonuclease, gel purified and subcloned into baculovirus shuttle plasmid pVL1392 (available from Invitrogen) that had been cleaved with BglII. The resulting recombinant molecule, denoted herein as pVL1392-nDiCP$_{1206}$ was co-transfected into S. frugiperda Sf9 cells (Available from Invitrogen) with BaculoGold™ baculovirus DNA (ACMNPV) (available from Pharmingen, San Diego, Calif.) to form S. frugiperda:pVL1392-nDiCP$_{1206}$. The proper orientation of the pVL1392-nDiCP$_{1206}$ insert was verified by restriction enzyme mapping.

The resulting recombinant virus, denoted vBV-nDiCP$_{1206}$, was cultivated for increased production of recombinant virus and expression of PDiCP$_{401}$ (SEQ ID NO:44) was verified by immunoblot analysis. Immunoblot analysis using rabbit anti-PHIS-PDiCP$_{314}$ antisera (described in Example 3) demonstrated that insect cells infected with recombinant baculovirus vBV-nDiCP$_{1206}$ expressed a protein detected in the culture lysates. This protein encoded by nDiCP$_{1206}$ namely PDiCP$_{401}$, migrated with an apparent molecular weight of about 55 kD. Sf9 cells infected with wild type baculovirus did not express this 55 kD protein.

B. Recombinant molecule pVL1393/nPLA2-nDiCP$_{726}$, containing a D. immitis L3 cysteine protease nucleic acid molecule fused in-frame with the 66 nucleotide signal segment of the *D. immitis* PLA2 gene, and operatively linked to baculovirus polyhedron transcription control sequences, was produced in the following manner. An about 648 nucleotide DNA fragment containing nucleotides spanning from about nucleotide 556 through about nucleotide 1203 of SEQ ID NO:32, was PCR amplified from recombinant molecule pβgal-nDiCP$_{1298}$, described in Example 1, using the following primers: a sense primer MM03 5' CCGGAATTCT ACTGCCAAAA TATGTTGATT GG 3' (SEQ ID NO:42) and an antisense primer MM02 5' CGCAGATCTT TATATGGGGA ATGAAGC 3' (SEQ ID NO:41), which have EcoRI and BglII restriction sites (in bold), respectively, incorporated into the primers.

The PCR product was digested with EcoRI and BglII restriction endonucleases, gel purified and subcloned into baculovirus shuttle plasmid pVL1393/PLA2 which had been cleaved with EcoRI and BglII. This vector is a modification of vector pVL1393 in which a 66 nucleotide signal segment of the *D. immitis* PLA2 gene was inserted such that nucleic acid molecules could be fused in-frame downstream of the signal segment. The fusion comprises a 10-nucleotide portion of the pVL1393 polylinker region. This signal segment is disclosed as nucleotides 7–72 of SEQ ID NO:1 in pending U.S. patent application Ser. No. 08/482,304, by Grieve, et al., filed Jun. 7, 1995, which is incorporated herein by reference in its entirety. The nucleotide sequence of the coding region (including the stop codon) of nPLA2-nDiCP726 is presented herein as SEQ ID NO:45. The resulting recombinant molecule, denoted herein as pVL1393/nPLA2-nDiCP$_{726}$ was co-transfected into *S. frugiperda* Sf9 cells (Available from Invitrogen) with BaculoGold™ baculovirus DNA (AcMNPV) (available from Pharmingen) to form: *S. frugiperda*:pVL1393/nPLA2-nDiCP$_{726}$.

The resulting recombinant virus, denoted vBV-nPLA2-nDiCP$_{726}$, is cultivated for increased production of recombinant virus and expression of PPLA2-PDiCP$_{241}$ (SEQ ID NO:46) (215 amino acids encoded by nDiCP$_{645}$, 22 amino acids encoded by the PLA2 signal segment, and 4 amino acids encoded by the pVL1393 polylinker and primer MM03) is verified by immunoblot analysis, using rabbit anti-PHIS-PDiCP$_{314}$ antisera.

SEQUENCE LISTING

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 through SEQ ID NO:46 submitted herewith are the same.

```
                              SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
          (A) LENGTH: 1298 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: CDS
          (B) LOCATION: 1..1194

(xi) SEQUENCE DESCRIPTION: SEQ ID NO:1:

CTT CGA TTC ATT GCT TTA TTG GCC ATA CTC ACT TTC TTG ATC GAC TTT        48
Leu Arg Phe Ile Ala Leu Leu Ala Ile Leu Thr Phe Leu Ile Asp Phe
  1               5                  10                  15

ACC GTC TCA TTC AAT GAT GAA ATT CTA CAG CTG AAA GAA GTA TTG GGA        96
Thr Val Ser Phe Asn Asp Glu Ile Leu Gln Leu Lys Glu Val Leu Gly
             20                  25                  30

ATG TTT GAT GAA GAT TAC AGA TTA GGA AAT ATG ACG AGA CTT ACG TTT       144
Met Phe Asp Glu Asp Tyr Arg Leu Gly Asn Met Thr Arg Leu Thr Phe
         35                  40                  45

GAT TTT CAA AAC GCT TTG AAA GAT TAC GGC GAT GGA GAA AAC AGT TAT       192
Asp Phe Gln Asn Ala Leu Lys Asp Tyr Gly Asp Gly Glu Asn Ser Tyr
     50                  55                  60

AAA CTA ACT GCT GTG CAA TCT TTC CTC AAA AAA TTA GAA GAA AAC GGT       240
Lys Leu Thr Ala Val Gln Ser Phe Leu Lys Lys Leu Glu Glu Asn Gly
 65                  70                  75                  80
```

```
GAG GAA CAA GCG ATG AAA AAA TTA GAA ACC GAA TGG CAA GAG TAT TTA      288
Glu Glu Gln Ala Met Lys Lys Leu Glu Thr Glu Trp Gln Glu Tyr Leu
                85                  90                  95

ACA GCT CTT GGA AAA GAA TAT GAT TCA GAA GAG AAT AAA TTG AGA ATG      336
Thr Ala Leu Gly Lys Glu Tyr Asp Ser Glu Glu Asn Lys Leu Arg Met
            100                 105                 110

GCA ATA TTT GAA AGT AAT GAA TTA ATG ACA GAA GCA TTA AAT AGA AAA      384
Ala Ile Phe Glu Ser Asn Glu Leu Met Thr Glu Ala Leu Asn Arg Lys
        115                 120                 125

TAT GAG CAA GGC TTA ATT TCA TTT AAA ACT GCC CTG AAT GAT ATG GCT      432
Tyr Glu Gln Gly Leu Ile Ser Phe Lys Thr Ala Leu Asn Asp Met Ala
130                 135                 140

GAT TTG ACC GAT CAA GAA TTC AAC CTA ATG AAT GGA CTT CTA CTG CAT      480
Asp Leu Thr Asp Gln Glu Phe Asn Leu Met Asn Gly Leu Leu Leu His
145                 150                 155                 160

AAT GAA ACT TCC CAT ACA AGA AGG TAT GCT CGA CAA GTA TCT GGT GAA      528
Asn Glu Thr Ser His Thr Arg Arg Tyr Ala Arg Gln Val Ser Gly Glu
                165                 170                 175

TTT CTC AAG TAC AAT AAG AGT ACA AAG CTG CCA AAA TAT GTT GAT TGG      576
Phe Leu Lys Tyr Asn Lys Ser Thr Lys Leu Pro Lys Tyr Val Asp Trp
            180                 185                 190

AGA AAG AGA GGA TAT GTC ACA CCT GCC AAA GAG CAG GGC TTG TGT GGT      624
Arg Lys Arg Gly Tyr Val Thr Pro Ala Lys Glu Gln Gly Leu Cys Gly
        195                 200                 205

AGT TGT TAT GCA TTC TGC AGC TGC AGC ATT AGA AGC CTT ATA TAT AAA      672
Ser Cys Tyr Ala Phe Cys Ser Cys Ser Ile Arg Ser Leu Ile Tyr Lys
210                 215                 220

AAG ACG AAA AAC AAA CTT CTC GAT TTA TCT CCG CAA AAT ATT CTA GAT      720
Lys Thr Lys Asn Lys Leu Leu Asp Leu Ser Pro Gln Asn Ile Leu Asp
225                 230                 235                 240

TGT ACA TGG GAT CTC GGT AAT AAT GGT TGC CAT GGT GGT TTC ATG AAT      768
Cys Thr Trp Asp Leu Gly Asn Asn Gly Cys His Gly Gly Phe Met Asn
                245                 250                 255

CCG GCA TTT TAT TAT GCA AGT AAG GCA GGT ATT GCA TCA GAA GCG AAA      816
Pro Ala Phe Tyr Tyr Ala Ser Lys Ala Gly Ile Ala Ser Glu Ala Lys
            260                 265                 270

TAT CCG TAT GTT CAC ACT GCA AGA CGT ACA TGC TAT TGG CGG AAA GAT      864
Tyr Pro Tyr Val His Thr Ala Arg Arg Thr Cys Tyr Trp Arg Lys Asp
        275                 280                 285

ATA GTT GCT GCT ACT GAT AAT GGT TAC ACT CGA ATA CAA CAA GGT GAT      912
Ile Val Ala Ala Thr Asp Asn Gly Tyr Thr Arg Ile Gln Gln Gly Asp
290                 295                 300

GAG AAA GGT CTC AAT ATG CTG TGG CAA TTG ACC GTT GTT GTT GGA ATT      960
Glu Lys Gly Leu Asn Met Leu Trp Gln Leu Thr Val Val Val Gly Ile
305                 310                 315                 320

TCT GGA TAT CAA CAC GAT TTT AAA TTT TAT AAA TCC GGT GTC TAC TCT     1008
Ser Gly Tyr Gln His Asp Phe Lys Phe Tyr Lys Ser Gly Val Tyr Ser
                325                 330                 335

AGT GAT CAA TGT CGT GTT CCT AAT CAC GCA GTA CTG GTT GTT GGT TAT     1056
Ser Asp Gln Cys Arg Val Pro Asn His Ala Val Leu Val Val Gly Tyr
            340                 345                 350

GGA ACC AGT CAA AAA ACA CGG GAT TAT TGG ATT ATT AAA AAT AGT TGG     1104
Gly Thr Ser Gln Lys Thr Arg Asp Tyr Trp Ile Ile Lys Asn Ser Trp
        355                 360                 365

GGA ACT AAT TGG GCA AGA AAT GGA TAT GGT TAT ATG AAG CGA AAC GAA     1152
Gly Thr Asn Trp Ala Arg Asn Gly Tyr Gly Tyr Met Lys Arg Asn Glu
370                 375                 380

AGG AAT ATG TGT CAT ATC GCT ACG ATG GCT TCA TTC CCC ATA              1194
Arg Asn Met Cys His Ile Ala Thr Met Ala Ser Phe Pro Ile
385                 390                 395
```

```
TAATTATGAT TTAATTTGTT TTCGAAAAAT ATTTATTTTG CTAATTTTCA ATATTTGATA      1254

ATTTTGGTTT AATAAAAAGA AATTGGGAAA AAAAAAAAAA AAAA                      1298
```

(2) INFORMATION FOR SEQ ID NO:2:

(i) SEQUENCE CHARACTERISTICS:
        (A) LENGTH: 398 amino acids
        (B) TYPE: amino acid
        (D) TOPOLOGY: linear (ii) MOLECULE TYPE: protein (xi) SEQUENCE DESCRIPTION: SEQ ID NO:2:

```
Leu Arg Phe Ile Ala Leu Leu Ala Ile Leu Thr Phe Leu Ile Asp Phe
 1               5                  10                  15

Thr Val Ser Phe Asn Asp Glu Ile Leu Gln Leu Lys Glu Val Leu Gly
                20                  25                  30

Met Phe Asp Glu Asp Tyr Arg Leu Gly Asn Met Thr Arg Leu Thr Phe
            35                  40                  45

Asp Phe Gln Asn Ala Leu Lys Asp Tyr Gly Asp Gly Glu Asn Ser Tyr
    50                  55                  60

Lys Leu Thr Ala Val Gln Ser Phe Leu Lys Lys Leu Glu Glu Asn Gly
65                  70                  75                  80

Glu Glu Gln Ala Met Lys Lys Leu Glu Thr Glu Trp Gln Glu Tyr Leu
                85                  90                  95

Thr Ala Leu Gly Lys Glu Tyr Asp Ser Glu Glu Asn Lys Leu Arg Met
            100                 105                 110

Ala Ile Phe Glu Ser Asn Glu Leu Met Thr Glu Ala Leu Asn Arg Lys
    115                 120                 125

Tyr Glu Gln Gly Leu Ile Ser Phe Lys Thr Ala Leu Asn Asp Met Ala
130                 135                 140

Asp Leu Thr Asp Gln Glu Phe Asn Leu Met Asn Gly Leu Leu Leu His
145                 150                 155                 160

Asn Glu Thr Ser His Thr Arg Arg Tyr Ala Arg Gln Val Ser Gly Glu
                165                 170                 175

Phe Leu Lys Tyr Asn Lys Ser Thr Lys Leu Pro Lys Tyr Val Asp Trp
            180                 185                 190

Arg Lys Arg Gly Tyr Val Thr Pro Ala Lys Glu Gln Gly Leu Cys Gly
    195                 200                 205

Ser Cys Tyr Ala Phe Cys Ser Cys Ser Ile Arg Ser Leu Ile Tyr Lys
210                 215                 220

Lys Thr Lys Asn Lys Leu Leu Asp Leu Ser Pro Gln Asn Ile Leu Asp
225                 230                 235                 240

Cys Thr Trp Asp Leu Gly Asn Asn Gly Cys His Gly Gly Phe Met Asn
                245                 250                 255

Pro Ala Phe Tyr Tyr Ala Ser Lys Ala Gly Ile Ala Ser Glu Ala Lys
            260                 265                 270

Tyr Pro Tyr Val His Thr Ala Arg Thr Cys Tyr Trp Arg Lys Asp
    275                 280                 285

Ile Val Ala Ala Thr Asp Asn Gly Tyr Thr Arg Ile Gln Gln Gly Asp
290                 295                 300

Glu Lys Gly Leu Asn Met Leu Trp Gln Leu Thr Val Val Gly Ile
305                 310                 315                 320

Ser Gly Tyr Gln His Asp Phe Lys Phe Tyr Lys Ser Gly Val Tyr Ser
                325                 330                 335
```

```
Ser Asp Gln Cys Arg Val Pro Asn His Ala Val Leu Val Val Gly Tyr
        340                 345                 350

Gly Thr Ser Gln Lys Thr Arg Asp Tyr Trp Ile Ile Lys Asn Ser Trp
        355                 360                 365

Gly Thr Asn Trp Ala Arg Asn Gly Tyr Gly Tyr Met Lys Arg Asn Glu
        370                 375             380

Arg Asn Met Cys His Ile Ala Thr Met Ala Ser Phe Pro Ile
385             390                 395

(2) INFORMATION FOR SEQ ID NO:3:

(i) SEQUENCE CHARACTERISTICS:
        (A) LENGTH: 942 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..942

(xi) SEQUENCE DESCRIPTION: SEQ ID NO:3:
```

| | |
|---|---|
| ATG AAA AAA TTA GAA ACC GAA TGG CAA GAG TAT TTA ACA GCT CTT GGA<br>Met Lys Lys Leu Glu Thr Glu Trp Gln Glu Tyr Leu Thr Ala Leu Gly<br>1               5                  10                  15 | 48 |
| AAA GAA TAT GAT TCA GAA GAG AAT AAA TTG AGA ATG GCA ATA TTT GAA<br>Lys Glu Tyr Asp Ser Glu Glu Asn Lys Leu Arg Met Ala Ile Phe Glu<br>            20                  25                  30 | 96 |
| AGT AAT GAA TTA ATG ACA GAA GCA TTA AAT AGA AAA TAT GAG CAA GGC<br>Ser Asn Glu Leu Met Thr Glu Ala Leu Asn Arg Lys Tyr Glu Gln Gly<br>        35                  40                  45 | 144 |
| TTA ATT TCA TTT AAA ACT GCC CTG AAT GAT ATG GCT GAT TTG ACC GAT<br>Leu Ile Ser Phe Lys Thr Ala Leu Asn Asp Met Ala Asp Leu Thr Asp<br>    50                  55                  60 | 192 |
| CAA GAA TTC AAC CTA ATG AAT GGA CTT CTA CTG CAT AAT GAA ACT TCC<br>Gln Glu Phe Asn Leu Met Asn Gly Leu Leu Leu His Asn Glu Thr Ser<br>65                  70                  75                  80 | 240 |
| CAT ACA AGA AGG TAT GCT CGA CAA GTA TCT GGT GAA TTT CTC AAG TAC<br>His Thr Arg Arg Tyr Ala Arg Gln Val Ser Gly Glu Phe Leu Lys Tyr<br>                85                  90                  95 | 288 |
| AAT AAG AGT ACA AAG CTG CCA AAA TAT GTT GAT TGG AGA AAG AGA GGA<br>Asn Lys Ser Thr Lys Leu Pro Lys Tyr Val Asp Trp Arg Lys Arg Gly<br>            100                 105                 110 | 336 |
| TAT GTC ACA CCT GCC AAA GAG CAG GGC TTG TGT GGT AGT TGT TAT GCA<br>Tyr Val Thr Pro Ala Lys Glu Gln Gly Leu Cys Gly Ser Cys Tyr Ala<br>        115                 120                 125 | 384 |
| TTC TGC AGC TGC AGC ATT AGA AGC CTT ATA TAT AAA AAG ACG AAA AAC<br>Phe Cys Ser Cys Ser Ile Arg Ser Leu Ile Tyr Lys Lys Thr Lys Asn<br>    130                 135                 140 | 432 |
| AAA CTT CTC GAT TTA TCT CCG CAA AAT ATT CTA GAT TGT ACA TGG GAT<br>Lys Leu Leu Asp Leu Ser Pro Gln Asn Ile Leu Asp Cys Thr Trp Asp<br>145                 150                 155                 160 | 480 |
| CTC GGT AAT AAT GGT TGC CAT GGT GGT TTC ATG AAT CCG GCA TTT TAT<br>Leu Gly Asn Asn Gly Cys His Gly Gly Phe Met Asn Pro Ala Phe Tyr<br>                165                 170                 175 | 528 |
| TAT GCA AGT AAG GCA GGT ATT GCA TCA GAA GCG AAA TAT CCG TAT GTT<br>Tyr Ala Ser Lys Ala Gly Ile Ala Ser Glu Ala Lys Tyr Pro Tyr Val<br>            180                 185                 190 | 576 |
| CAC ACT GCA AGA CGT ACA TGC TAT TGG CGG AAA GAT ATA GTT GCT GCT | 624 |

-continued

```
His Thr Ala Arg Arg Thr Cys Tyr Trp Arg Lys Asp Ile Val Ala Ala
            195                 200                 205

ACT GAT AAT GGT TAC ACT CGA ATA CAA CAA GGT GAT GAG AAA GGT CTC      672
Thr Asp Asn Gly Tyr Thr Arg Ile Gln Gln Gly Asp Glu Lys Gly Leu
210                 215                 220

AAT ATG CTG TGG CAA TTG ACC GTT GTT GTT GGA ATT TCT GGA TAT CAA      720
Asn Met Leu Trp Gln Leu Thr Val Val Val Gly Ile Ser Gly Tyr Gln
225                 230                 235                 240

CAC GAT TTT AAA TTT TAT AAA TCC GGT GTC TAC TCT AGT GAT CAA TGT      768
His Asp Phe Lys Phe Tyr Lys Ser Gly Val Tyr Ser Ser Asp Gln Cys
                245                 250                 255

CGT GTT CCT AAT CAC GCA GTA CTG GTT GTT GGT TAT GGA ACC AGT CAA      816
Arg Val Pro Asn His Ala Val Leu Val Val Gly Tyr Gly Thr Ser Gln
                260                 265                 270

AAA ACA CGG GAT TAT TGG ATT ATT AAA AAT AGT TGG GGA ACT AAT TGG      864
Lys Thr Arg Asp Tyr Trp Ile Ile Lys Asn Ser Trp Gly Thr Asn Trp
            275                 280                 285

GCA AGA AAT GGA TAT GGT TAT ATG AAG CGA AAC GAA AGG AAT ATG TGT      912
Ala Arg Asn Gly Tyr Gly Tyr Met Lys Arg Asn Glu Arg Asn Met Cys
290                 295                 300

CAT ATC GCT ACG ATG GCT TCA TTC CCC ATA                              942
His Ile Ala Thr Met Ala Ser Phe Pro Ile
305                 310
```

(2) INFORMATION FOR SEQ ID NO:4:

(i) SEQUENCE CHARACTERISTICS:
        (A) LENGTH: 314 amino acids
        (B) TYPE: amino acid
        (D) TOPOLOGY: linear (ii) MOLECULE TYPE: protein (xi) SEQUENCE DESCRIPTION: SEQ ID NO:4:

```
Met Lys Lys Leu Glu Thr Glu Trp Gln Glu Tyr Leu Thr Ala Leu Gly
1               5                   10                  15

Lys Glu Tyr Asp Ser Glu Glu Asn Lys Leu Arg Met Ala Ile Phe Glu
                20                  25                  30

Ser Asn Glu Leu Met Thr Glu Ala Leu Asn Arg Lys Tyr Glu Gln Gly
            35                  40                  45

Leu Ile Ser Phe Lys Thr Ala Leu Asn Asp Met Ala Asp Leu Thr Asp
        50                  55                  60

Gln Glu Phe Asn Leu Met Asn Gly Leu Leu His Asn Glu Thr Ser
65                  70                  75                  80

His Thr Arg Arg Tyr Ala Arg Gln Val Ser Gly Glu Phe Leu Lys Tyr
                85                  90                  95

Asn Lys Ser Thr Lys Leu Pro Lys Tyr Val Asp Trp Arg Lys Arg Gly
                100                 105                 110

Tyr Val Thr Pro Ala Lys Glu Gln Gly Leu Cys Gly Ser Cys Tyr Ala
            115                 120                 125

Phe Cys Ser Cys Ser Ile Arg Ser Leu Ile Tyr Lys Lys Thr Lys Asn
        130                 135                 140

Lys Leu Leu Asp Leu Ser Pro Gln Asn Ile Leu Asp Cys Thr Trp Asp
145                 150                 155                 160

Leu Gly Asn Asn Gly Cys His Gly Gly Phe Met Asn Pro Ala Phe Tyr
                165                 170                 175

Tyr Ala Ser Lys Ala Gly Ile Ala Ser Glu Ala Lys Tyr Pro Tyr Val
            180                 185                 190
```

```
His Thr Ala Arg Arg Thr Cys Tyr Trp Arg Lys Asp Ile Val Ala Ala
        195                 200                 205

Thr Asp Asn Gly Tyr Thr Arg Ile Gln Gln Gly Asp Glu Lys Gly Leu
    210                 215                 220

Asn Met Leu Trp Gln Leu Thr Val Val Gly Ile Ser Gly Tyr Gln
225                 230                 235                 240

His Asp Phe Lys Phe Tyr Lys Ser Gly Val Tyr Ser Ser Asp Gln Cys
                245                 250                 255

Arg Val Pro Asn His Ala Val Leu Val Val Gly Tyr Gly Thr Ser Gln
            260                 265                 270

Lys Thr Arg Asp Tyr Trp Ile Ile Lys Asn Ser Trp Gly Thr Asn Trp
        275                 280                 285

Ala Arg Asn Gly Tyr Gly Tyr Met Lys Arg Asn Glu Arg Asn Met Cys
290                 295                 300

His Ile Ala Thr Met Ala Ser Phe Pro Ile
305                 310
```

(2) INFORMATION FOR SEQ ID NO:5:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..219

(xi) SEQUENCE DESCRIPTION: SEQ ID NO:5:

```
T ATG AGA TTC TAT AAA TCC GGT GTT TAT TCT AAT CGT GAC TGT GGT        46
  Met Arg Phe Tyr Lys Ser Gly Val Tyr Ser Asn Arg Asp Cys Gly
  1               5                  10                  15

GAT CTT AAT CAC GCA GTA CTA CTT GTC GGT TAT GGC AAG CAT AAA ACA      94
Asp Leu Asn His Ala Val Leu Leu Val Gly Tyr Gly Lys His Lys Thr
                20                  25                  30

TAC GGA GAA TAC TGG ATT ATT AAA AAC AGC TGG GGA ACT GAT TGG GGA      142
Tyr Gly Glu Tyr Trp Ile Ile Lys Asn Ser Trp Gly Thr Asp Trp Gly
            35                  40                  45

AGA AAA GGA TAC GCT TAT ATG GCG CGA AAT AAG GGG AAC ATG TGC CAC      190
Arg Lys Gly Tyr Ala Tyr Met Ala Arg Asn Lys Gly Asn Met Cys His
        50                  55                  60

ATC GCA ACG TTG GCT TCA ATA CCC ATA TA AAAATGATTA AATTTGATTT         239
Ile Ala Thr Leu Ala Ser Ile Pro Ile
        65                  70

TGAATAGTAT TTATTGGCCA AATTCTAACT TTCATCTATG TTTGAGGGCA AT            291
```

(2) INFORMATION FOR SEQ ID NO:6:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO:6:

```
Met Arg Phe Tyr Lys Ser Gly Val Tyr Ser Asn Arg Asp Cys Gly Asp
1               5                  10                  15

Leu Asn His Ala Val Leu Leu Val Gly Tyr Gly Lys His Lys Thr Tyr
```

```
            20                  25                  30
Gly Glu Tyr Trp Ile Ile Lys Asn Ser Trp Gly Thr Asp Trp Gly Arg
            35                  40                  45

Lys Gly Tyr Ala Tyr Met Ala Arg Asn Lys Gly Asn Met Cys His Ile
        50                  55                  60

Ala Thr Leu Ala Ser Ile Pro Ile
 65                  70
```

(2) INFORMATION FOR SEQ ID NO:7:

(i) SEQUENCE CHARACTERISTICS:
        (A) LENGTH: 216 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
TTTAGATTCT ATAAATCCGG TGTTTATTCT AATCGTGACT GTGGTGATCT TAATCACGCA      60

GTACTACTTG TCGGTTATGG CAAGCATAAA ACATACGGAG AATACTGGAT TATTAAAAAC     120

AGCTGGGGAA CTGATTGGGG AAGAAAAGGA TACGCTTATA TGGCGCGAAA TAAGGGGAAC     180

ATGTGCCACA TCGCAACGTT GGCTTCAATA CCCATA                               216
```

(2) INFORMATION FOR SEQ ID NO:8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
AACGGTGAGG ATCCAGCGAT GAAAAAATTA GAAAC                                35
```

(2) INFORMATION FOR SEQ ID NO:9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
ATTAAAAGAT CTTTATATGG GGAATGAAGC CATCG                                35
```

(2) INFORMATION FOR SEQ ID NO:10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
CGCGGATCCT ATAAATATGA AAAAATTAGA AACC                                 34
```

(2) INFORMATION FOR SEQ ID NO:11:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

CGCGGATCCT TATATGGGGA ATGAAGC                                    27

(2) INFORMATION FOR SEQ ID NO:12:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..17
            (D) OTHER INFORMATION: /label= primer (xi) SEQUENCE DESCRIPTION: SEQ ID NO:12:

CATGTTCCCC TTATTTC                                                17

(2) INFORMATION FOR SEQ ID NO:13:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..17
            (D) OTHER INFORMATION: /label= primer (xi) SEQUENCE DESCRIPTION: SEQ ID NO:13:

CATGTTCCCC TTATTTC                                                17

(2) INFORMATION FOR SEQ ID NO:14:

(i) SEQUENCE CHARACTERISTICS:
            (A) LENGTH: 1306 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 2..1223

(xi) SEQUENCE DESCRIPTION: SEQ ID NO:14:

C AGA AGC AGA AAA AAA CTC ATG CTT CGG ATC ATT GTT TTA CTG ATC     46
  Arg Ser Arg Lys Lys Leu Met Leu Arg Ile Ile Val Leu Leu Ile
   1               5                  10                  15

GTA TTC GCC TTC CTA GTC GAT TTT ACT GTC ACA CTC AAT GCC CAA GTG   94
Val Phe Ala Phe Leu Val Asp Phe Thr Val Thr Leu Asn Ala Gln Val
                 20                  25                  30

CAA CAG CTA CGA GAA GTT CTA GGA ACA TTT GAT CAA GAT TAC AAG CGA   142

```
                                                                -continued

Gln Gln Leu Arg Glu Val Leu Gly Thr Phe Asp Gln Asp Tyr Lys Arg
         35                  40                  45

GGC AAT ATG ACG AGG CTT ACG ACT GAT TTC AAA AAA GCA GTA AAA AAA      190
Gly Asn Met Thr Arg Leu Thr Thr Asp Phe Lys Lys Ala Val Lys Lys
         50                  55                  60

TAC GGC GAT GGA AAA GAA AGT CAA AAA TCA ACC GTT CTG CAA TCT TTT      238
Tyr Gly Asp Gly Lys Glu Ser Gln Lys Ser Thr Val Leu Gln Ser Phe
 65                  70                  75

CTT CAA AAA ATG GAA GAC AAT GGC GAG CTA CGA GCT ATG GAG AAA TTA      286
Leu Gln Lys Met Glu Asp Asn Gly Glu Leu Arg Ala Met Glu Lys Leu
 80                  85                  90                  95

GAA ACC GAA TGG AAT GAT TAC GTA ATG GCT CTC GGA AAA CAC TAC GAC      334
Glu Thr Glu Trp Asn Asp Tyr Val Met Ala Leu Gly Lys His Tyr Asp
                 100                 105                 110

TCA AAT GAG TCC AAT TTG AGA ATG GCA ATA TTT GAA AGT AAT GAA TTA      382
Ser Asn Glu Ser Asn Leu Arg Met Ala Ile Phe Glu Ser Asn Glu Leu
             115                 120                 125

ATG ACA GAA GCC ACA AAT AGA AAA TAT GAA CAA GGC CTA ATT TCT TAT      430
Met Thr Glu Ala Thr Asn Arg Lys Tyr Glu Gln Gly Leu Ile Ser Tyr
         130                 135                 140

ACA AAT GGT CTG AAT CAC TTG GCT GAT TTG ACC GAC GAA GAA TTC AAA      478
Thr Asn Gly Leu Asn His Leu Ala Asp Leu Thr Asp Glu Glu Phe Lys
     145                 150                 155

ATG ATG AAT GGA CTT CGT TTT CCC AAT GAA ACT CAT CTT CGA ACA AGA      526
Met Met Asn Gly Leu Arg Phe Pro Asn Glu Thr His Leu Arg Thr Arg
160                 165                 170                 175

AGG CAG ACT CGT CAT ACT GTA GGT CAA AAA TAT ACG TAC GAT CCA AAT      574
Arg Gln Thr Arg His Thr Val Gly Gln Lys Tyr Thr Tyr Asp Pro Asn
                 180                 185                 190

GAG AAA CTG CCG GTG TCG GTT GAC TGG AGA AAG AAA GGC ATG GTC ACA      622
Glu Lys Leu Pro Val Ser Val Asp Trp Arg Lys Lys Gly Met Val Thr
             195                 200                 205

CCC GTC AAA AAT CAA GGA GTG TGT GGC AGC TGC TAT CGA TTC GCT GCA      670
Pro Val Lys Asn Gln Gly Val Cys Gly Ser Cys Tyr Arg Phe Ala Ala
         210                 215                 220

ATA GGT GCA TTG GAA GCT TAT AAT AAG AAA AAG ACA GGG AAA CTT GTC      718
Ile Gly Ala Leu Glu Ala Tyr Asn Lys Lys Lys Thr Gly Lys Leu Val
     225                 230                 235

GAT TTA TCC ATC CAA AAT GCT GTT GAC TGC ACA TGG ACG TTG GGT AAC      766
Asp Leu Ser Ile Gln Asn Ala Val Asp Cys Thr Trp Thr Leu Gly Asn
240                 245                 250                 255

TAT GGC TGT CGT GGT GGC TAT ATG AAT CCA ATT TTC TAT TAT GCA ACG      814
Tyr Gly Cys Arg Gly Gly Tyr Met Asn Pro Ile Phe Tyr Tyr Ala Thr
                 260                 265                 270

AAG TTT GGA TTA GCG ATG GAA TCG AAA TAT CCG TAC GTT GGG ACT GAA      862
Lys Phe Gly Leu Ala Met Glu Ser Lys Tyr Pro Tyr Val Gly Thr Glu
             275                 280                 285

CAA AAA TGC AAA TGG CAA GAG AAA ATT TGT TAC GCC ACT GAT AAG GGT      910
Gln Lys Cys Lys Trp Gln Glu Lys Ile Cys Tyr Ala Thr Asp Lys Gly
         290                 295                 300

TAC GCT GCA ATA CAA AGG GGT GAT GAA TTA GGA CTT ATG CAT GCT GTG      958
Tyr Ala Ala Ile Gln Arg Gly Asp Glu Leu Gly Leu Met His Ala Val
     305                 310                 315

GCT AAG CAT GGA CCC GTT GTT GTT GGA ATT AAC GGA TCA AAG CGT CCT     1006
Ala Lys His Gly Pro Val Val Val Gly Ile Asn Gly Ser Lys Arg Pro
320                 325                 330                 335

TTT AGA TTC TAT AAA TCC GGT GTT TAT TCT AAT CGT GAC TGT GGT GAT     1054
Phe Arg Phe Tyr Lys Ser Gly Val Tyr Ser Asn Arg Asp Cys Gly Asp
                 340                 345                 350
```

```
CTT AAT CAC GCA GTA CTA CTT GTC GGT TAT GGC AAG CAT AAA ACG TAC       1102
Leu Asn His Ala Val Leu Leu Val Gly Tyr Gly Lys His Lys Thr Tyr
        355                 360                 365

GGA GAA TAC TGG ATT ATT AAA AAC AGC TGG GGA ACT GAT TGG GGA AGA       1150
Gly Glu Tyr Trp Ile Ile Lys Asn Ser Trp Gly Thr Asp Trp Gly Arg
        370                 375                 380

AAA GGA TAC GCT TAT ATG GCG CGA AAT AAG GGG AAC ATG TGC CAC ATC       1198
Lys Gly Tyr Ala Tyr Met Ala Arg Asn Lys Gly Asn Met Cys His Ile
385                 390                 395

GCA ACG TTG GCT TCA ATA CCC ATA T AAAAATGATT AAATTTGATT               1243
Ala Thr Leu Ala Ser Ile Pro Ile
400                 405

TTGAATAGTA TTTATTGGCC AAATTCTAAC TTTCATCTAT GTTTGAGGGC AATAATTTGC     1303

GGC                                                                   1306

(2) INFORMATION FOR SEQ ID NO:15:

(i) SEQUENCE CHARACTERISTICS:
        (A) LENGTH: 407 amino acids
        (B) TYPE: amino acid
        (D) TOPOLOGY: linear (ii) MOLECULE TYPE: protein (xi) SEQUENCE DESCRIPTION: SEQ ID NO:15:

Arg Ser Arg Lys Lys Leu Met Leu Arg Ile Ile Val Leu Leu Ile Val
1               5                   10                  15

Phe Ala Phe Leu Val Asp Phe Val Thr Leu Asn Ala Gln Val Gln
                20                  25                  30

Gln Leu Arg Glu Val Leu Gly Thr Phe Asp Gln Asp Tyr Lys Arg Gly
            35                  40                  45

Asn Met Thr Arg Leu Thr Thr Asp Phe Lys Lys Ala Val Lys Lys Tyr
        50                  55                  60

Gly Asp Gly Lys Glu Ser Gln Lys Ser Thr Val Leu Gln Ser Phe Leu
65                  70                  75                  80

Gln Lys Met Glu Asp Asn Gly Glu Leu Arg Ala Met Glu Lys Leu Glu
                85                  90                  95

Thr Glu Trp Asn Asp Tyr Val Met Ala Leu Gly Lys His Tyr Asp Ser
            100                 105                 110

Asn Glu Ser Asn Leu Arg Met Ala Ile Phe Glu Ser Asn Glu Leu Met
        115                 120                 125

Thr Glu Ala Thr Asn Arg Lys Tyr Glu Gln Gly Leu Ile Ser Tyr Thr
    130                 135                 140

Asn Gly Leu Asn His Leu Ala Asp Leu Thr Asp Glu Glu Phe Lys Met
145                 150                 155                 160

Met Asn Gly Leu Arg Phe Pro Asn Glu Thr His Leu Arg Thr Arg Arg
                165                 170                 175

Gln Thr Arg His Thr Val Gly Gln Lys Tyr Thr Tyr Asp Pro Asn Glu
            180                 185                 190

Lys Leu Pro Val Ser Val Asp Trp Arg Lys Lys Gly Met Val Thr Pro
        195                 200                 205

Val Lys Asn Gln Gly Val Cys Gly Ser Cys Tyr Arg Phe Ala Ala Ile
    210                 215                 220

Gly Ala Leu Glu Ala Tyr Asn Lys Lys Thr Gly Lys Leu Val Asp
225                 230                 235                 240

Leu Ser Ile Gln Asn Ala Val Asp Cys Thr Trp Thr Leu Gly Asn Tyr
                245                 250                 255
```

```
Gly Cys Arg Gly Gly Tyr Met Asn Pro Ile Phe Tyr Tyr Ala Thr Lys
            260                 265                 270

Phe Gly Leu Ala Met Glu Ser Lys Tyr Pro Tyr Val Gly Thr Glu Gln
            275                 280                 285

Lys Cys Lys Trp Gln Glu Lys Ile Cys Tyr Ala Thr Asp Lys Gly Tyr
            290                 295                 300

Ala Ala Ile Gln Arg Gly Asp Glu Leu Gly Leu Met His Ala Val Ala
305                 310                 315                 320

Lys His Gly Pro Val Val Gly Ile Asn Gly Ser Lys Arg Pro Phe
            325                 330                 335

Arg Phe Tyr Lys Ser Gly Val Tyr Ser Asn Arg Asp Cys Gly Asp Leu
            340                 345                 350

Asn His Ala Val Leu Val Gly Tyr Gly Lys His Lys Thr Tyr Gly
            355                 360                 365

Glu Tyr Trp Ile Ile Lys Asn Ser Trp Gly Thr Asp Trp Gly Arg Lys
            370                 375                 380

Gly Tyr Ala Tyr Met Ala Arg Asn Lys Gly Asn Met Cys His Ile Ala
385                 390                 395                 400

Thr Leu Ala Ser Ile Pro Ile
            405

(2) INFORMATION FOR SEQ ID NO:16:

(i) SEQUENCE CHARACTERISTICS:
        (A) LENGTH: 1203 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1203

(xi) SEQUENCE DESCRIPTION: SEQ ID NO:16:

ATG CTT CGG ATC ATT GTT TTA CTG ATC GTA TTC GCC TTC CTA GTC GAT      48
Met Leu Arg Ile Ile Val Leu Leu Ile Val Phe Ala Phe Leu Val Asp
 1               5                  10                  15

TTT ACT GTC ACA CTC AAT GCC CAA GTG CAA CAG CTA CGA GAA GTT CTA      96
Phe Thr Val Thr Leu Asn Ala Gln Val Gln Gln Leu Arg Glu Val Leu
                 20                  25                  30

GGA ACA TTT GAT CAA GAT TAC AAG CGA GGC AAT ATG ACG AGG CTT ACG     144
Gly Thr Phe Asp Gln Asp Tyr Lys Arg Gly Asn Met Thr Arg Leu Thr
             35                  40                  45

ACT GAT TTC AAA AAA GCA GTA AAA AAA TAC GGC GAT GGA AAA GAA AGT     192
Thr Asp Phe Lys Lys Ala Val Lys Lys Tyr Gly Asp Gly Lys Glu Ser
         50                  55                  60

CAA AAA TCA ACC GTT CTG CAA TCT TTT CTT CAA AAA ATG GAA GAC AAT     240
Gln Lys Ser Thr Val Leu Gln Ser Phe Leu Gln Lys Met Glu Asp Asn
 65                  70                  75                  80

GGC GAG CTA CGA GCT ATG GAG AAA TTA GAA ACC GAA TGG AAT GAT TAC     288
Gly Glu Leu Arg Ala Met Glu Lys Leu Glu Thr Glu Trp Asn Asp Tyr
                 85                  90                  95

GTA ATG GCT CTC GGA AAA CAC TAC GAC TCA AAT GAG TCC AAT TTG AGA     336
Val Met Ala Leu Gly Lys His Tyr Asp Ser Asn Glu Ser Asn Leu Arg
                100                 105                 110

ATG GCA ATA TTT GAA AGT AAT GAA TTA ATG ACA GAA GCC ACA AAT AGA     384
Met Ala Ile Phe Glu Ser Asn Glu Leu Met Thr Glu Ala Thr Asn Arg
            115                 120                 125
```

```
AAA TAT GAA CAA GGC CTA ATT TCT TAT ACA AAT GGT CTG AAT CAC TTG      432
Lys Tyr Glu Gln Gly Leu Ile Ser Tyr Thr Asn Gly Leu Asn His Leu
    130                 135                 140

GCT GAT TTG ACC GAC GAA GAA TTC AAA ATG ATG AAT GGA CTT CGT TTT      480
Ala Asp Leu Thr Asp Glu Glu Phe Lys Met Met Asn Gly Leu Arg Phe
145                 150                 155                 160

CCC AAT GAA ACT CAT CTT CGA ACA AGA AGG CAG ACT CGT CAT ACT GTA      528
Pro Asn Glu Thr His Leu Arg Thr Arg Arg Gln Thr Arg His Thr Val
                165                 170                 175

GGT CAA AAA TAT ACG TAC GAT CCA AAT GAG AAA CTG CCG GTG TCG GTT      576
Gly Gln Lys Tyr Thr Tyr Asp Pro Asn Glu Lys Leu Pro Val Ser Val
            180                 185                 190

GAC TGG AGA AAG AAA GGC ATG GTC ACA CCC GTC AAA AAT CAA GGA GTG      624
Asp Trp Arg Lys Lys Gly Met Val Thr Pro Val Lys Asn Gln Gly Val
        195                 200                 205

TGT GGC AGC TGC TAT CGA TTC GCT GCA ATA GGT GCA TTG GAA GCT TAT      672
Cys Gly Ser Cys Tyr Arg Phe Ala Ala Ile Gly Ala Leu Glu Ala Tyr
    210                 215                 220

AAT AAG AAA AAG ACA GGG AAA CTT GTC GAT TTA TCC ATC CAA AAT GCT      720
Asn Lys Lys Lys Thr Gly Lys Leu Val Asp Leu Ser Ile Gln Asn Ala
225                 230                 235                 240

GTT GAC TGC ACA TGG ACG TTG GGT AAC TAT GGC TGT CGT GGT GGC TAT      768
Val Asp Cys Thr Trp Thr Leu Gly Asn Tyr Gly Cys Arg Gly Gly Tyr
                245                 250                 255

ATG AAT CCA ATT TTC TAT TAT GCA ACG AAG TTT GGA TTA GCG ATG GAA      816
Met Asn Pro Ile Phe Tyr Tyr Ala Thr Lys Phe Gly Leu Ala Met Glu
            260                 265                 270

TCG AAA TAT CCG TAC GTT GGG ACT GAA CAA AAA TGC AAA TGG CAA GAG      864
Ser Lys Tyr Pro Tyr Val Gly Thr Glu Gln Lys Cys Lys Trp Gln Glu
        275                 280                 285

AAA ATT TGT TAC GCC ACT GAT AAG GGT TAC GCT GCA ATA CAA AGG GGT      912
Lys Ile Cys Tyr Ala Thr Asp Lys Gly Tyr Ala Ala Ile Gln Arg Gly
    290                 295                 300

GAT GAA TTA GGA CTT ATG CAT GCT GTG GCT AAG CAT GGA CCC GTT GTT      960
Asp Glu Leu Gly Leu Met His Ala Val Ala Lys His Gly Pro Val Val
305                 310                 315                 320

GTT GGA ATT AAC GGA TCA AAG CGT CCT TTT AGA TTC TAT AAA TCC GGT     1008
Val Gly Ile Asn Gly Ser Lys Arg Pro Phe Arg Phe Tyr Lys Ser Gly
                325                 330                 335

GTT TAT TCT AAT CGT GAC TGT GGT GAT CTT AAT CAC GCA GTA CTA CTT     1056
Val Tyr Ser Asn Arg Asp Cys Gly Asp Leu Asn His Ala Val Leu Leu
            340                 345                 350

GTC GGT TAT GGC AAG CAT AAA ACG TAC GGA GAA TAC TGG ATT ATT AAA     1104
Val Gly Tyr Gly Lys His Lys Thr Tyr Gly Glu Tyr Trp Ile Ile Lys
        355                 360                 365

AAC AGC TGG GGA ACT GAT TGG GGA AGA AAA GGA TAC GCT TAT ATG GCG     1152
Asn Ser Trp Gly Thr Asp Trp Gly Arg Lys Gly Tyr Ala Tyr Met Ala
    370                 375                 380

CGA AAT AAG GGG AAC ATG TGC CAC ATC GCA ACG TTG GCT TCA ATA CCC     1200
Arg Asn Lys Gly Asn Met Cys His Ile Ala Thr Leu Ala Ser Ile Pro
385                 390                 395                 400

ATA                                                                 1203
Ile
```

(2) INFORMATION FOR SEQ ID NO:17:

(i) SEQUENCE CHARACTERISTICS:
        (A) LENGTH: 401 amino acids
        (B) TYPE: amino acid
        (D) TOPOLOGY: linear (ii) MOLECULE TYPE: protein (xi) SEQUENCE DESCRIPTION: SEQ ID NO:17:

| | | | | | | | | | | | | | | |
|---|---|---|---|---|---|---|---|---|---|---|---|---|---|---|
| Met | Leu | Arg | Ile | Ile | Val | Leu | Leu | Ile | Val | Phe | Ala | Phe | Leu | Val | Asp |
| 1 | | | | 5 | | | | | 10 | | | | | 15 |

Phe Thr Val Thr Leu Asn Ala Gln Val Gln Gln Leu Arg Glu Val Leu
            20                  25                  30

Gly Thr Phe Asp Gln Asp Tyr Lys Arg Gly Asn Met Thr Arg Leu Thr
                35                  40                  45

Thr Asp Phe Lys Lys Ala Val Lys Lys Tyr Gly Asp Gly Lys Glu Ser
        50                  55                  60

Gln Lys Ser Thr Val Leu Gln Ser Phe Leu Gln Lys Met Glu Asp Asn
65                  70                  75                  80

Gly Glu Leu Arg Ala Met Glu Lys Leu Glu Thr Glu Trp Asn Asp Tyr
                85                  90                  95

Val Met Ala Leu Gly Lys His Tyr Asp Ser Asn Glu Ser Asn Leu Arg
                100                 105                 110

Met Ala Ile Phe Glu Ser Asn Glu Leu Met Thr Glu Ala Thr Asn Arg
            115                 120                 125

Lys Tyr Glu Gln Gly Leu Ile Ser Tyr Thr Asn Gly Leu Asn His Leu
130                 135                 140

Ala Asp Leu Thr Asp Glu Glu Phe Lys Met Met Asn Gly Leu Arg Phe
145                 150                 155                 160

Pro Asn Glu Thr His Leu Arg Thr Arg Arg Gln Thr Arg His Thr Val
                165                 170                 175

Gly Gln Lys Tyr Thr Tyr Asp Pro Asn Glu Lys Leu Pro Val Ser Val
            180                 185                 190

Asp Trp Arg Lys Lys Gly Met Val Thr Pro Val Lys Asn Gln Gly Val
            195                 200                 205

Cys Gly Ser Cys Tyr Arg Phe Ala Ala Ile Gly Ala Leu Glu Ala Tyr
            210                 215                 220

Asn Lys Lys Lys Thr Gly Lys Leu Val Asp Leu Ser Ile Gln Asn Ala
225                 230                 235                 240

Val Asp Cys Thr Trp Thr Leu Gly Asn Tyr Gly Cys Arg Gly Gly Tyr
            245                 250                 255

Met Asn Pro Ile Phe Tyr Tyr Ala Thr Lys Phe Gly Leu Ala Met Glu
            260                 265                 270

Ser Lys Tyr Pro Tyr Val Gly Thr Glu Gln Lys Cys Lys Trp Gln Glu
            275                 280                 285

Lys Ile Cys Tyr Ala Thr Asp Lys Gly Tyr Ala Ala Ile Gln Arg Gly
            290                 295                 300

Asp Glu Leu Gly Leu Met His Ala Val Ala Lys His Gly Pro Val Val
305                 310                 315                 320

Val Gly Ile Asn Gly Ser Lys Arg Pro Phe Arg Phe Tyr Lys Ser Gly
            325                 330                 335

Val Tyr Ser Asn Arg Asp Cys Gly Asp Leu Asn His Ala Val Leu Leu
            340                 345                 350

Val Gly Tyr Gly Lys His Lys Thr Tyr Gly Glu Tyr Trp Ile Ile Lys
            355                 360                 365

Asn Ser Trp Gly Thr Asp Trp Gly Arg Lys Gly Tyr Ala Tyr Met Ala
            370                 375                 380

Arg Asn Lys Gly Asn Met Cys His Ile Ala Thr Leu Ala Ser Ile Pro
385                 390                 395                 400

Ile (2) INFORMATION FOR SEQ ID NO:18:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: misc_feature
       (B) LOCATION: 1..30
       (D) OTHER INFORMATION: /label= primer (xi) SEQUENCE DESCRIPTION: SEQ ID NO:18:

CGGGGTACCA GGAAATATGA CGAGACTTAC                                         30

(2) INFORMATION FOR SEQ ID NO:19:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: misc_feature
       (B) LOCATION: 1..27

(xi) SEQUENCE DESCRIPTION: SEQ ID NO:19:

CGGGGTACCT TATATGGGGA ATGAAGC                                            27

(2) INFORMATION FOR SEQ ID NO:20:

(i) SEQUENCE CHARACTERISTICS:
       (A) LENGTH: 49 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: misc_feature
       (B) LOCATION: 1..49

(xi) SEQUENCE DESCRIPTION: SEQ ID NO:20:

GATCCAATTG GATCAGCTTT TTTTTTTTTT TTTTTGGCAT ATAAATAAG                    49

(2) INFORMATION FOR SEQ ID NO:21:

(i) SEQUENCE CHARACTERISTICS:
       (A) LENGTH: 49 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: misc_feature
       (B) LOCATION: 1..49

(xi) SEQUENCE DESCRIPTION: SEQ ID NO:21:

GTACCTTATT TATATGCCAA AAAAAAAAAA AAAAAGCTG ATCCAATTG                     49

(2) INFORMATION FOR SEQ ID NO:22:

(i) SEQUENCE CHARACTERISTICS:
      (A) LENGTH: 213 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:22:

```
Leu Pro Lys Tyr Val Asp Trp Arg Lys Arg Gly Tyr Val Thr Pro Ala
1               5                   10                  15

Lys Glu Gln Gly Leu Cys Gly Ser Cys Tyr Ala Phe Cys Ser Cys Ser
                20                  25                  30

Ile Arg Ser Leu Ile Tyr Lys Lys Thr Lys Asn Lys Leu Leu Asp Leu
            35                  40                  45

Ser Pro Gln Asn Ile Leu Asp Cys Thr Trp Asp Leu Gly Asn Asn Gly
    50                  55                  60

Cys His Gly Gly Phe Met Asn Pro Ala Phe Tyr Tyr Ala Ser Lys Ala
65                  70                  75                  80

Gly Ile Ala Ser Glu Ala Lys Tyr Pro Tyr Val His Thr Ala Arg Arg
                85                  90                  95

Thr Cys Tyr Trp Arg Lys Asp Ile Val Ala Ala Thr Asp Asn Gly Tyr
                100                 105                 110

Thr Arg Ile Gln Gln Gly Asp Glu Lys Gly Leu Asn Met Leu Trp Gln
            115                 120                 125

Leu Thr Val Val Val Gly Ile Ser Gly Tyr Gln His Asp Phe Lys Phe
    130                 135                 140

Tyr Lys Ser Gly Val Tyr Ser Ser Asp Gln Cys Arg Val Pro Asn His
145                 150                 155                 160

Ala Val Leu Val Val Gly Tyr Gly Thr Ser Gln Lys Thr Arg Asp Tyr
                165                 170                 175

Trp Ile Ile Lys Asn Ser Trp Gly Thr Asn Trp Ala Arg Asn Gly Tyr
                180                 185                 190

Gly Tyr Met Lys Arg Asn Glu Arg Asn Met Cys His Ile Ala Thr Met
            195                 200                 205

Ala Ser Phe Pro Ile
    210
```

(2) INFORMATION FOR SEQ ID NO:23:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: 1..32

(xi) SEQUENCE DESCRIPTION: SEQ ID NO:23:

ACTGGATCCG CAAGTGCAAC AGCTACGAGA AG                              32

(2) INFORMATION FOR SEQ ID NO:24:

(i) SEQUENCE CHARACTERISTICS:

(A) LENGTH: 63 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..63

(xi) SEQUENCE DESCRIPTION: SEQ ID NO:24:

TAAGGTACCT TATATGGGTA TTGAAGCCAA CGTTGCGATG TGGCACATGT TCCCCTTATT    60

TCG                                                                63

(2) INFORMATION FOR SEQ ID NO:25:

(i) SEQUENCE CHARACTERISTICS:
        (A) LENGTH: 356 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: CDS
        (B) LOCATION: 1..1172

(xi) SEQUENCE DESCRIPTION: SEQ ID NO:25:

Met Thr Arg Leu Thr Phe Asp Phe Gln Asn Ala Leu Lys Asp Tyr Gly
1               5                   10                  15

Asp Gly Glu Asn Ser Tyr Lys Leu Thr Ala Val Gln Ser Phe Leu Lys
            20                  25                  30

Lys Leu Glu Glu Asn Gly Glu Glu Gln Ala Met Lys Lys Leu Glu Thr
        35                  40                  45

Glu Trp Gln Glu Tyr Leu Thr Ala Leu Gly Lys Glu Tyr Asp Ser Glu
    50                  55                  60

Glu Asn Lys Leu Arg Met Ala Ile Phe Glu Ser Asn Glu Leu Met Thr
65                  70                  75                  80

Glu Ala Leu Asn Arg Lys Tyr Glu Gln Gly Leu Ile Ser Phe Lys Thr
                85                  90                  95

Ala Leu Asn Asp Met Ala Asp Leu Thr Asp Gln Glu Phe Asn Leu Met
            100                 105                 110

Asn Gly Leu Leu Leu His Asn Glu Thr Ser His Thr Arg Arg Tyr Ala
        115                 120                 125

Arg Gln Val Ser Gly Glu Phe Leu Lys Tyr Asn Lys Ser Thr Lys Leu
    130                 135                 140

Pro Lys Tyr Val Asp Trp Arg Lys Arg Gly Tyr Val Thr Pro Ala Lys
145                 150                 155                 160

Glu Gln Gly Leu Cys Gly Ser Cys Tyr Ala Phe Cys Ser Cys Ser Ile
                165                 170                 175

Arg Ser Leu Ile Tyr Lys Lys Thr Lys Asn Lys Leu Leu Asp Leu Ser
            180                 185                 190

Pro Gln Asn Ile Leu Asp Cys Thr Trp Asp Leu Gly Asn Asn Gly Cys
        195                 200                 205

His Gly Gly Phe Met Asn Pro Ala Phe Tyr Tyr Ala Ser Lys Ala Gly
    210                 215                 220

Ile Ala Ser Glu Ala Lys Tyr Pro Tyr Val His Thr Ala Arg Arg Thr
225                 230                 235                 240

```
Cys Tyr Trp Arg Lys Asp Ile Val Ala Ala Thr Asp Asn Gly Tyr Thr
                245                 250                 255
Arg Ile Gln Gln Gly Asp Glu Lys Gly Leu Asn Met Leu Trp Gln Leu
            260                 265                 270
Thr Val Val Gly Ile Ser Gly Tyr Gln His Asp Phe Lys Phe Tyr
        275                 280                 285
Lys Ser Gly Val Tyr Ser Ser Asp Gln Cys Arg Val Pro Asn His Ala
    290                 295                 300
Val Leu Val Val Gly Tyr Gly Thr Ser Gln Lys Thr Arg Asp Tyr Trp
305                 310                 315                 320
Ile Ile Lys Asn Ser Trp Gly Thr Asn Trp Ala Arg Asn Gly Tyr Gly
                325                 330                 335
Tyr Met Lys Arg Asn Glu Arg Asn Met Cys His Ile Ala Thr Met Ala
            340                 345                 350
Ser Phe Pro Ile
        355
```

(2) INFORMATION FOR SEQ ID NO:26:

(i) SEQUENCE CHARACTERISTICS:
        (A) LENGTH: 1298 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
TTTTTTTTTT TTTTTTTCCC AATTTCTTTT TATTAAACCA AAATTATCAA ATATTGAAAA      60
TTAGCAAAAT AAATATTTTT CGAAAACAAA TTAAATCATA ATTATATGGG GAATGAAGCC     120
ATCGTAGCGA TATGACACAT ATTCCTTTCG TTTCGCTTCA TATAACCATA TCCATTTCTT     180
GCCCAATTAG TTCCCCAACT ATTTTTAATA ATCCAATAAT CCCGTGTTTT TTGACTGGTT     240
CCATAACCAA CAACCAGTAC TGCGTGATTA GGAACACGAC ATTGATCACT AGAGTAGACA     300
CCGGATTTAT AAAATTTAAA ATCGTGTTGA TATCCAGAAA TTCCAACAAC AACGGTCAAT     360
TGCCACAGCA TATTGAGACC TTTCTCATCA CCTTGTTGTA TTCGAGTGTA ACCATTATCA     420
GTAGCAGCAA CTATATCTTT CCGCCAATAG CATGTACGTC TTGCAGTGTG AACATACGGA     480
TATTTCGCTT CTGATGCAAT ACCTGCCTTA CTTGCATAAT AAAATGCCGG ATTCATGAAA     540
CCACCATGGC AACCATTATT ACCGAGATCC CATGTACAAT CTAGAATATT TTGCGGAGAT     600
AAATCGAGAA GTTTGTTTTT CGTCTTTTTA TATATAAGGC TTCTAATGCT GCAGCTGCAG     660
AATGCATAAC AACTACCACA CAAGCCCTGC TCTTTGGCAG GTGTGACATA TCCTCTCTTT     720
CTCCAATCAA CATATTTTGG CAGCTTTGTA CTCTTATTGT ACTTGAGAAA TTCACCAGAT     780
ACTTGTCGAG CATACCTTCT TGTATGGGAA GTTTCATTAT GCAGTAGAAG TCCATTCATT     840
AGGTTGAATT CTTGATCGGT CAAATCAGCC ATATCATTCA GGGCAGTTTT AAATGAAATT     900
AAGCCTTGCT CATATTTTCT ATTTAATGCT TCTGTCATTA ATTCATTACT TTCAAATATT     960
GCCATTCTCA ATTTATTCTC TTCTGAATCA TATTCTTTTC CAAGAGCTGT TAAATACTCT    1020
TGCCATTCGG TTTCTAATTT TTTCATCGCT TGTTCCTCAC CGTTTTCTTC TAATTTTTTG    1080
AGGAAAGATT GCACAGCAGT TAGTTTATAA CTGTTTTCTC CATCGCCGTA ATCTTTCAAA    1140
GCGTTTTGAA AATCAAACGT AAGTCTCGTC ATATTTCCTA ATCTGTAATC TTCATCAAAC    1200
ATTCCCAATA CTTCTTTCAG CTGTAGAATT TCATCATTGA ATGAGACGGT AAAGTCGATC    1260
```

```
AAGAAAGTGA GTATGGCCAA TAAAGCAATG AATCGAAG                                1298

(2) INFORMATION FOR SEQ ID NO:27:

(i) SEQUENCE CHARACTERISTICS:
        (A) LENGTH: 1046 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

TTTTTTTTTT TTTTTTTCCC AATTTCTTTT TATTAAACCA AAATTATCAA ATATTGAAAA    60

TTAGCAAAAT AAATATTTTT CGAAAACAAA TTAAATCATA ATTATATGGG GAATGAAGCC   120

ATCGTAGCGA TATGACACAT ATTCCTTTCG TTTCGCTTCA TATAACCATA TCCATTTCTT   180

GCCCAATTAG TTCCCCAACT ATTTTTAATA ATCCAATAAT CCCGTGTTTT TTGACTGGTT   240

CCATAACCAA CAACCAGTAC TGCGTGATTA GGAACACGAC ATTGATCACT AGAGTAGACA   300

CCGGATTTAT AAAATTTAAA ATCGTGTTGA TATCCAGAAA TTCCAACAAC AACGGTCAAT   360

TGCCACAGCA TATTGAGACC TTTCTCATCA CCTTGTTGTA TTCGAGTGTA ACCATTATCA   420

GTAGCAGCAA CTATATCTTT CCGCCAATAG CATGTACGTC TTGCAGTGTG AACATACGGA   480

TATTTCGCTT CTGATGCAAT ACCTGCCTTA CTTGCATAAT AAAATGCCGG ATTCATGAAA   540

CCACCATGGC AACCATTATT ACCGAGATCC CATGTACAAT CTAGAATATT TTGCGGAGAT   600

AAATCGAGAA GTTTGTTTTT CGTCTTTTTA TATATAAGGC TTCTAATGCT GCAGCTGCAG   660

AATGCATAAC AACTACCACA CAAGCCCTGC TCTTTGGCAG GTGTGACATA TCCTCTCTTT   720

CTCCAATCAA CATATTTTGG CAGCTTTGTA CTCTTATTGT ACTTGAGAAA TTCACCAGAT   780

ACTTGTCGAG CATACCTTCT TGTATGGGAA GTTTCATTAT GCAGTAGAAG TCCATTCATT   840

AGGTTGAATT CTTGATCGGT CAAATCAGCC ATATCATTCA GGGCAGTTTT AAATGAAATT   900

AAGCCTTGCT CATATTTTCT ATTTAATGCT TCTGTCATTA ATTCATTACT TTCAAATATT   960

GCCATTCTCA ATTTATTCTC TTCTGAATCA TATTCTTTTC CAAGAGCTGT TAAATACTCT  1020

TGCCATTCGG TTTCTAATTT TTTCAT                                      1046

(2) INFORMATION FOR SEQ ID NO:28:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

ATTGCCCTCA ACATAGATG AAAGTTAGAA TTTGGCCAAT AAATACTATT CAAAATCAAA     60

TTTAATCATT TTTATATGGG TATTGAAGCC AACGTTGCGA TGTGGCACAT GTTCCCCTTA   120

TTTCGCGCCA TATAAGCGTA TCCTTTTCTT CCCCAATCAG TTCCCCAGCT GTTTTTAATA   180

ATCCAGTATT CTCCGTATGT TTTATGCTTG CCATAACCGA CAAGTAGTAC TGCGTGATTA   240

AGATCACCAC AGTCACGATT AGAATAAACA CCGGATTTAT AGAATCTAAA A           291

(2) INFORMATION FOR SEQ ID NO:29:

(i) SEQUENCE CHARACTERISTICS:
        (A) LENGTH: 216 base pairs
```

(B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

| | | | | | |
|---|---|---|---|---|---|
| TATGGGTATT | GAAGCCAACG | TTGCGATGTG | GCACATGTTC | CCCTTATTTC | GCGCCATATA | 60 |
| AGCGTATCCT | TTTCTTCCCC | AATCAGTTCC | CCAGCTGTTT | TTAATAATCC | AGTATTCTCC | 120 |
| GTATGTTTTA | TGCTTGCCAT | AACCGACAAG | TAGTACTGCG | TGATTAAGAT | CACCACAGTC | 180 |
| ACGATTAGAA | TAAACACCGG | ATTTATAGAA | TCTAAA | | | 216 |

(2) INFORMATION FOR SEQ ID NO:30:

(i) SEQUENCE CHARACTERISTICS:
        (A) LENGTH: 1306 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

| | | | | | |
|---|---|---|---|---|---|
| GCCGCAAATT | ATTGCCCTCA | AACATAGATG | AAAGTTAGAA | TTTGGCCAAT | AAATACTATT | 60 |
| CAAAATCAAA | TTTAATCATT | TTTATATGGG | TATTGAAGCC | AACGTTGCGA | TGTGGCACAT | 120 |
| GTTCCCCTTA | TTTCGCGCCA | TATAAGCGTA | TCCTTTTCTT | CCCCAATCAG | TTCCCCAGCT | 180 |
| GTTTTTAATA | ATCCAGTATT | CTCCGTACGT | TTTATGCTTG | CCATAACCGA | CAAGTAGTAC | 240 |
| TGCGTGATTA | AGATCACCAC | AGTCACGATT | AGAATAAACA | CCGGATTTAT | AGAATCTAAA | 300 |
| AGGACGCTTT | GATCCGTTAA | TTCCAACAAC | AACGGGTCCA | TGCTTAGCCA | CAGCATGCAT | 360 |
| AAGTCCTAAT | TCATCACCCC | TTTGTATTGC | AGCGTAACCC | TTATCAGTGG | CGTAACAAAT | 420 |
| TTTCTCTTGC | CATTTGCATT | TTTGTTCAGT | CCCAACGTAC | GGATATTTCG | ATTCCATCGC | 480 |
| TAATCCAAAC | TTCGTTGCAT | AATAGAAAAT | TGGATTCATA | TAGCCACCAC | GACAGCCATA | 540 |
| GTTACCCAAC | GTCCATGTGC | AGTCAACAGC | ATTTTGGATG | GATAAATCGA | CAAGTTTCCC | 600 |
| TGTCTTTTTC | TTATTATAAG | CTTCCAATGC | ACCTATTGCA | GCGAATCGAT | AGCAGCTGCC | 660 |
| ACACACTCCT | TGATTTTTGA | CGGGTGTGAC | CATGCCTTTC | TTTCTCCAGT | CAACCGACAC | 720 |
| CGGCAGTTTC | TCATTTGGAT | CGTACGTATA | TTTTTGACCT | ACAGTATGAC | GAGTCTGCCT | 780 |
| TCTTGTTCGA | AGATGAGTTT | CATTGGGAAA | ACGAAGTCCA | TTCATCATTT | TGAATTCTTC | 840 |
| GTCGGTCAAA | TCAGCCAAGT | GATTCAGACC | ATTTGTATAA | GAAATTAGGC | CTTGTTCATA | 900 |
| TTTTCTATTT | GTGGCTTCTG | TCATTAATTC | ATTACTTTCA | AATATTGCCA | TTCTCAAATT | 960 |
| GGACTCATTT | GAGTCGTAGT | GTTTTCCGAG | AGCCATTACG | TAATCATTCC | ATTCGGTTTC | 1020 |
| TAATTTCTCC | ATAGCTCGTA | GCTCGCCATT | GTCTTCCATT | TTTTGAAGAA | AAGATTGCAG | 1080 |
| AACGGTTGAT | TTTGACTTT | CTTTTCCATC | GCCGTATTTT | TTTACTGCTT | TTTTGAAATC | 1140 |
| AGTCGTAAGC | CTCGTCATAT | TGCCTCGCTT | GTAATCTTGA | TCAAATGTTC | CTAGAACTTC | 1200 |
| TCGTAGCTGT | TGCACTTGGG | CATTGAGTGT | GACAGTAAAA | TCGACTAGGA | AGGCGAATAC | 1260 |
| GATCAGTAAA | ACAATGATCC | GAAGCATGAG | TTTTTTTCTG | CTTCTG | | 1306 |

(2) INFORMATION FOR SEQ ID NO:31:

(i) SEQUENCE CHARACTERISTICS:
        (A) LENGTH: 1203 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:31:

```
TATGGGTATT GAAGCCAACG TTGCGATGTG GCACATGTTC CCCTTATTTC GCGCCATATA      60

AGCGTATCCT TTTCTTCCCC AATCAGTTCC CCAGCTGTTT TAATAATCC AGTATTCTCC       120

GTACGTTTTA TGCTTGCCAT AACCGACAAG TAGTACTGCG TGATTAAGAT CACCACAGTC      180

ACGATTAGAA TAAACACCGG ATTTATAGAA TCTAAAAGGA CGCTTTGATC CGTTAATTCC      240

AACAACAACG GGTCCATGCT TAGCCACAGC ATGCATAAGT CCTAATTCAT CACCCCTTTG      300

TATTGCAGCG TAACCCTTAT CAGTGGCGTA ACAAATTTTC TCTTGCCATT TGCATTTTTG      360

TTCAGTCCCA ACGTACGGAT ATTTCGATTC CATCGCTAAT CCAAACTTCG TTGCATAATA      420

GAAAATTGGA TTCATATAGC CACCACGACA GCCATAGTTA CCCAACGTCC ATGTGCAGTC      480

AACAGCATTT TGGATGGATA AATCGACAAG TTTCCCTGTC TTTTTCTTAT TATAAGCTTC      540

CAATGCACCT ATTGCAGCGA ATCGATAGCA GCTGCCACAC ACTCCTTGAT TTTTGACGGG      600

TGTGACCATG CCTTTCTTTC TCCAGTCAAC CGACACCGGC AGTTTCTCAT TTGGATCGTA      660

CGTATATTTT TGACCTACAG TATGACGAGT CTGCCTTCTT GTTCGAAGAT GAGTTTCATT      720

GGGAAAACGA AGTCCATTCA TCATTTTGAA TTCTTCGTCG GTCAAATCAG CCAAGTGATT      780

CAGACCATTT GTATAAGAAA TTAGGCCTTG TTCATATTTT CTATTTGTGG CTTCTGTCAT      840

TAATTCATTA CTTTCAAATA TTGCCATTCT CAAATTGGAC TCATTTGAGT CGTAGTGTTT      900

TCCGAGAGCC ATTACGTAAT CATTCCATTC GGTTTCTAAT TTCTCCATAG CTCGTAGCTC      960

GCCATTGTCT TCCATTTTTT GAAGAAAAGA TTGCAGAACG GTTGATTTTT GACTTTCTTT     1020

TCCATCGCCG TATTTTTTA CTGCTTTTTT GAAATCAGTC GTAAGCCTCG TCATATTGCC      1080

TCGCTTGTAA TCTTGATCAA ATGTTCCTAG AACTTCTCGT AGCTGTTGCA CTTGGGCATT     1140

GAGTGTGACA GTAAAATCGA CTAGGAAGGC GAATACGATC AGTAAAACAA TGATCCGAAG     1200

CAT                                                                  1203
```

(2) INFORMATION FOR SEQ ID NO:32:

(i) SEQUENCE CHARACTERISTICS:
        (A) LENGTH: 1304 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1202

(xi) SEQUENCE DESCRIPTION: SEQ ID NO:32:

```
CTT CGA TTC ATT GCT TTA TTG GCC ATA CTC ACT TTC TTG ATC GAC TTT       48
Leu Arg Phe Ile Ala Leu Leu Ala Ile Leu Thr Phe Leu Ile Asp Phe
  1               5                  10                  15

ACC GTC TCA TTC AAT GAT GAA ATT CTA CAG CTG AAA GAA GTA TTG GGA       96
Thr Val Ser Phe Asn Asp Glu Ile Leu Gln Leu Lys Glu Val Leu Gly
                 20                  25                  30

ATG TTT GAT GAA GAT TAC AGA TTA GGA AAT ATG ACG AGA CTT ACG TTT      144
Met Phe Asp Glu Asp Tyr Arg Leu Gly Asn Met Thr Arg Leu Thr Phe
             35                  40                  45

GAT TTT CAA AAC GCT TTG AAA GAT TAC GGC GAT GGA GAA AAC AGT TAT      192
```

```
                                      -continued

Asp Phe Gln Asn Ala Leu Lys Asp Tyr Gly Asp Gly Glu Asn Ser Tyr
 50                  55                  60

AAA CTA ACT GCT GTG CAA TCT TTC CTC AAA AAA TTA GAA GAA AAC GGT        240
Lys Leu Thr Ala Val Gln Ser Phe Leu Lys Lys Leu Glu Glu Asn Gly
 65                  70                  75                  80

GAG GAA CAA GCG ATG AAA AAA TTA GAA ACC GAA TGG CAA GAG TAT TTA        288
Glu Glu Gln Ala Met Lys Lys Leu Glu Thr Glu Trp Gln Glu Tyr Leu
                 85                  90                  95

ACA GCT CTT GGA AAA GAA TAT GAT TCA GAA GAG AAT AAA TTG AGA ATG        336
Thr Ala Leu Gly Lys Glu Tyr Asp Ser Glu Glu Asn Lys Leu Arg Met
             100                 105                 110

GCA ATA TTT GAA AGT AAT GAA TTA ATG ACA GAA GCA TTA AAT AGA AAA        384
Ala Ile Phe Glu Ser Asn Glu Leu Met Thr Glu Ala Leu Asn Arg Lys
         115                 120                 125

TAT GAG CAA GGC TTA ATT TCA TTT AAA ACT GCC CTG AAT GAT ATG GCT        432
Tyr Glu Gln Gly Leu Ile Ser Phe Lys Thr Ala Leu Asn Asp Met Ala
     130                 135                 140

GAT TTG ACC GAT CAA GAA TTC AAC CTA ATG AAT GGA CTT CTA CTG CAT        480
Asp Leu Thr Asp Gln Glu Phe Asn Leu Met Asn Gly Leu Leu Leu His
145                 150                 155                 160

AAT GAA ACT TCC CAT ACA AGA AGG TAT GCT CGA CAA GTA TCT GGT GAA        528
Asn Glu Thr Ser His Thr Arg Arg Tyr Ala Arg Gln Val Ser Gly Glu
                165                 170                 175

TTT CTC AAG TAC AAT AAG AGT ACA AAG CTG CCA AAA TAT GTT GAT TGG        576
Phe Leu Lys Tyr Asn Lys Ser Thr Lys Leu Pro Lys Tyr Val Asp Trp
            180                 185                 190

AGA AAG AGA GGA TAT GTC ACA CCT GCC AAA GAG CAG GGC TTG TGT GGT        624
Arg Lys Arg Gly Tyr Val Thr Pro Ala Lys Glu Gln Gly Leu Cys Gly
        195                 200                 205

AGT TGT TAT GCA TTC GCT GCA GCT GCA GCA TTA GAA GCT TAT AAT AAA        672
Ser Cys Tyr Ala Phe Ala Ala Ala Ala Leu Glu Ala Tyr Asn Lys
    210                 215                 220

AAG ACG AAA AAC AAA CTT CTC GAT TTA TCT CCG CAA AAT ATT CTA GAT        720
Lys Thr Lys Asn Lys Leu Leu Asp Leu Ser Pro Gln Asn Ile Leu Asp
225                 230                 235                 240

TGT ACA TGG GAT CTC GGT AAT AAT GGT TGC CAT GGT GGT TTC ATG AAT        768
Cys Thr Trp Asp Leu Gly Asn Asn Gly Cys His Gly Gly Phe Met Asn
                245                 250                 255

CCG GCA TTT TAT TAT GCA AGT AAG GCA GGT ATT GCA TCA GAA GCG AAA        816
Pro Ala Phe Tyr Tyr Ala Ser Lys Ala Gly Ile Ala Ser Glu Ala Lys
            260                 265                 270

TAT CCG TAT GTT CAC ACT GCA AGA CGT ACA TGC TAT TGG CGG AAA GAT        864
Tyr Pro Tyr Val His Thr Ala Arg Arg Thr Cys Tyr Trp Arg Lys Asp
        275                 280                 285

ATA GTT GCT GCT ACT GAT AAT GGT TAC ACT CGA ATA CAA CAA GGT GAT        912
Ile Val Ala Ala Thr Asp Asn Gly Tyr Thr Arg Ile Gln Gln Gly Asp
    290                 295                 300

GAG AAA GGT CTT CAA TAT GCT GTG GCT AAA TTT GGA CCC GTT GTT GTT        960
Glu Lys Gly Leu Gln Tyr Ala Val Ala Lys Phe Gly Pro Val Val Val
305                 310                 315                 320

GGA ATT TCT GGA TAT CAA CAC GAT TTT AAA TTT TAT AAA TCC GGT GTC       1008
Gly Ile Ser Gly Tyr Gln His Asp Phe Lys Phe Tyr Lys Ser Gly Val
                325                 330                 335

TAC TCT AGT GAT CAA TGT CGT GTT CCT AAT CAC GCA GTA CTG GTT GTT       1056
Tyr Ser Ser Asp Gln Cys Arg Val Pro Asn His Ala Val Leu Val Val
            340                 345                 350

GGT TAT GGA ACC AGT AAA AAA CAC GGG GAT TAT TGG ATT ATT AAA AAT       1104
Gly Tyr Gly Thr Ser Lys Lys His Gly Asp Tyr Trp Ile Ile Lys Asn
        355                 360                 365
```

```
AGT TGG GGA ACT AAT TGG GGA AGA AAT GGA TAT GGT TAT ATG AAG CGA      1152
Ser Trp Gly Thr Asn Trp Gly Arg Asn Gly Tyr Gly Tyr Met Lys Arg
    370                 375                 380

AAC GAA AGG AAT ATG TGT CAT ATC GCT ACG ATG GCT TCA TTC CCC ATA TA   1202
Asn Glu Arg Asn Met Cys His Ile Ala Thr Met Ala Ser Phe Pro Ile
385                 390                 395                 400

ATTATGATTT AATTTGTTTT CGAAAAATAT TTATTTTGCT AATTTTCAAT ATTTGATAAT    1262

TTTGGTTTAA TAAAAAGAAA TTGGGAAAAA AAAAAAAAAA AA                      1304
```

(2) INFORMATION FOR SEQ ID NO:33:

(i) SEQUENCE CHARACTERISTICS:
        (A) LENGTH: 400 amino acids
        (B) TYPE: amino acid
        (D) TOPOLOGY: linear (ii) MOLECULE TYPE: protein (xi) SEQUENCE DESCRIPTION: SEQ ID NO:33:

```
Leu Arg Phe Ile Ala Leu Leu Ala Ile Leu Thr Phe Leu Ile Asp Phe
  1               5                  10                  15

Thr Val Ser Phe Asn Asp Glu Ile Leu Gln Leu Lys Glu Val Leu Gly
                 20                  25                  30

Met Phe Asp Glu Asp Tyr Arg Leu Gly Asn Met Thr Arg Leu Thr Phe
             35                  40                  45

Asp Phe Gln Asn Ala Leu Lys Asp Tyr Gly Asp Gly Glu Asn Ser Tyr
         50                  55                  60

Lys Leu Thr Ala Val Gln Ser Phe Leu Lys Lys Leu Glu Glu Asn Gly
 65                  70                  75                  80

Glu Glu Gln Ala Met Lys Lys Leu Glu Thr Glu Trp Gln Glu Tyr Leu
                 85                  90                  95

Thr Ala Leu Gly Lys Glu Tyr Asp Ser Glu Glu Asn Lys Leu Arg Met
            100                 105                 110

Ala Ile Phe Glu Ser Asn Glu Leu Met Thr Glu Ala Leu Asn Arg Lys
        115                 120                 125

Tyr Glu Gln Gly Leu Ile Ser Phe Lys Thr Ala Leu Asn Asp Met Ala
    130                 135                 140

Asp Leu Thr Asp Gln Glu Phe Asn Leu Met Asn Gly Leu Leu Leu His
145                 150                 155                 160

Asn Glu Thr Ser His Thr Arg Arg Tyr Ala Arg Gln Val Ser Gly Glu
                165                 170                 175

Phe Leu Lys Tyr Asn Lys Ser Thr Lys Leu Pro Lys Tyr Val Asp Trp
            180                 185                 190

Arg Lys Arg Gly Tyr Val Thr Pro Ala Lys Glu Gln Gly Leu Cys Gly
        195                 200                 205

Ser Cys Tyr Ala Phe Ala Ala Ala Ala Leu Glu Ala Tyr Asn Lys
    210                 215                 220

Lys Thr Lys Asn Lys Leu Leu Asp Leu Ser Pro Gln Asn Ile Leu Asp
225                 230                 235                 240

Cys Thr Trp Asp Leu Gly Asn Asn Gly Cys His Gly Gly Phe Met Asn
                245                 250                 255

Pro Ala Phe Tyr Tyr Ala Ser Lys Ala Gly Ile Ala Ser Glu Ala Lys
            260                 265                 270

Tyr Pro Tyr Val His Thr Ala Arg Arg Thr Cys Tyr Trp Arg Lys Asp
        275                 280                 285

Ile Val Ala Ala Thr Asp Asn Gly Tyr Thr Arg Ile Gln Gln Gly Asp
```

```
            290               295               300
Glu Lys Gly Leu Gln Tyr Ala Val Ala Lys Phe Gly Pro Val Val Val
305               310               315               320

Gly Ile Ser Gly Tyr Gln His Asp Phe Lys Phe Tyr Lys Ser Gly Val
                325               330               335

Tyr Ser Ser Asp Gln Cys Arg Val Pro Asn His Ala Val Leu Val Val
                340               345               350

Gly Tyr Gly Thr Ser Lys Lys His Gly Asp Tyr Trp Ile Ile Lys Asn
                355               360               365

Ser Trp Gly Thr Asn Trp Gly Arg Asn Gly Tyr Gly Tyr Met Lys Arg
370               375               380

Asn Glu Arg Asn Met Cys His Ile Ala Thr Met Ala Ser Phe Pro Ile
385               390               395               400

(2) INFORMATION FOR SEQ ID NO:34:

(i) SEQUENCE CHARACTERISTICS:
        (A) LENGTH: 1200 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

CTTCGATTCA TTGCTTTATT GGCCATACTC ACTTTCTTGA TCGACTTTAC CGTCTCATTC      60

AATGATGAAA TTCTACAGCT GAAAGAAGTA TTGGGAATGT TTGATGAAGA TTACAGATTA     120

GGAAATATGA CGAGACTTAC GTTTGATTTT CAAAACGCTT TGAAAGATTA CGGCGATGGA     180

GAAAACAGTT ATAAACTAAC TGCTGTGCAA TCTTTCCTCA AAAAATTAGA AGAAAACGGT     240

GAGGAACAAG CGATGAAAAA ATTAGAAACC GAATGGCAAG AGTATTTAAC AGCTCTTGGA     300

AAAGAATATG ATTCAGAAGA GAATAAATTG AGAATGGCAA TATTTGAAAG TAATGAATTA     360

ATGACAGAAG CATTAAATAG AAAATATGAG CAAGGCTTAA TTTCATTTAA AACTGCCCTG     420

AATGATATGG CTGATTTGAC CGATCAAGAA TTCAACCTAA TGAATGGACT TCTACTGCAT     480

AATGAAACTT CCCATACAAG AAGGTATGCT CGACAAGTAT CTGGTGAATT TCTCAAGTAC     540

AATAAGAGTA CAAAGCTGCC AAAATATGTT GATTGGAGAA AGAGAGGATA TGTCACACCT     600

GCCAAAGAGC AGGGCTTGTG TGGTAGTTGT TATGCATTCG CTGCAGCTGC AGCATTAGAA     660

GCTTATAATA AAAAGACGAA AAACAAACTT CTCGATTTAT CTCCGCAAAA TATTCTAGAT     720

TGTACATGGG ATCTCGGTAA TAATGGTTGC CATGGTGGTT TCATGAATCC GGCATTTTAT     780

TATGCAAGTA AGGCAGGTAT TGCATCAGAA GCGAAATATC CGTATGTTCA CACTGCAAGA     840

CGTACATGCT ATTGGCGGAA AGATATAGTT GCTGCTACTG ATAATGGTTA CACTCGAATA     900

CAACAAGGTG ATGAGAAAGG TCTTCAATAT GCTGTGGCTA AATTTGGACC CGTTGTTGTT     960

GGAATTTCTG GATATCAACA CGATTTTAAA TTTTATAAAT CCGGTGTCTA CTCTAGTGAT    1020

CAATGTCGTG TTCCTAATCA CGCAGTACTG GTTGTTGGTT ATGGAACCAG TAAAAAACAC    1080

GGGGATTATT GGATTATTAA AAATAGTTGG GGAACTAATT GGGGAAGAAA TGGATATGGT    1140

TATATGAAGC GAAACGAAAG GAATATGTGT CATATCGCTA CGATGGCTTC ATTCCCCATA    1200

(2) INFORMATION FOR SEQ ID NO:35:

(i) SEQUENCE CHARACTERISTICS:
        (A) LENGTH: 1304 base pairs
        (B) TYPE: nucleic acid
```

```
        (C) STRANDEDNESS: single
        (D) TOPOLOGY: linear (ii) MOLECULE TYPE: DNA (genomic)

(xi) SEQUENCE DESCRIPTION: SEQ ID NO:35:

TTTTTTTTTT TTTTTTTCCC AATTTCTTTT TATTAAACCA AAATTATCAA ATATTGAAAA      60

TTAGCAAAAT AAATATTTTT CGAAAACAAA TTAAATCATA ATTATATGGG GAATGAAGCC     120

ATCGTAGCGA TATGCACAT ATTCCTTTCG TTTCGCTTCA TATAACCATA TCCATTTCTT      180

CCCCAATTAG TTCCCCAACT ATTTTTAATA ATCCAATAAT CCCCGTGTTT TTTACTGGTT     240

CCATAACCAA CAACCAGTAC TGCGTGATTA GGAACACGAC ATTGATCACT AGAGTAGACA     300

CCGGATTTAT AAAATTTAAA ATCGTGTTGA TATCCAGAAA TTCCAACAAC AACGGGTCCA     360

AATTTAGCCA CAGCATATTG AAGACCTTTC TCATCACCTT GTTGTATTCG AGTGTAACCA     420

TTATCAGTAG CAGCAACTAT ATCTTTCCGC CAATAGCATG TACGTCTTGC AGTGTGAACA     480

TACGGATATT TCGCTTCTGA TGCAATACCT GCCTTACTTG CATAATAAAA TGCCGGATTC     540

ATGAAACCAC CATGGCAACC ATTATTACCG AGATCCCATG TACAATCTAG AATATTTTGC     600

GGAGATAAAT CGAGAAGTTT GTTTTTCGTC TTTTTATTAT AAGCTTCTAA TGCTGCAGCT     660

GCAGCGAATG CATAACAACT ACCACACAAG CCCTGCTCTT TGGCAGGTGT GACATATCCT     720

CTCTTTCTCC AATCAACATA TTTTGGCAGC TTTGTACTCT TATTGTACTT GAGAAATTCA     780

CCAGATACTT GTCGAGCATA CCTTCTTGTA TGGGAAGTTT CATTATGCAG TAGAAGTCCA     840

TTCATTAGGT TGAATTCTTG ATCGGTCAAA TCAGCCATAT CATTCAGGGC AGTTTTAAAT     900

GAAATTAAGC CTTGCTCATA TTTTCTATTT AATGCTTCTG TCATTAATTC ATTACTTTCA     960

AATATTGCCA TTCTCAATTT ATTCTCTTCT GAATCATATT CTTTTCCAAG AGCTGTTAAA    1020

TACTCTTGCC ATTCGGTTTC TAATTTTTTC ATCGCTTGTT CCTCACCGTT TTCTTCTAAT    1080

TTTTTGAGGA AAGATTGCAC AGCAGTTAGT TTATAACTGT TTTCTCCATC GCCGTAATCT    1140

TTCAAAGCGT TTTGAAAATC AAACGTAAGT CTCGTCATAT TTCCTAATCT GTAATCTTCA    1200

TCAAACATTC CCAATACTTC TTTCAGCTGT AGAATTTCAT CATTGAATGA GACGGTAAAG    1260

TCGATCAAGA AAGTGAGTAT GGCCAATAAA GCAATGAATC GAAG                     1304

(2) INFORMATION FOR SEQ ID NO:36:

(i) SEQUENCE CHARACTERISTICS:
        (A) LENGTH: 1200 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

TATGGGGAAT GAAGCCATCG TAGCGATATG ACACATATTC CTTTCGTTTC GCTTCATATA      60

ACCATATCCA TTTCTTCCCC AATTAGTTCC CCAACTATTT TTAATAATCC AATAATCCCC     120

GTGTTTTTA CTGGTTCCAT AACCAACAAC CAGTACTGCG TGATTAGGAA CACGACATTG      180

ATCACTAGAG TAGACACCGG ATTTATAAAA TTTAAAATCG TGTTGATATC CAGAAATTCC     240

AACAACAACG GTCCAAATT TAGCCACAGC ATATTGAAGA CCTTTCTCAT CACCTTGTTG      300

TATTCGAGTG TAACCATTAT CAGTAGCAGC AACTATATCT TTCCGCCAAT AGCATGTACG     360

TCTTGCAGTG TGAACATACG GATATTTCGC TTCTGATGCA ATACCTGCCT TACTTGCATA     420

ATAAAATGCC GGATTCATGA AACCACCATG GCAACCATTA TTACCGAGAT CCCATGTACA     480
```

-continued

```
ATCTAGAATA TTTTGCGGAG ATAAATCGAG AAGTTTGTTT TTCGTCTTTT TATTATAAGC     540

TTCTAATGCT GCAGCTGCAG CGAATGCATA ACAACTACCA CACAAGCCCT GCTCTTTGGC     600

AGGTGTGACA TATCCTCTCT TTCTCCAATC AACATATTTT GGCAGCTTTG TACTCTTATT     660

GTACTTGAGA AATTCACCAG ATACTTGTCG AGCATACCTT CTTGTATGGG AAGTTTCATT     720

ATGCAGTAGA AGTCCATTCA TTAGGTTGAA TTCTTGATCG GTCAAATCAG CCATATCATT     780

CAGGGCAGTT TTAAATGAAA TTAAGCCTTG CTCATATTTT CTATTTAATG CTTCTGTCAT     840

TAATTCATTA CTTTCAAATA TTGCCATTCT CAATTTATTC TCTTCTGAAT CATATTCTTT     900

TCCAAGAGCT GTTAAATACT CTTGCCATTC GGTTTCTAAT TTTTTCATCG CTTGTTCCTC     960

ACCGTTTTCT TCTAATTTTT TGAGGAAAGA TTGCACAGCA GTTAGTTTAT AACTGTTTTC    1020

TCCATCGCCG TAATCTTTCA AAGCGTTTTG AAAATCAAAC GTAAGTCTCG TCATATTTCC    1080

TAATCTGTAA TCTTCATCAA ACATTCCCAA TACTTCTTTC AGCTGTAGAA TTTCATCATT    1140

GAATGAGACG GTAAAGTCGA TCAAGAAAGT GAGTATGGCC AATAAAGCAA TGAATCGAAG    1200
```

(2) INFORMATION FOR SEQ ID NO:37:

(i) SEQUENCE CHARACTERISTICS:
        (A) LENGTH: 645 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..645

(xi) SEQUENCE DESCRIPTION: SEQ ID NO:37:

```
CTG CCA AAA TAT GTT GAT TGG AGA AAG AGA GGA TAT GTC ACA CCT GCC      48
Leu Pro Lys Tyr Val Asp Trp Arg Lys Arg Gly Tyr Val Thr Pro Ala
  1               5                  10                  15

AAA GAG CAG GGC TTG TGT GGT AGT TGT TAT GCA TTC GCT GCA GCT GCA      96
Lys Glu Gln Gly Leu Cys Gly Ser Cys Tyr Ala Phe Ala Ala Ala Ala
             20                  25                  30

GCA TTA GAA GCT TAT AAT AAA AAG ACG AAA AAC AAA CTT CTC GAT TTA     144
Ala Leu Glu Ala Tyr Asn Lys Lys Thr Lys Asn Lys Leu Leu Asp Leu
         35                  40                  45

TCT CCG CAA AAT ATT CTA GAT TGT ACA TGG GAT CTC GGT AAT AAT GGT     192
Ser Pro Gln Asn Ile Leu Asp Cys Thr Trp Asp Leu Gly Asn Asn Gly
 50                  55                  60

TGC CAT GGT GGT TTC ATG AAT CCG GCA TTT TAT TAT GCA AGT AAG GCA     240
Cys His Gly Gly Phe Met Asn Pro Ala Phe Tyr Tyr Ala Ser Lys Ala
 65                  70                  75                  80

GGT ATT GCA TCA GAA GCG AAA TAT CCG TAT GTT CAC ACT GCA AGA CGT     288
Gly Ile Ala Ser Glu Ala Lys Tyr Pro Tyr Val His Thr Ala Arg Arg
                 85                  90                  95

ACA TGC TAT TGG CGG AAA GAT ATA GTT GCT GCT ACT GAT AAT GGT TAC     336
Thr Cys Tyr Trp Arg Lys Asp Ile Val Ala Ala Thr Asp Asn Gly Tyr
            100                 105                 110

ACT CGA ATA CAA CAA GGT GAT GAG AAA GGT CTT CAA TAT GCT GTG GCT     384
Thr Arg Ile Gln Gln Gly Asp Glu Lys Gly Leu Gln Tyr Ala Val Ala
        115                 120                 125

AAA TTT GGA CCC GTT GTT GTT GGA ATT TCT GGA TAT CAA CAC GAT TTT     432
Lys Phe Gly Pro Val Val Val Gly Ile Ser Gly Tyr Gln His Asp Phe
    130                 135                 140

AAA TTT TAT AAA TCC GGT GTC TAC TCT AGT GAT CAA TGT CGT GTT CCT     480
```

```
Lys Phe Tyr Lys Ser Gly Val Tyr Ser Ser Asp Gln Cys Arg Val Pro
145                 150                 155                 160

AAT CAC GCA GTA CTG GTT GTT GGT TAT GGA ACC AGT AAA AAA CAC GGG      528
Asn His Ala Val Leu Val Val Gly Tyr Gly Thr Ser Lys Lys His Gly
                165                 170                 175

GAT TAT TGG ATT ATT AAA AAT AGT TGG GGA ACT AAT TGG GGA AGA AAT      576
Asp Tyr Trp Ile Ile Lys Asn Ser Trp Gly Thr Asn Trp Gly Arg Asn
            180                 185                 190

GGA TAT GGT TAT ATG AAG CGA AAC GAA AGG AAT ATG TGT CAT ATC GCT      624
Gly Tyr Gly Tyr Met Lys Arg Asn Glu Arg Asn Met Cys His Ile Ala
        195                 200                 205

ACG ATG GCT TCA TTC CCC ATA                                           645
Thr Met Ala Ser Phe Pro Ile
    210             215
```

(2) INFORMATION FOR SEQ ID NO:38:

(i) SEQUENCE CHARACTERISTICS:
        (A) LENGTH: 215 amino acids
        (B) TYPE: amino acid
        (D) TOPOLOGY: linear (ii) MOLECULE TYPE: protein (xi) SEQUENCE DESCRIPTION: SEQ ID NO:38:

```
Leu Pro Lys Tyr Val Asp Trp Arg Lys Arg Gly Tyr Val Thr Pro Ala
1                5                  10                  15

Lys Glu Gln Gly Leu Cys Gly Ser Cys Tyr Ala Phe Ala Ala Ala
            20                  25                  30

Ala Leu Glu Ala Tyr Asn Lys Lys Thr Lys Asn Lys Leu Leu Asp Leu
        35                  40                  45

Ser Pro Gln Asn Ile Leu Asp Cys Thr Trp Asp Leu Gly Asn Asn Gly
    50                  55                  60

Cys His Gly Gly Phe Met Asn Pro Ala Phe Tyr Tyr Ala Ser Lys Ala
65                  70                  75                  80

Gly Ile Ala Ser Glu Ala Lys Tyr Pro Tyr Val His Thr Ala Arg Arg
            85                  90                  95

Thr Cys Tyr Trp Arg Lys Asp Ile Val Ala Ala Thr Asp Asn Gly Tyr
        100                 105                 110

Thr Arg Ile Gln Gln Gly Asp Glu Lys Gly Leu Gln Tyr Ala Val Ala
    115                 120                 125

Lys Phe Gly Pro Val Val Gly Ile Ser Gly Tyr Gln His Asp Phe
130                 135                 140

Lys Phe Tyr Lys Ser Gly Val Tyr Ser Ser Asp Gln Cys Arg Val Pro
145                 150                 155                 160

Asn His Ala Val Leu Val Val Gly Tyr Gly Thr Ser Lys Lys His Gly
                165                 170                 175

Asp Tyr Trp Ile Ile Lys Asn Ser Trp Gly Thr Asn Trp Gly Arg Asn
            180                 185                 190

Gly Tyr Gly Tyr Met Lys Arg Asn Glu Arg Asn Met Cys His Ile Ala
        195                 200                 205

Thr Met Ala Ser Phe Pro Ile
    210             215
```

(2) INFORMATION FOR SEQ ID NO:39:

(i) SEQUENCE CHARACTERISTICS:
        (A) LENGTH: 645 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:39:

| | | | | | |
|---|---|---|---|---|---|
| TATGGGGAAT | GAAGCCATCG | TAGCGATATG | ACACATATTC | CTTTCGTTTC | GCTTCATATA | 60 |
| ACCATATCCA | TTTCTTCCCC | AATTAGTTCC | CCAACTATTT | TTAATAATCC | AATAATCCCC | 120 |
| GTGTTTTTTA | CTGGTTCCAT | AACCAACAAC | CAGTACTGCG | TGATTAGGAA | CACGACATTG | 180 |
| ATCACTAGAG | TAGACACCGG | ATTTATAAAA | TTTAAAATCG | TGTTGATATC | CAGAAATTCC | 240 |
| AACAACAACG | GGTCCAAATT | TAGCCACAGC | ATATTGAAGA | CCTTTCTCAT | CACCTTGTTG | 300 |
| TATTCGAGTG | TAACCATTAT | CAGTAGCAGC | AACTATATCT | TTCCGCCAAT | AGCATGTACG | 360 |
| TCTTGCAGTG | TGAACATACG | GATATTTCGC | TTCTGATGCA | ATACCTGCCT | TACTTGCATA | 420 |
| ATAAAATGCC | GGATTCATGA | AACCACCATG | GCAACCATTA | TTACCGAGAT | CCCATGTACA | 480 |
| ATCTAGAATA | TTTTGCGGAG | ATAAATCGAG | AAGTTTGTTT | TTCGTCTTTT | TATTATAAGC | 540 |
| TTCTAATGCT | GCAGCTGCAG | CGAATGCATA | ACAACTACCA | CACAAGCCCT | GCTCTTTGGC | 600 |
| AGGTGTGACA | TATCCTCTCT | TTCTCCAATC | AACATATTTT | GGCAG | | 645 |

(2) INFORMATION FOR SEQ ID NO:40:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:40:

CGCAGATCTA TGCTTCGATT CATTGC                                           26

(2) INFORMATION FOR SEQ ID NO:41:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:41:

CGCAGATCTT TATATGGGGA ATGAAGC                                          27

(2) INFORMATION FOR SEQ ID NO:42:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

CCGGAATTCT ACTGCCAAAA TATGTTGATT GG                                    32

(2) INFORMATION FOR SEQ ID NO:43:

(i) SEQUENCE CHARISTICS:
    (A) LENGTH: 1206 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..1206

(xi) SEQUENCE DESCRIPTION: SEQ ID NO:43:

```
ATG CTT CGA TTC ATT GCT TTA TTG GCC ATA CTC ACT TTC TTG ATC GAC        48
Met Leu Arg Phe Ile Ala Leu Leu Ala Ile Leu Thr Phe Leu Ile Asp
 1               5                  10                  15

TTT ACC GTC TCA TTC AAT GAT GAA ATT CTA CAG CTG AAA GAA GTA TTG        96
Phe Thr Val Ser Phe Asn Asp Glu Ile Leu Gln Leu Lys Glu Val Leu
                20                  25                  30

GGA ATG TTT GAT GAA GAT TAC AGA TTA GGA AAT ATG ACG AGA CTT ACG       144
Gly Met Phe Asp Glu Asp Tyr Arg Leu Gly Asn Met Thr Arg Leu Thr
            35                  40                  45

TTT GAT TTT CAA AAC GCT TTG AAA GAT TAC GGC GAT GGA GAA AAC AGT       192
Phe Asp Phe Gln Asn Ala Leu Lys Asp Tyr Gly Asp Gly Glu Asn Ser
        50                  55                  60

TAT AAA CTA ACT GCT GTG CAA TCT TTC CTC AAA AAA TTA GAA GAA AAC       240
Tyr Lys Leu Thr Ala Val Gln Ser Phe Leu Lys Lys Leu Glu Glu Asn
 65                  70                  75                  80

GGT GAG GAA CAA GCG ATG AAA AAA TTA GAA ACC GAA TGG CAA GAG TAT       288
Gly Glu Glu Gln Ala Met Lys Lys Leu Glu Thr Glu Trp Gln Glu Tyr
                 85                  90                  95

TTA ACA GCT CTT GGA AAA GAA TAT GAT TCA GAA GAG AAT AAA TTG AGA       336
Leu Thr Ala Leu Gly Lys Glu Tyr Asp Ser Glu Glu Asn Lys Leu Arg
            100                 105                 110

ATG GCA ATA TTT GAA AGT AAT GAA TTA ATG ACA GAA GCA TTA AAT AGA       384
Met Ala Ile Phe Glu Ser Asn Glu Leu Met Thr Glu Ala Leu Asn Arg
        115                 120                 125

AAA TAT GAG CAA GGC TTA ATT TCA TTT AAA ACT GCC CTG AAT GAT ATG       432
Lys Tyr Glu Gln Gly Leu Ile Ser Phe Lys Thr Ala Leu Asn Asp Met
130                 135                 140

GCT GAT TTG ACC GAT CAA GAA TTC AAC CTA ATG AAT GGA CTT CTA CTG       480
Ala Asp Leu Thr Asp Gln Glu Phe Asn Leu Met Asn Gly Leu Leu Leu
145                 150                 155                 160

CAT AAT GAA ACT TCC CAT ACA AGA AGG TAT GCT CGA CAA GTA TCT GGT       528
His Asn Glu Thr Ser His Thr Arg Arg Tyr Ala Arg Gln Val Ser Gly
                165                 170                 175

GAA TTT CTC AAG TAC AAT AAG AGT ACA AAG CTG CCA AAA TAT GTT GAT       576
Glu Phe Leu Lys Tyr Asn Lys Ser Thr Lys Leu Pro Lys Tyr Val Asp
            180                 185                 190

TGG AGA AAG AGA GGA TAT GTC ACA CCT GCC AAA GAG CAG GGC TTG TGT       624
Trp Arg Lys Arg Gly Tyr Val Thr Pro Ala Lys Glu Gln Gly Leu Cys
        195                 200                 205

GGT AGT TGT TAT GCA TTC GCT GCA GCT GCA TTA GAA GCT TAT AAT           672
Gly Ser Cys Tyr Ala Phe Ala Ala Ala Ala Leu Glu Ala Tyr Asn
        210                 215                 220

AAA AAG ACG AAA AAC AAA CTT CTC GAT TTA TCT CCG CAA AAT ATT CTA       720
Lys Lys Thr Lys Asn Lys Leu Leu Asp Leu Ser Pro Gln Asn Ile Leu
225                 230                 235                 240

GAT TGT ACA TGG GAT CTC GGT AAT AAT GGT TGC CAT GGT GGT TTC ATG       768
Asp Cys Thr Trp Asp Leu Gly Asn Asn Gly Cys His Gly Gly Phe Met
                245                 250                 255

AAT CCG GCA TTT TAT TAT GCA AGT AAG GCA GGT ATT GCA TCA GAA GCG       816
```

```
Asn Pro Ala Phe Tyr Tyr Ala Ser Lys Ala Gly Ile Ala Ser Glu Ala
            260                 265                 270

AAA TAT CCG TAT GTT CAC ACT GCA AGA CGT ACA TGC TAT TGG CGG AAA          864
Lys Tyr Pro Tyr Val His Thr Ala Arg Arg Thr Cys Tyr Trp Arg Lys
            275                 280                 285

GAT ATA GTT GCT GCT ACT GAT AAT GGT TAC ACT CGA ATA CAA CAA GGT          912
Asp Ile Val Ala Ala Thr Asp Asn Gly Tyr Thr Arg Ile Gln Gln Gly
        290                 295                 300

GAT GAG AAA GGT CTT CAA TAT GCT GTG GCT AAA TTT GGA CCC GTT GTT          960
Asp Glu Lys Gly Leu Gln Tyr Ala Val Ala Lys Phe Gly Pro Val Val
305                 310                 315                 320

GTT GGA ATT TCT GGA TAT CAA CAC GAT TTT AAA TTT TAT AAA TCC GGT         1008
Val Gly Ile Ser Gly Tyr Gln His Asp Phe Lys Phe Tyr Lys Ser Gly
                325                 330                 335

GTC TAC TCT AGT GAT CAA TGT CGT GTT CCT AAT CAC GCA GTA CTG GTT         1056
Val Tyr Ser Ser Asp Gln Cys Arg Val Pro Asn His Ala Val Leu Val
            340                 345                 350

GTT GGT TAT GGA ACC AGT AAA AAA CAC GGG GAT TAT TGG ATT ATT AAA         1104
Val Gly Tyr Gly Thr Ser Lys Lys His Gly Asp Tyr Trp Ile Ile Lys
        355                 360                 365

AAT AGT TGG GGA ACT AAT TGG GGA AGA AAT GGA TAT GGT TAT ATG AAG         1152
Asn Ser Trp Gly Thr Asn Trp Gly Arg Asn Gly Tyr Gly Tyr Met Lys
370                 375                 380

CGA AAC GAA AGG AAT ATG TGT CAT ATC GCT ACG ATG GCT TCA TTC CCC         1200
Arg Asn Glu Arg Asn Met Cys His Ile Ala Thr Met Ala Ser Phe Pro
385                 390                 395                 400

ATA TAA                                                                  1206
Ile *

(2) INFORMATION FOR SEQ ID NO:44:

(i) SEQUENCE CHARACTERISTICS:
        (A) LENGTH: 401 amino acids
        (B) TYPE: amino acid
        (D) TOPOLOGY: linear (ii) MOLECULE TYPE: protein (xi) SEQUENCE DESCRIPTION: SEQ ID NO:44:

Met Leu Arg Phe Ile Ala Leu Leu Ala Ile Leu Thr Phe Leu Ile Asp
  1               5                  10                  15

Phe Thr Val Ser Phe Asn Asp Glu Ile Leu Gln Leu Lys Glu Val Leu
             20                  25                  30

Gly Met Phe Asp Glu Asp Tyr Arg Leu Gly Asn Met Thr Arg Leu Thr
         35                  40                  45

Phe Asp Phe Gln Asn Ala Leu Lys Asp Tyr Gly Asp Gly Glu Asn Ser
     50                  55                  60

Tyr Lys Leu Thr Ala Val Gln Ser Phe Leu Lys Leu Glu Glu Asn
 65                  70                  75                  80

Gly Glu Glu Gln Ala Met Lys Lys Leu Glu Thr Glu Trp Gln Glu Tyr
                 85                  90                  95

Leu Thr Ala Leu Gly Lys Glu Tyr Asp Ser Glu Asn Lys Leu Arg
                100                 105                 110

Met Ala Ile Phe Glu Ser Asn Glu Leu Met Thr Glu Ala Leu Asn Arg
            115                 120                 125

Lys Tyr Glu Gln Gly Leu Ile Ser Phe Lys Thr Ala Leu Asn Asp Met
        130                 135                 140

Ala Asp Leu Thr Asp Gln Glu Phe Asn Leu Met Asn Gly Leu Leu Leu
145                 150                 155                 160
```

```
His Asn Glu Thr Ser His Thr Arg Arg Tyr Ala Arg Gln Val Ser Gly
            165                 170                 175

Glu Phe Leu Lys Tyr Asn Lys Ser Thr Lys Leu Pro Lys Tyr Val Asp
            180                 185                 190

Trp Arg Lys Arg Gly Tyr Val Thr Pro Ala Lys Glu Gln Gly Leu Cys
            195                 200                 205

Gly Ser Cys Tyr Ala Phe Ala Ala Ala Ala Ala Leu Glu Ala Tyr Asn
            210                 215                 220

Lys Lys Thr Lys Asn Lys Leu Leu Asp Leu Ser Pro Gln Asn Ile Leu
225                 230                 235                 240

Asp Cys Thr Trp Asp Leu Gly Asn Asn Gly Cys His Gly Gly Phe Met
            245                 250                 255

Asn Pro Ala Phe Tyr Ala Ser Lys Ala Gly Ile Ala Ser Glu Ala
            260                 265                 270

Lys Tyr Pro Tyr Val His Thr Ala Arg Arg Thr Cys Tyr Trp Arg Lys
            275                 280                 285

Asp Ile Val Ala Ala Thr Asp Asn Gly Tyr Thr Arg Ile Gln Gln Gly
            290                 295                 300

Asp Glu Lys Gly Leu Gln Tyr Ala Val Ala Lys Phe Gly Pro Val Val
305                 310                 315                 320

Val Gly Ile Ser Gly Tyr Gln His Asp Phe Lys Phe Tyr Lys Ser Gly
            325                 330                 335

Val Tyr Ser Ser Asp Gln Cys Arg Val Pro Asn His Ala Val Leu Val
            340                 345                 350

Val Gly Tyr Gly Thr Ser Lys Lys His Gly Asp Tyr Trp Ile Ile Lys
            355                 360                 365

Asn Ser Trp Gly Thr Asn Trp Gly Arg Asn Gly Tyr Gly Tyr Met Lys
            370                 375                 380

Arg Asn Glu Arg Asn Met Cys His Ile Ala Thr Met Ala Ser Phe Pro
385                 390                 395                 400

Ile (2) INFORMATION FOR SEQ ID NO:45:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..726

(xi) SEQUENCE DESCRIPTION: SEQ ID NO:45:

ATG AAC AAA CTT TTC ATA GTT CTT GGC TTA GCG CTT CTT TTT GTT GCA        48
Met Asn Lys Leu Phe Ile Val Leu Gly Leu Ala Leu Leu Phe Val Ala
 1               5                  10                  15

TTA CCT TCC GCA TCA GAA TCT AGA ATT CTA CTG CCA AAA TAT GTT GAT        96
Leu Pro Ser Ala Ser Glu Ser Arg Ile Leu Leu Pro Lys Tyr Val Asp
                20                  25                  30

TGG AGA AAG AGA GGA TAT GTC ACA CCT GCC AAA GAG CAG GGC TTG TGT       144
Trp Arg Lys Arg Gly Tyr Val Thr Pro Ala Lys Glu Gln Gly Leu Cys
            35                  40                  45

GGT AGT TGT TAT GCA TTC GCT GCA GCT GCA GCA TTA GAA GCT TAT AAT       192
Gly Ser Cys Tyr Ala Phe Ala Ala Ala Ala Ala Leu Glu Ala Tyr Asn
```

```
           50                      55                      60
AAA AAG ACG AAA AAC AAA CTT CTC GAT TTA TCT CCG CAA AAT ATT CTA     240
Lys Lys Thr Lys Asn Lys Leu Leu Asp Leu Ser Pro Gln Asn Ile Leu
 65                  70                      75                  80

GAT TGT ACA TGG GAT CTC GGT AAT AAT GGT TGC CAT GGT GGT TTC ATG     288
Asp Cys Thr Trp Asp Leu Gly Asn Asn Gly Cys His Gly Gly Phe Met
                 85                      90                      95

AAT CCG GCA TTT TAT TAT GCA AGT AAG GCA GGT ATT GCA TCA GAA GCG     336
Asn Pro Ala Phe Tyr Tyr Ala Ser Lys Ala Gly Ile Ala Ser Glu Ala
             100                     105                     110

AAA TAT CCG TAT GTT CAC ACT GCA AGA CGT ACA TGC TAT TGG CGG AAA     384
Lys Tyr Pro Tyr Val His Thr Ala Arg Arg Thr Cys Tyr Trp Arg Lys
             115                     120                     125

GAT ATA GTT GCT GCT ACT GAT AAT GGT TAC ACT CGA ATA CAA CAA GGT     432
Asp Ile Val Ala Ala Thr Asp Asn Gly Tyr Thr Arg Ile Gln Gln Gly
 130                     135                     140

GAT GAG AAA GGT CTT CAA TAT GCT GTG GCT AAA TTT GGA CCC GTT GTT     480
Asp Glu Lys Gly Leu Gln Tyr Ala Val Ala Lys Phe Gly Pro Val Val
 145                     150                     155                 160

GTT GGA ATT TCT GGA TAT CAA CAC GAT TTT AAA TTT TAT AAA TCC GGT     528
Val Gly Ile Ser Gly Tyr Gln His Asp Phe Lys Phe Tyr Lys Ser Gly
                 165                     170                     175

GTC TAC TCT AGT GAT CAA TGT CGT GTT CCT AAT CAC GCA GTA CTG GTT     576
Val Tyr Ser Ser Asp Gln Cys Arg Val Pro Asn His Ala Val Leu Val
                 180                     185                     190

GTT GGT TAT GGA ACC AGT AAA AAA CAC GGG GAT TAT TGG ATT ATT AAA     624
Val Gly Tyr Gly Thr Ser Lys Lys His Gly Asp Tyr Trp Ile Ile Lys
             195                     200                     205

AAT AGT TGG GGA ACT AAT TGG GGA AGA AAT GGA TAT GGT TAT ATG AAG     672
Asn Ser Trp Gly Thr Asn Trp Gly Arg Asn Gly Tyr Gly Tyr Met Lys
 210                     215                     220

CGA AAC GAA AGG AAT ATG TGT CAT ATC GCT ACG ATG GCT TCA TTC CCC     720
Arg Asn Glu Arg Asn Met Cys His Ile Ala Thr Met Ala Ser Phe Pro
 225                     230                     235                 240

ATA TAA                                                              726
Ile *

(2) INFORMATION FOR SEQ ID NO:46:

(i) SEQUENCE CHARACTERISTICS:
        (A) LENGTH: 241 amino acids
        (B) TYPE: amino acid
        (D) TOPOLOGY: linear (ii) MOLECULE TYPE: protein (xi) SEQUENCE DESCRIPTION: SEQ ID NO:46:

Met Asn Lys Leu Phe Ile Val Leu Gly Leu Ala Leu Leu Phe Val Ala
 1               5                  10                      15

Leu Pro Ser Ala Ser Glu Ser Arg Ile Leu Leu Pro Lys Tyr Val Asp
             20                      25                      30

Trp Arg Lys Arg Gly Tyr Val Thr Pro Ala Lys Glu Gln Gly Leu Cys
             35                      40                      45

Gly Ser Cys Tyr Ala Phe Ala Ala Ala Ala Leu Glu Ala Tyr Asn
         50                      55                      60

Lys Lys Thr Lys Asn Lys Leu Leu Asp Leu Ser Pro Gln Asn Ile Leu
 65                  70                      75                  80

Asp Cys Thr Trp Asp Leu Gly Asn Asn Gly Cys His Gly Gly Phe Met
                 85                      90                      95
```

-continued

```
Asn Pro Ala Phe Tyr Tyr Ala Ser Lys Ala Gly Ile Ala Ser Glu Ala
        100                 105                 110

Lys Tyr Pro Tyr Val His Thr Ala Arg Arg Thr Cys Tyr Trp Arg Lys
        115                 120                 125

Asp Ile Val Ala Ala Thr Asp Asn Gly Tyr Thr Arg Ile Gln Gln Gly
    130                 135                 140

Asp Glu Lys Gly Leu Gln Tyr Ala Val Ala Lys Phe Gly Pro Val Val
145                 150                 155                 160

Val Gly Ile Ser Gly Tyr Gln His Asp Phe Lys Phe Tyr Lys Ser Gly
                165                 170                 175

Val Tyr Ser Ser Asp Gln Cys Arg Val Pro Asn His Ala Val Leu Val
            180                 185                 190

Val Gly Tyr Gly Thr Ser Lys Lys His Gly Asp Tyr Trp Ile Ile Lys
        195                 200                 205

Asn Ser Trp Gly Thr Asn Trp Gly Arg Asn Gly Tyr Gly Tyr Met Lys
    210                 215                 220

Arg Asn Glu Arg Asn Met Cys His Ile Ala Thr Met Ala Ser Phe Pro
225                 230                 235                 240

Ile
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated nucleic acid molecule selected from the group consisting of:
   (a) a cDNA or a RNA encoding a protein having an amino acid sequence selected from the group consisting of SEQ ID NO:6, SEQ ID NO:15, SEQ ID NO:17, SEQ ID NO:33, SEQ ID NO:38, SEQ ID NO:44, and SEQ ID NO:46; and
   (b) a nucleic acid molecule comprising a complement of a nuclei acid molecule as recited in (a).

2. The nucleic acid molecule of claim 1, wherein said nucleic acid molecule comprises a nucleic acid sequence that encodes a protein selected from the group consisting of a *Dirofilaria immitis* third-larval stage cysteine protease protein and an *Onchocerca volvulus* third-larval stage cysteine protease protein.

3. An isolated nucleic acid molecule selected from the group consisting of: a nucleic acid molecule comprising a nucleic acid sequence selected from the group consisting of SEQ ID NO:5, SEQ ID NO:7, SEQ ID NO:14, SEQ ID NO:16, SEQ ID NO:28, SEQ ID NO:29, SEQ ID NO:30, SEQ ID NO:31, SEQ ID NO:32, SEQ ID NO:34, SEQ ID NO:35, SEQ ID NO:36, SEQ ID NO:37, and SEQ ID NO:39.

4. An isolated rcombinant molecule comprising the nucleic acid molecule as set forth in claim 1 operatively linked to a transcription control sequence.

5. An isolated rcombinant virus comprising the nucleic acid molecule as set forth in claim 1.

6. An isolated recombinant cell comprising the nucleic acid molecule as set forth in claim 1, said cell being capable of expressing said nucleic acid molecule.

7. A composition comprising an excipient and an isolated nucleic acid molecule selected from the group consisting of: a *Dirofilaria immitis* cDNA molecule, a *Dirofilaria immitis* RNA molecule, an *Onchocerca volvulus* cDNA molecule, and an *Onchocerca volvulus* RNA molecule, wherein said nucleic acid molecule encodes a protein having cysteine protease activity and said nucleic acid molecule hybridzes to a nucleic acid sequence complementary to a nucleic acid sequence selected from the group consisting of SEQ ID NO:5, SEQ ID NO:7, SEQ ID NO:14, SEQ ID NO:16, SEQ ID NO:32, SEQ ID NO:34, and SEQ ID NO:37, under conditions comprising (1) hybridizing in a solution comprising 2X SSC in the absence of nucleic acid helix destabilizing agents, at a temperature of 37° C., and (2) washing in 1X SSC in the absence of nucleic acid helix destabilizing agents at a temperature of 69° C.; and
   a nucleic acid molecule comprising a complement of said isolated nucleic acid molecule.

8. The composition of claim 7, wherein said composition further comprises a component selected from the group consisting of an adjuvant, a carrier, and a mixture thereof.

9. The composition of claim 7, wherein said composition is selected from the group consisting of a naked nucleic acid vaccine, a recombinant virus vaccine a recombinant cell vaccine.

10. An isolated nucleic acid molecule selected from the group consisting of a *Dirofilaria immitis* cDNA molecule, *Dirofilaria immitis* RNA molecule, an *Onchocerca volvulus* cDNA molecule, and an *Onchocera volvulus* RNA molecule, wherein said nucleic acid molecule encodes a protein having cysteine protease activity and said nucleic acid molecule hybridizes to a nucleic acid sequence complementary to a nucleic acid sequence selected from the group consisting of SEQ ID NO:5, SEQ ID NO:7, SEQ ID NO:14, SEQ ID NO:16, SEQ ID NO:32, SEQ ID NO:34, and SEQ ID NO:37, under conditions comprising hybridization and wash conditions which allow 10% or less base-pair mismatch, wherein such conditions are determined by a formula:

$$T_m = 81.5° C. + 16.6 \log M + 0.41(\% G+C) - 500/n - 0.61(\% \text{formamide}),$$

wherein
   $T_m$ represents the temperature at which two complementary nucleic acid molecule stands will disassociate, assuming 100% complementary between the two stands, n represents the number of nucleotides in the shorter stand of the duplex being hybridized and log M represents the ionic strengths of the hybridization and wash solutions in moles/liter;

wherein said wash is conducted at a temperature of $T_m$ minus 10° C.; and a nucleic acid molecule fully complementary to said isolated nucleic acid molecule.

11. An isolated nucleic acid molecule selected from the group consisting of a *Dirofilaria immitis* cDNA molecule, a *Dirofilaria immitis* RNA molecule, an *Onchocerca volvulus* cDNA molecule, and an *Onchocerca volvulus* RNA molecule, wherein said nucleic acid molecule encodes a protein having cysteine protease activity and said nucleic acid molecule hybridizes to a nucleic acid sequence complementary to a nucleic acid sequence selected from the group consisting of SEQ ID NO:5, SEQ ID NO:7, SEQ ID NO:14, SEQ ID NO:16, SEQ ID NO:32, SEQ ID NO:34, and SEQ ID NO:37, under conditions comprising (a) hybridizing in a solution comprising 2X SSC in the absence of nucleic acid helix destabilizing agents, at a temperature of 37° C., and (b) washing in 1X SSC in the absence of nucleic acid helix destabilizing agents at a temperature of 69° C. and a nucleic acid molecule fully complementary to said isolated nucleic acid molecule.

12. The nucleic acid molecule claim 11, wherein said nucleic acid molecule comprises a nucleic acid sequence that encodes a protein selected from the group consisting of a *Dirofilaria immitis* third-larval stage cysteine protease protein and an *Onchocerca volvulus* third-larval stage cysteine protease protein.

13. An isolated recombinant molecule comprising the nucleic acid molecule as set forth in claim 11, operatively linked to a transcription control sequence.

14. An isolated recombinant virus comprising the nucleic acid molecule as set forth in claim 11.

15. An isolated recombinant cell comprising the nucleic acid molecule as set forth in claim 11, said cell being capable of expressing said nucleic acid molecule.

* * * * *

UNITED STATES PATENT AND TRADEMARK OFFICE
CERTIFICATE OF CORRECTION

PATENT NO. : 6,365,392 B1 Page 1 of 1
DATED : April 2, 2002
INVENTOR(S) : Cynthia Ann Tripp et al.

It is certified that error appears in the above-identified patent and that said Letters Patent is hereby corrected as shown below:

Column 101,
Line 43, please delete "nucle acid" and replace with -- nucleic acid --.
Lines 58 and 61, please delete "rcombinant" and replace with -- recombinant --.

Column 102,
Line 48, please delete "vaccine a recombinant cell" with -- vaccine and a recombinant cell --.
Line 67, please delete "stands" and replace with -- strands --.

Column 103,
Line 1, please delete "complementary" and replace with -- complementarity --.
Line 3, please delete "stand" and replace with -- strand --.

Signed and Sealed this

Twenty-ninth Day of April, 2003

JAMES E. ROGAN
*Director of the United States Patent and Trademark Office*